US010900018B2

(12) United States Patent
Scheel et al.

(10) Patent No.: US 10,900,018 B2
(45) Date of Patent: Jan. 26, 2021

(54) MEANS AND METHODS FOR GENERATION OF BREAST STEM CELLS

(71) Applicant: Helmholtz Zentrum München—Deutsches Forschungszentrum Für Gesundheit Und Umwelt (GMBH), Neuherberg (DE)

(72) Inventors: Christina H. Scheel, Munich (DE); Jelena R. Linnemann, Munich (DE); Lisa K. Meixner, Munich (DE); Haruko Miura, Munich (DE)

(73) Assignee: Helmholtz Zentrum München—Deutsches Forschungszentrum Für Gesundheit Und Umwelt (GMBH), Neuherberg (DE)

( * ) Notice: Subject to any disclaimer, the term of this patent is extended or adjusted under 35 U.S.C. 154(b) by 0 days.

(21) Appl. No.: 15/570,527

(22) PCT Filed: Apr. 28, 2016

(86) PCT No.: PCT/IB2016/052407
§ 371 (c)(1),
(2) Date: Oct. 30, 2017

(87) PCT Pub. No.: WO2016/174604
PCT Pub. Date: Nov. 3, 2016

(65) Prior Publication Data
US 2018/0155686 A1    Jun. 7, 2018

(30) Foreign Application Priority Data
Apr. 30, 2015   (LU) .......................................... 92706

(51) Int. Cl.
*C12N 5/071* (2010.01)
*A61P 35/00* (2006.01)
*A61K 35/36* (2015.01)

(52) U.S. Cl.
CPC ............ *C12N 5/0631* (2013.01); *A61K 35/36* (2013.01); *A61P 35/00* (2018.01); *C12N 2501/01* (2013.01); *C12N 2501/727* (2013.01); *C12N 2513/00* (2013.01); *C12N 2533/54* (2013.01)

(58) Field of Classification Search
CPC .............. C12N 5/0631; C12N 2501/01; C12N 2501/727; C12N 2513/00; C12N 2533/54; A61P 35/00; A61K 35/36
USPC .......................................................... 424/93.7
See application file for complete search history.

(56) References Cited

U.S. PATENT DOCUMENTS

2013/0055417 A1*   2/2013   Ince .................... C12N 5/0631
800/3

FOREIGN PATENT DOCUMENTS

WO    WO 2012/143401    * 10/2012

OTHER PUBLICATIONS

Dontu et al., In vitro propagation and transcriptional profiling of human mammary stem/progenitor cells, Genes & Development, vol. 17, (2003), pp. 1253-1270.*
Keller, P.J., et al., (2011) "Defining the Cellular Precursors to Human Breast Cancer," Proceedings of the National Academy of Sciences 109:2772-2777.
Nedvetsky, P.I., et al. (2012) "Cyclic AMP Regulates Formation of Mammary Epithelial Acini In Vitro," Molecular Biology of the Cell 23:2973-2981.
Shackleton, M., et al. (2006) "Generation of a Functional Mammary Gland from a Single Stem Cell," Nature 439:84-88.
Stingl, J., et al. (2006) "Purification and Unique Properties of Mammary Epithelial Stem Cells," Nature 439:993-997.
Eirew, P., et al. (2008) "A Method for Quantifying Normal Human Mammary Epithelial Stem Cells with In Vivo Regenerative Ability," Nature Medicine, 14:1384-1389.

* cited by examiner

*Primary Examiner* — Jennifer M. H. Tichy
(74) *Attorney, Agent, or Firm* — Kagan Binder, PLLC

(57) ABSTRACT

The present invention is in the field of stem cell biology, in particular in the field of developmental and regenerative biology. The invention generally relates to a method of generating cells capable of differentiating to a multicellular organoid unit that morphologically and/or functionally resembles the terminal ductal-lobular unit. More precisely, said cells are generated by dissociating mammary epithelial tissue, thereby gaining cells and culturing said cells in presence of a compound which elevates cAMP levels in a collagen gel. Under said culturing conditions said cells form a multicellular organoid unit facilitating to obtain a breast stem cell by isolating a single cell from said multicellular organoid unit. The present invention also relates to enriching said cells and differentiating them to a multicellular organoid that morphologically and/or functionally resembles the terminal ductal-lobular unit and use of said cells or said multicellular organoid in testing a compound. Furthermore, the present invention relates to a composition comprising said breast stem cells or the multicellular organoid.

Figure 1:
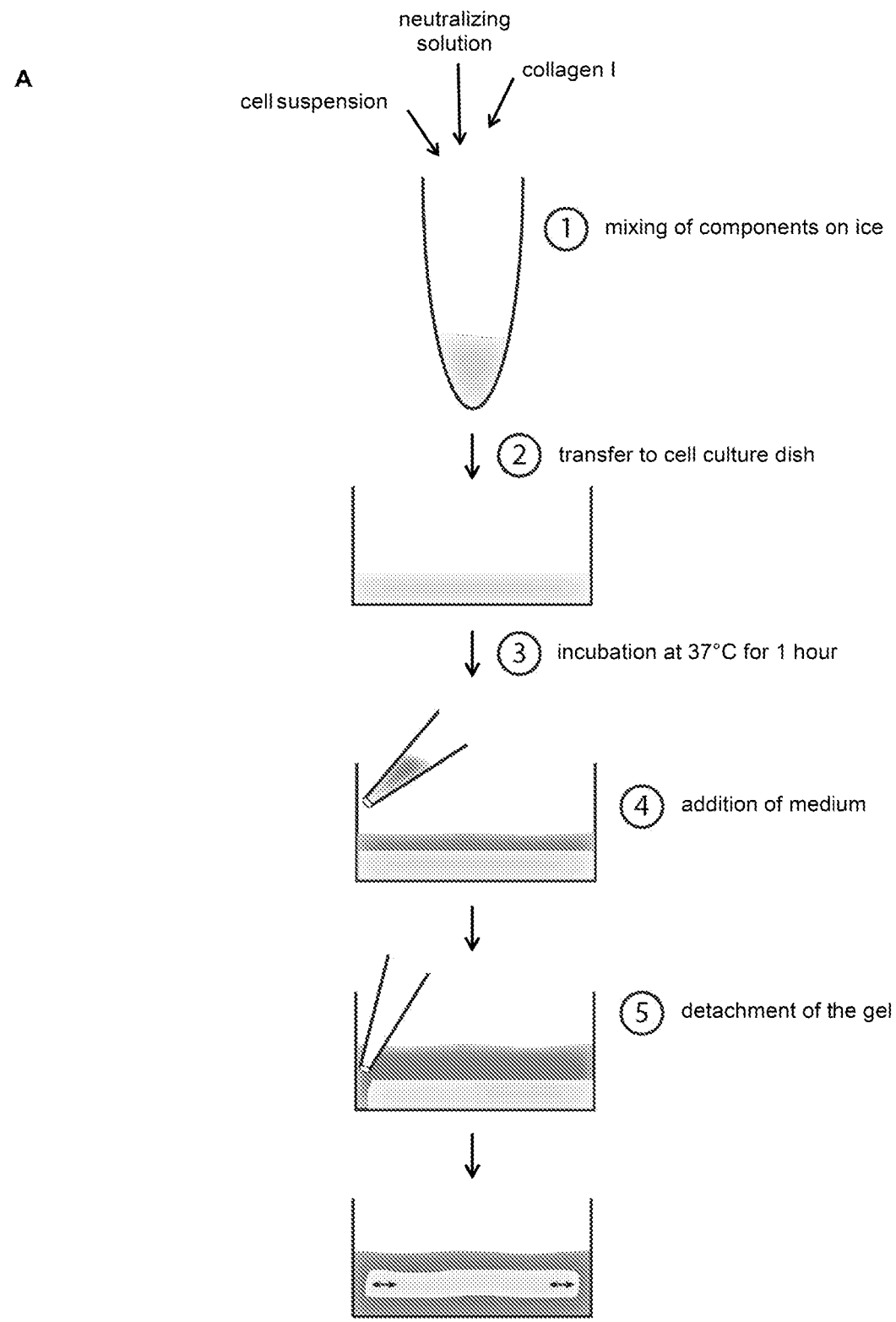
Figure 1:
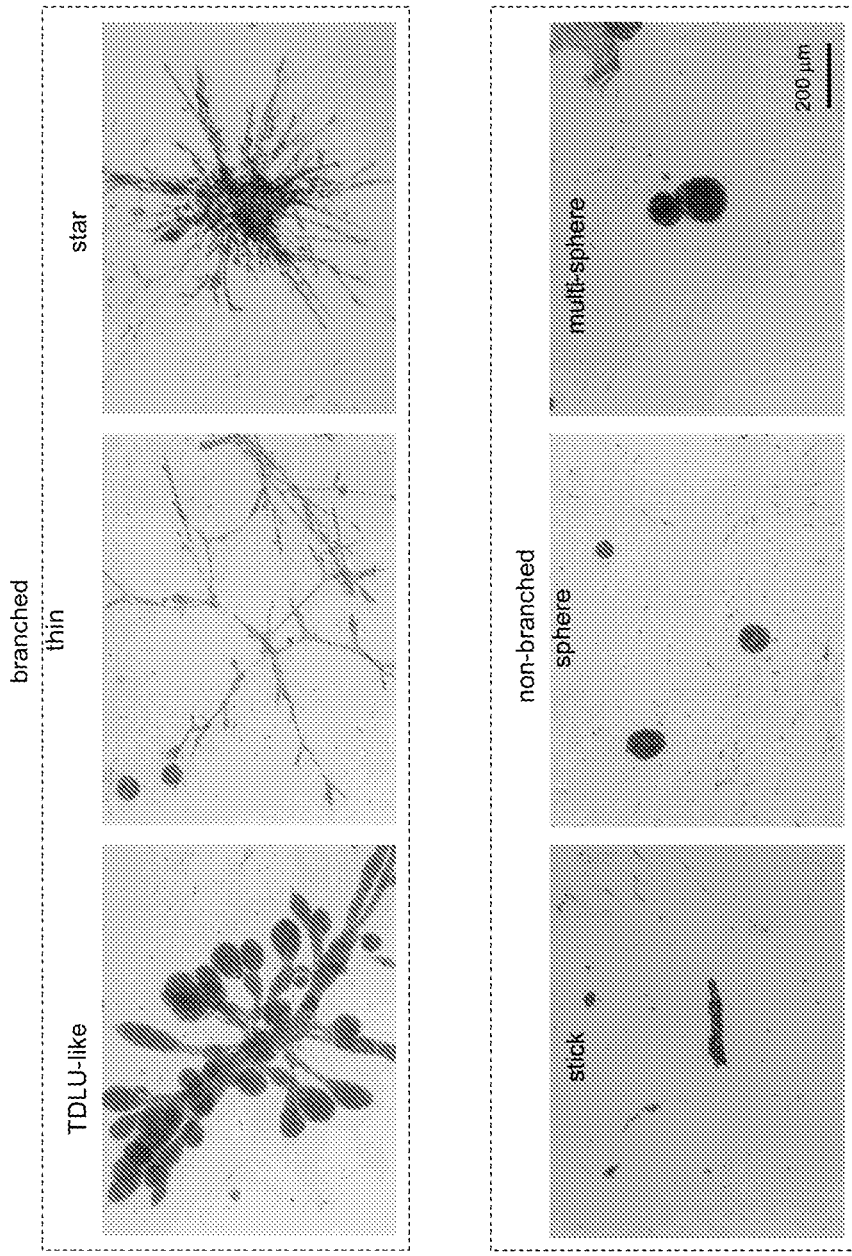
Figure 1:
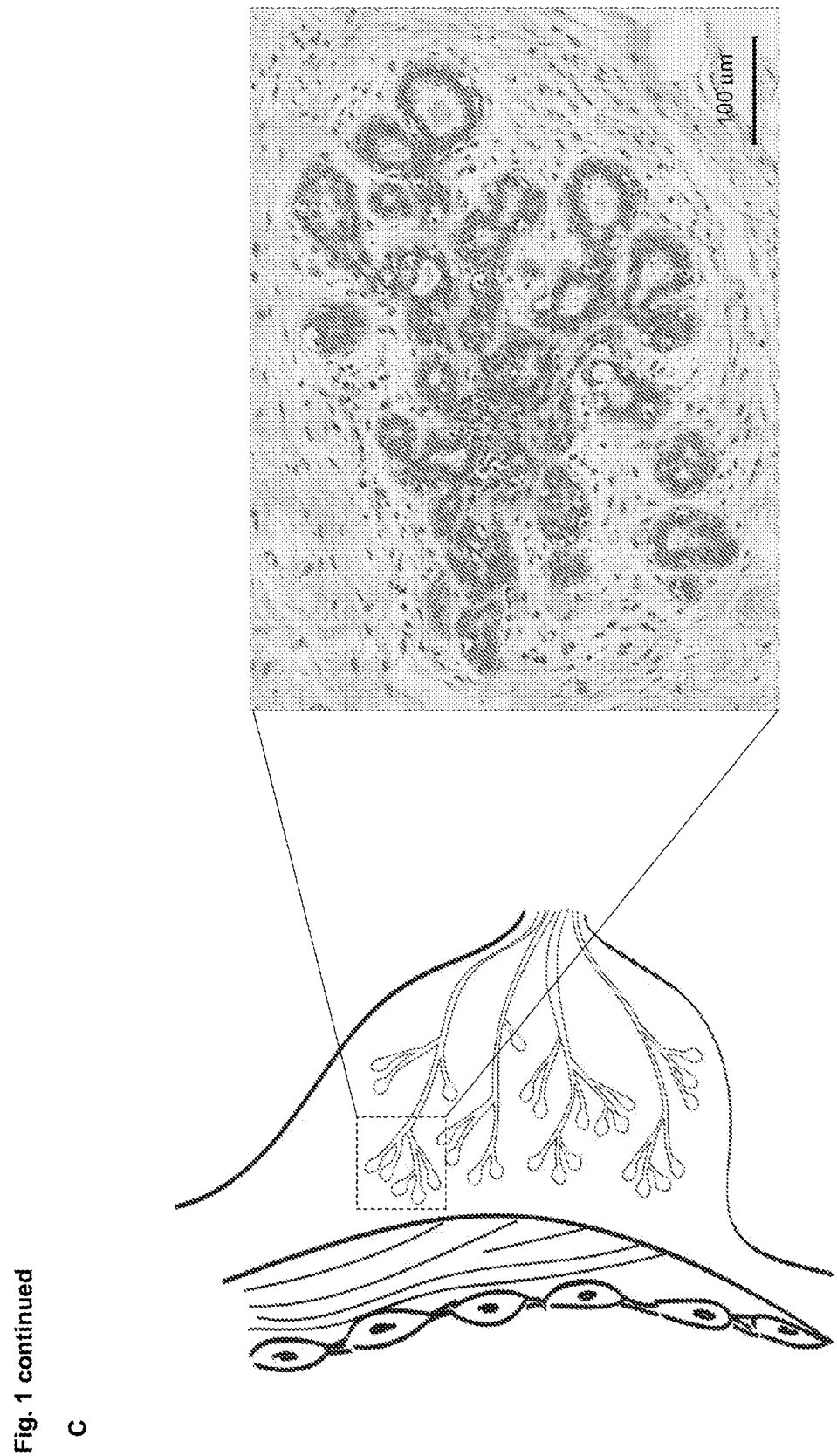
Figure 1:
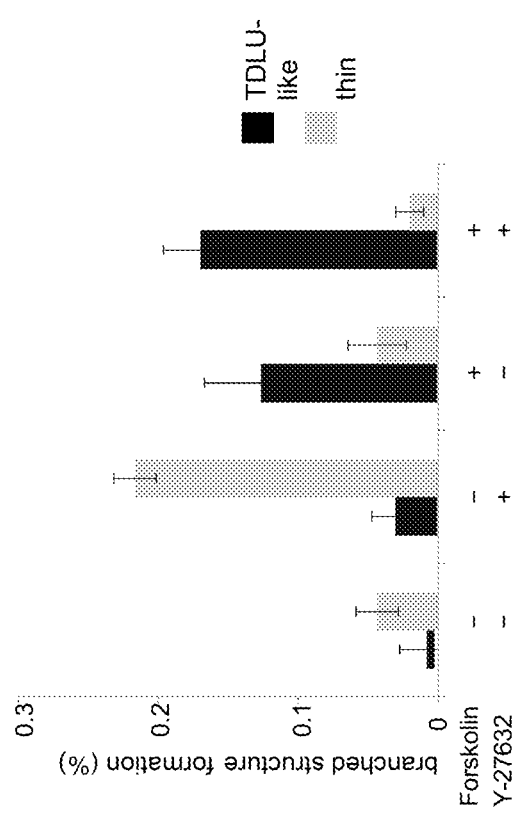
Figure 1:
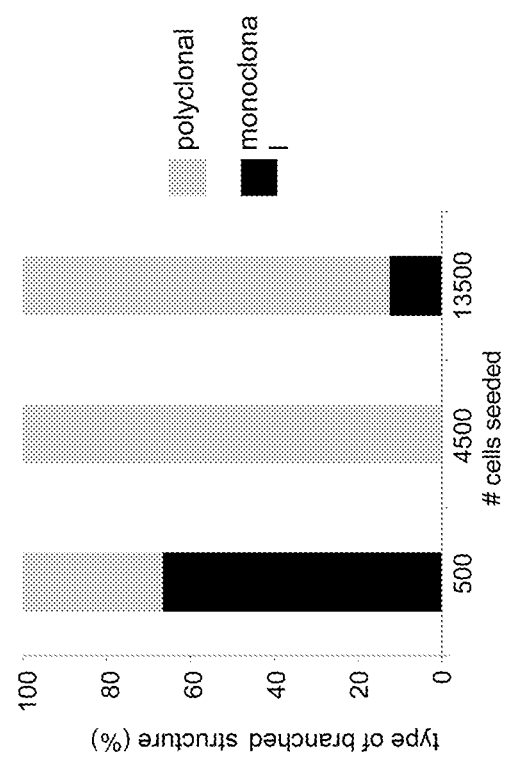
Figure 1:
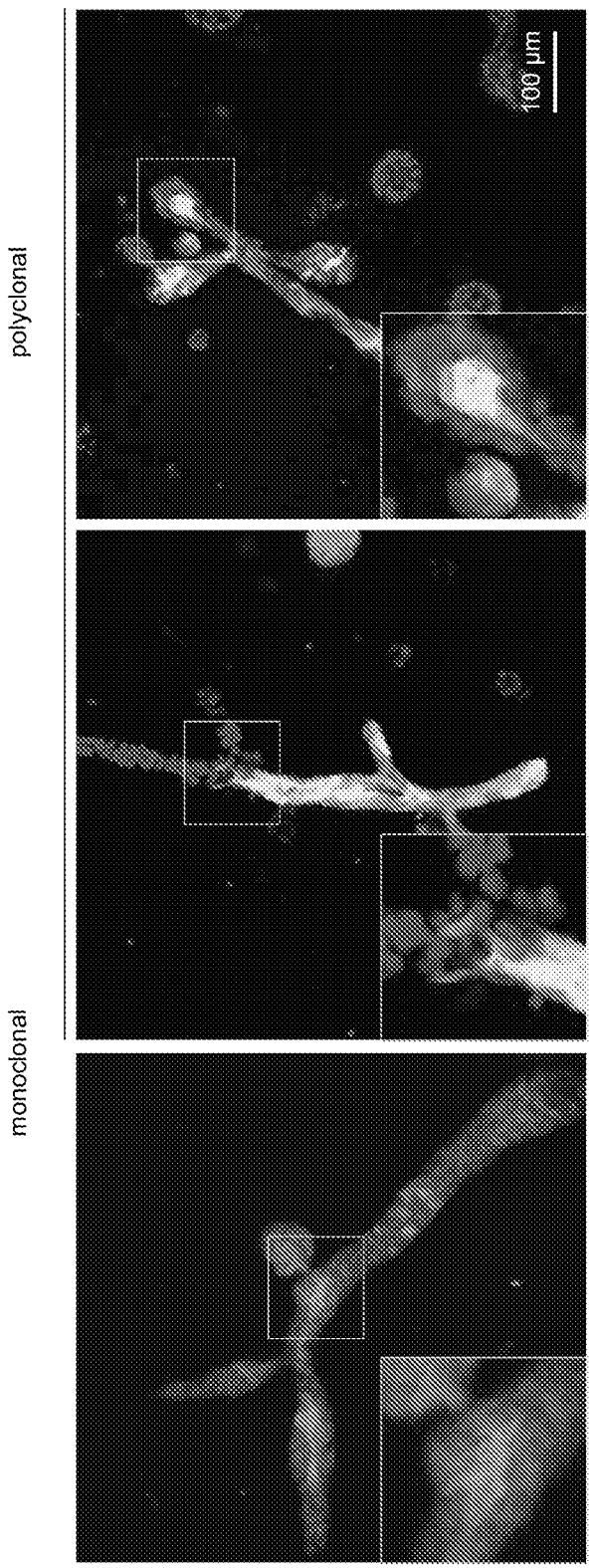

6 Claims, 40 Drawing Sheets
Specification includes a Sequence Listing.

A

B c

D

E

F

| cells seeded M8 | positive gels/total gels | |
|---|---|---|
| | sphere | branched (average number of structures/gel) |
| 125 | 7/8 | 1/8 (0.13) |
| 250 | 8/8 | 0/8 (n.a.) |
| 500 | 8/8 | 4/8 (0.63) |
| 750 | 8/8 | 4/8 (0.88) |
| 1000 | 8/8 | 6/8 (1.50) |
| 1500 | 8/8 | 6/8 (2.00) |
| SFU | 1/55 (S-SFU) | 1/1005 (B-SFU) |
| 95% CI | 1/26 – 1/118 | 1/645 – 1/1564 |

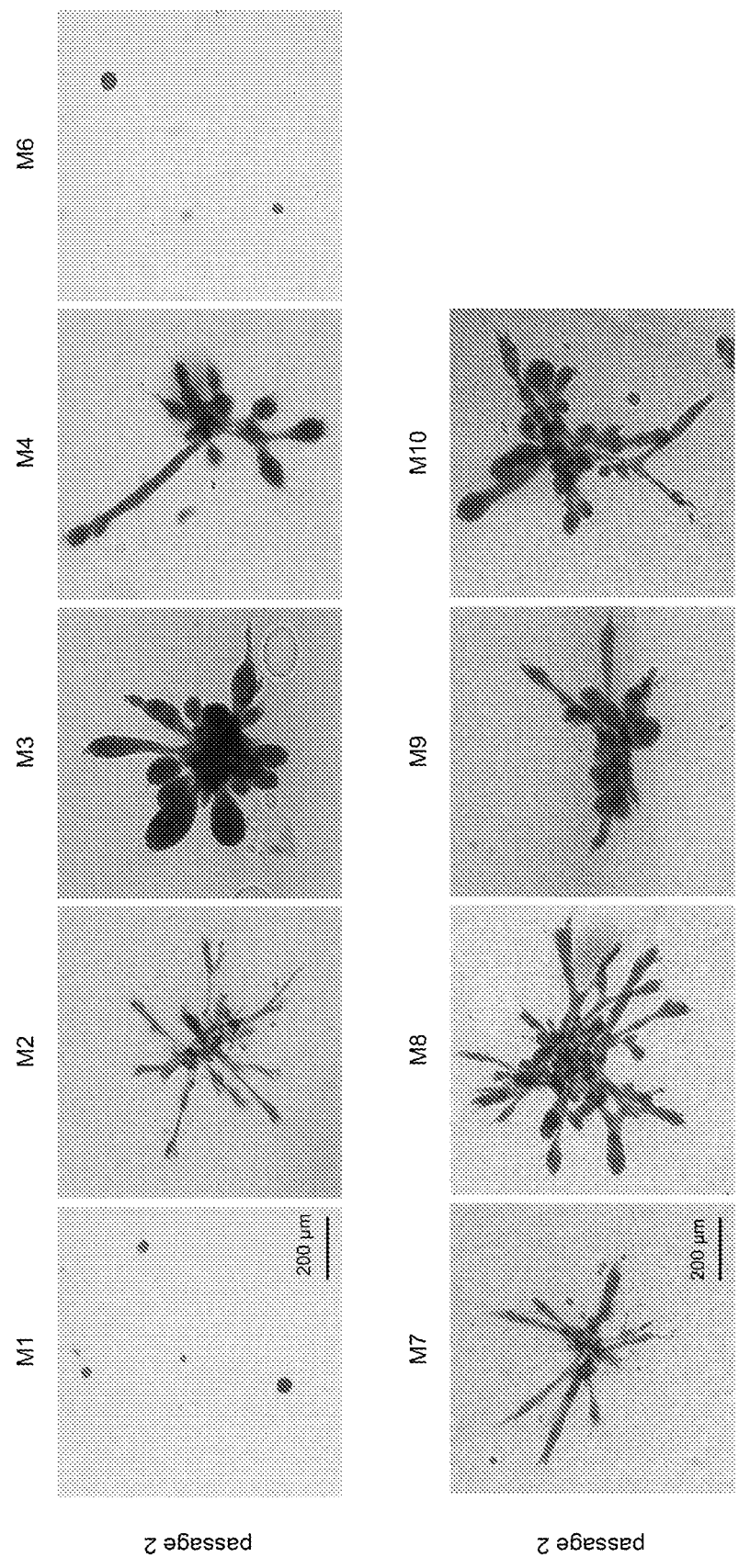

D

Fig. 4 continued

E

| Population | Cells seeded | Positive gels/ total gels (Average number of structures/ gel) | | | B-SFU (95% CI) |
|---|---|---|---|---|---|
| | | M8 | M9 | M10 | |
| Basal + | 125 | 2/8 (0.25) | 2/7 (0.43) | 1/8 (0.25) | 1/413 (1/291 - 1/585) |
| | 250 | 3/8 (0.38) | 4/8 (0.50) | 2/8 (0.25) | |
| | 500 | 5/8 (0.75) | 8/8 (2.25) | 6/8 (1.00) | |
| Basal - | 1000 | 0/8 | 1/8 (0.13) | 0/8 | 1/12386 (1/7034 - 1/21811) |
| | 2000 | 2/8 (0.25) | 2/8 (0.25) | 0/8 | |
| | 4000 | 4/8 (0.50) | 2/8 (0.25) | 1/8 (0.13) | |
| Basal all | 250 | 0/8 | 1/8 (0.13) | 1/7 (0.14) | 1/2690 (1/1562 - 1/4635) |
| | 500 | 0/8 | 1/8 (0.25) | 2/7 (0.29) | |
| | 1000 | 3/8 (0.75) | 2/8 (0.25) | 3/7 (0.86) | |
| LP | 500 | 1/8 (0.13) | 0/8 | 0/8 | 1/5122 (1/3372 - 1/7778) |
| | 1000 | 3/8 (0.50) | 0/14 | 3/14 (0.63) | |
| | 2000 | 9/14 (1.50) | 0/14 | 6/14 (1.00) | | c

D

E

| GO-term (GO-term ID/ pathway ID) | p-value | observed genes | top regulated genes |
|---|---|---|---|
| circulatory system development (GO:0072359) | 3.84E-19 | 116 | CDH5 |
| cytokine receptor binding (GO:0005126) | 1.98E-06 | 31 | CCL21 |
| antigen binding (GO:0003823) | 1.05E-03 | 12 | IGKC, IGHA1, IGHG1, IGJ |
| vascular endothelial growth factor (VEGF) (PW_VEGF_HOMO_SAPIENS) | 8.89E-15 | 51 | CDH5, ECSCR |
| angiogenesis (PW_ANGIOGENESIS_HOMO_SAPIENS) | 2.69E-09 | 47 | S1PR1, CDH5 |

F

G

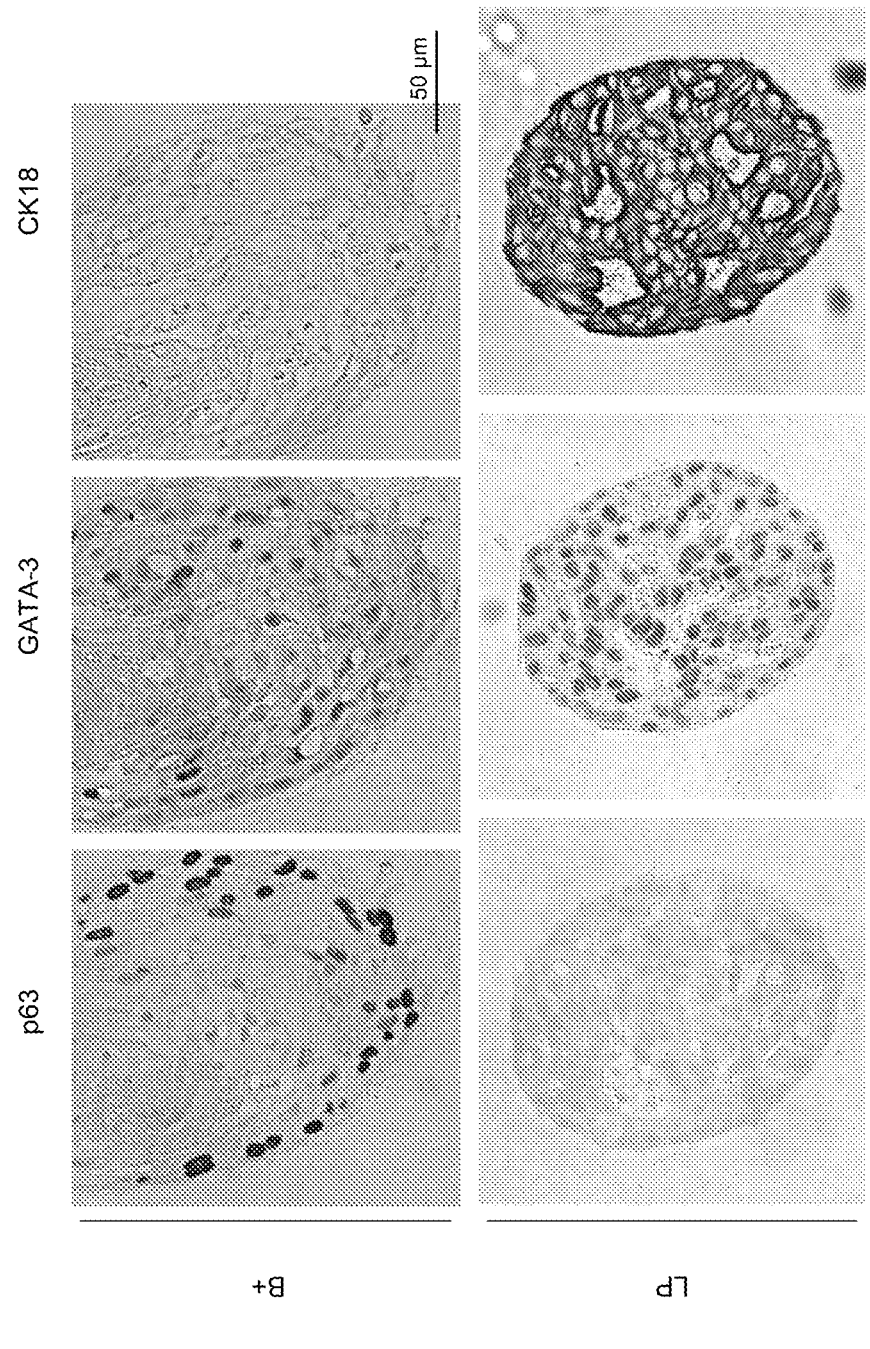

D

E

F

A

C

D

B

D

E

F c

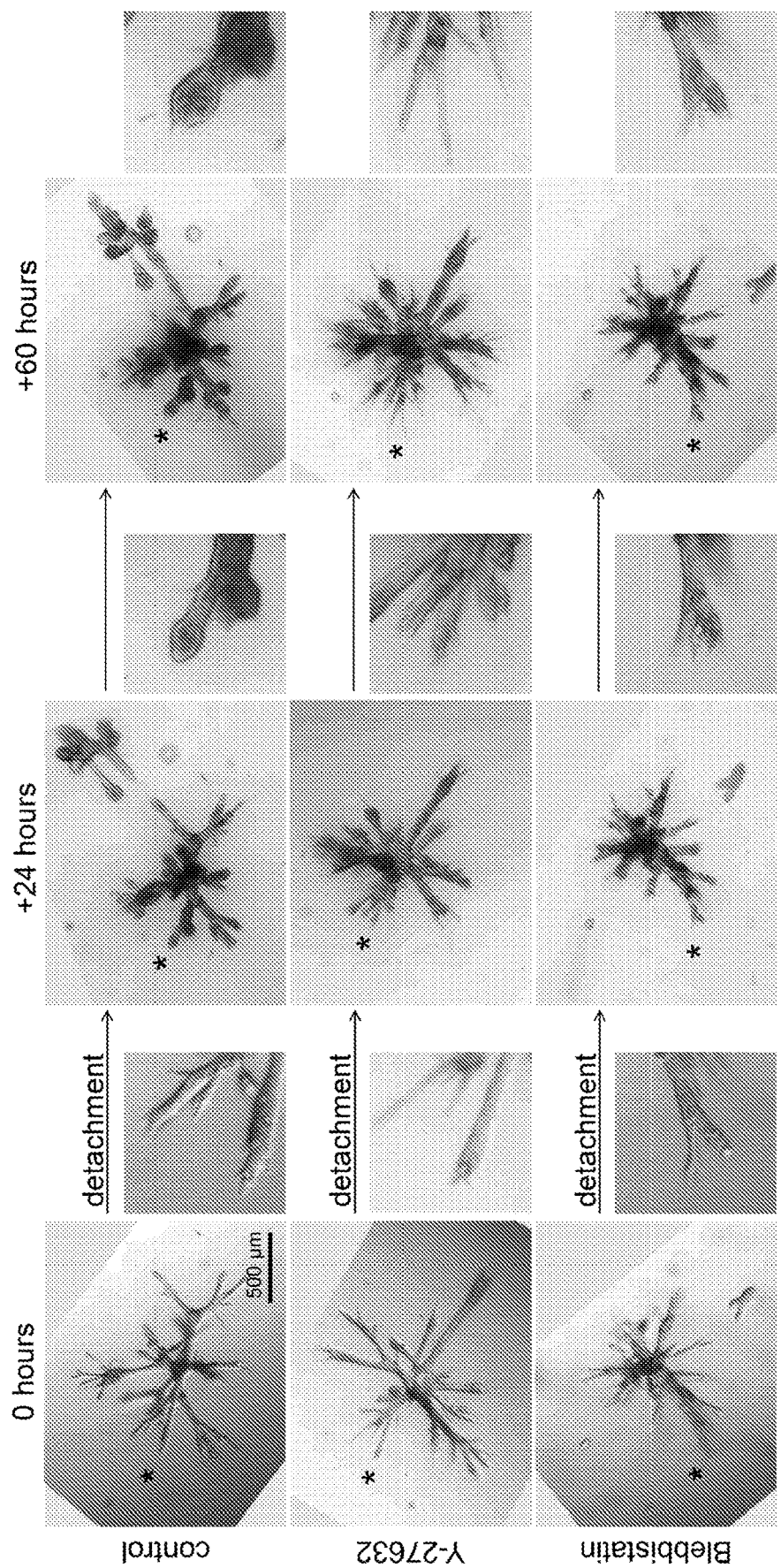

MEANS AND METHODS FOR GENERATION OF BREAST STEM CELLS

CROSS REFERENCE TO RELATED APPLICATIONS

This application claims priority to International Application No. PCT/IB2016/052407, filed on Apr. 28, 2016, entitled MEANS AND METHODS FOR GENERATION OF BREAST STEM CELLS, which claims the benefit of International Application No. LU 92706, filed Apr. 30, 2015, the disclosures of which are incorporated herein by reference. Also the entire contents of the ASCII text file entitled "IPM0076US_Sequence_Listing.txt" created on Oct. 30, 2017, having a size of 5 kilobytes is incorporated herein by reference.

BACKGROUND

The present invention is in the field of stem cell biology, in particular in the field of developmental and regenerative biology. The invention generally relates to a method of generating cells capable of differentiating to a multicellular organoid unit that morphologically and/or functionally resembles the terminal ductal-lobular unit. More precisely, said cells are generated by dissociating mammary epithelial tissue, thereby gaining cells and culturing said cells in presence of a compound which elevates cAMP levels in a collagen gel. Under said culturing conditions said cells form a multicellular organoid unit facilitating to obtain a breast stem cell by isolating a single cell from said multicellular organoid unit. The present invention also relates to enriching said cells and differentiating them to a multicellular organoid that morphologically and/or functionally resembles the terminal ductal-lobular unit and use of said cells or said multicellular organoid in testing a compound. Furthermore, the present invention relates to a composition comprising said breast stem cells or the multicellular organoid.

The mammary gland (MG) is a compound tubulo-alveolar gland that is composed of a series of branched ducts that, during lactation, drain sac-like alveoli (lobules) and develops from the anlage, a cluster of specified cells derived from the ectoderm that form a rudimentary ductal tree before birth (Sternlicht, 2006, Breast Cancer Res. 8, 201). Puberty induces outgrowth into an expansive network of ducts, which drain the milk-producing units of the breast, called terminal ductal lobular units (TDLU, Brisken and O'Malley, 2010, Cold Spring Harb Perspect Biol 2, a003178). The extensive proliferation and remodeling during every menstrual cycle and pregnancy, and the ability of single murine mammary epithelial cells (MEC) to reconstitute a functional MG in transplantation assays, suggest the existence of adult mammary stem cells (MaSC, Brisken and Duss, 2007, Stem Cell Rev and Rep 3, 147-156; Fridriksdottir et al., 2011, Int. J. Dev. Biol. 55, 719-729; Visvader and Stingl, 2014, Genes Dev. 28, 1143-1158). However, presence and clonal output of these MaSC appear to depend on developmental stage (van Amerongen et al., 2012, Stem Cell 11, 387-400), and whether homeostasis or regeneration is required (Rios et al., 2014, Nature 1-19; Van Keymeulen et al., 2012, Nature 479, 189-193; Wang et al., 2014, Nature 517, 81-84), the latter being induced by transplantation assays (Shackleton et al., 2006, Nature 439, 84-88; Stingl et al., 2006, Nature 439, 993-997).

The mammary epithelium is composed of two lineages of epithelial cells: the luminal cells (which make milk during lactation) and basal positioned myoepithelial cells. Generation and maintenance of the mammary epithelium is via the MaSC. The MaSC is of interest to the breast cancer biologist since cancer theory suggests that it is the stem cell, and possibly some of its more immediate descendants that have decreased stem cell potential but still have proliferative potential that are the targets for malignant transformation. As well, recent publications in the literature demonstrate that malignancies themselves have a stem cell component that propagates the tumor (Al-Hajj et al., Proc Natl Acad Sci USA. 2003; 100:3983-8). This has huge implications in the treatment of cancer since it suggests that in order for cancer to be successfully contained or eradicated, it is the tumor stem cell component that has to be the therapeutic target. The ability to identify and purify mammary stem cells would be invaluable to the study of breast cancer.

Breast cancer is the most common malignancy to affect women, accounting for approximately one quarter of all female cancers. Despite a significant improvement in the management of breast cancer over the last few years, about 25% of women diagnosed will die from the disease, revealing that those tumor cells have intrinsic properties that are refractory to current treatment strategies. The heterogeneous nature of breast cancer suggests the involvement of multiple genetic factors and cell types but these are poorly understood.

A prerequisite to understanding breast oncogenesis is the study of the regulation of normal breast epithelial development.

Consequently, defining the molecular identity of MaSC and their precise contribution to different stages of MG development and maintenance remains an active area of investigation. Moreover, elucidation of mechanisms that govern regenerative potential is crucial not only for understanding normal MG biology, but also for tissue engineering approaches (Nigam, 2013, Stem Cells Transl Med 2, 993-1000) and cancer research, where such pathways are dysregulated (Magee et al., 2012, Cancer Cell 21, 283-296).

Importantly, significant differences in cellular and matrix composition between the mouse and human mammary stroma hamper assessment of human MaSC-activity in the mouse (Parmar and Cunha, 2004, Endocrine Related Cancer 11, 437-458). Limited in vivo growth of human mammary epithelial cells (HMEC) has been achieved by humanization of the mouse fat pad (Proia and Kuperwasser, 2006, Nat Protoc 1, 206-214) or transplantation under the renal capsule (Eirew et al., 2008, Nat. Med. 14, 1384-1389). Alternatively, MaSC potential of HMEC has been assessed in vitro, but relied on previously cultured cells, established cell lines and support from non-mammary gland derived stromal cells (Dontu et al., 2003, Genes Dev. 17, 1253-1270; Eirew et al., 2008, Nat. Med. 14, 1384-1389; Gudjonsson et al., 2002, Genes Dev. 16, 693-706; Stingl et al., 2005, Methods Mol. Biol. 290, 249-263). However, up to now people have failed to get hands on isolated human MaSCs.

The above being said, breast (cancer) cell lines are not a suitable equivalent for studying breast stem cells, since such cell lines do not behave as primary stem cells. Moreover, up to now and to the best knowledge breast stem cells have not been made technically available though there is a high demand for them.

In sum, attempts of the prior art to provide primary mammary, in particular human epithelial cells have the following disadvantages: no recapitulation of branching morphogenesis with generation of secondary and tertiary branches (lack of physiological relevance), use of cell lines and non-physiological stroma and matrix in culture conditions, no direct functional readout for stem cells, no quantification of stem cell function and no readout for de-differentiation of luminal progenitors, the latter are believed to be cells-of-origin for breast cancer.

Consequently, there is an unsatisfied need, for making available and thus providing a substantially homogenous population of MaSCs from a source of freshly isolated (i.e. primary) human mammary gland tissue and recapitulating mammary gland development, homeostasis and disease-development.

The present invention meets this need by providing an organoid assay that enables quantification of regenerative potential at the single-cell level in freshly isolated HMEC populations, isolation of human MaSCs from primary mammary gland tissue and generation of multicellular organoid units that morphologically and/or functionally resembles the terminal ductal-lobular unit. As such, the present invention achieved a breakthrough in providing cells which are capable of differentiating to a multicellular organoid that morphologically and/or functionally resembles the terminal ductal-lobular unit which is the functional unit of the mammary gland. Such cells have not been provided before the present invention and thus pave the way for assessing the regenerative potential of such cells, influence of compounds of interest on such cells as well as interaction with the physical environment of these cells. This achievement became possible, since the present inventors recognized functional tests which allow them to identify and specifically excerpt these cells from primary tissue. Therefore, single cells dissociated from mammalian epithelial tissue are cultivated and screened for their ability to generate multicellular TDLU-like structures. Cells that exhibit the ability to do are thought to have regenerative stem-cell potential and are hence designated "breast stem cells". In addition, the present inventors also identified a combination of surface markers described in detail herein, which allows them to enrich such cells which may then be further investigated by means of the functional tests described herein in detail. Finally, the present inventors also identified a population of cells by making use of another specific combination of cell surface markers. These cells are luminal progenitor cells. They offer the possibility of investigating cellular responses, in particular induction or inhibition of differentiation and for identifying spontaneous de-differentiation. Specifically, without being bound by theory, de-differentiation of luminal progenitor cells to a multicellular organoid unit that morphologically and/or functionally resembles the terminal ductal-lobular unit, which is otherwise formed by the breast stem cells provided herein, is indicative of cancerogenesis. Hence, the luminal progenitor cells provided herein provide preferably a tool for, inter alia, testing compounds for their potential to cause such cells to de-differentiate.

The present inventors developed an organoid assay where single, freshly isolated HMEC, cultured in collagen gels, generate organoids that resemble TDLU. The TDLU-like organoids comprise ductal structures and/or multiple branch-points and/or alveolar buds. They express multi-lineage markers at correct positions and/or display contractility, which is deemed to be required for alveologenesis. Remarkably, an increase in matrix compliance by switching collagen gels from an adherent, rigid state to free floatation suffices to trigger alveologenesis, emphasizing the importance of physical parameters in directing differentiation of the MG (Bainer and Weaver, 2013, Science 341, 965-966; Schedin and Keely, 2011, Cold Spring Harb Perspect Biol 3, a003228-a003228). Importantly, TDLU are considered the functional unit of the breast, as they contain most of the cells that proliferate in response to hormones during the menstrual cycle, pregnancy and lactation (Anderson et al., 1998, J Mammary Gland Biol Neoplasia 3, 23-35). Therefore, the present inventors reasoned that generation of TDLU-like structures represents a suitable readout for regenerative capacity of HMEC. In line with the assumption that MaSC reside in the basal subpopulation, the present inventors determined that TDLU-like structure formation is enriched in the $CD49f^{hi}$/EpCAM$^-$ population, commonly referred to as basal. However, by performing extreme limiting dilution analysis (ELDA), the membrane metallo-endopeptidase CD10 was identified as a marker to enrich for TDLU-like structure-forming cells and reveal the presence of heterogeneous stromal cells within the $CD49f^{hi}$/EpCAM$^-$ population. Together, these data highlight the diversity and plasticity of cell populations in the normal human MG while revealing remarkable robustness of functional and phenotypic qualities in isolated subpopulations, regardless of age and parity of donor tissue.

To this end, the chemically and physically defined in vitro assay system of the present invention will be particularly useful: stromal components can be added for co-culture studies. Moreover, HMEC with distinct genetic backgrounds can be tested for changes in their regenerative potential. Finally, the assay enables quantification of regenerative capacity by ELDA and/or systematic investigation of mechanotransduction at distinct steps of morphogenesis.

It must be noted that as used herein, the singular forms "a", "an", and "the", include plural references unless the context clearly indicates otherwise. Thus, for example, reference to "an expression cassette" includes one or more of the expression cassettes disclosed herein and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

The term "about" or "approximately" as used herein means within 20%, preferably within 10%, and more preferably within 5% of a given value or range. It includes also the concrete number, e.g., about 20 includes 20.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well-known in the art. Generally, nomenclatures used in connection with techniques of biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well-known in the art and as described in various general and more specific references that are cited and discussed throughout the present specification unless otherwise indicated. See, e. g., Sambrook et al., Molecular Cloning: A Laboratory Manual, 3rd ed., Cold Spring Harbor Laboratory Press, Cold Spring Harbor, N.Y. (2001); Ausubel et al., Current Protocols in Molecular Biology, J, Greene Publishing Associates (1992, and Supplements to 2002); Handbook of Biochemistry: Section A Proteins, Vol I 1976 CRC Press; Handbook of Biochemistry: Section A Proteins, Vol II 1976 CRC Press. The nomenclatures used in connection with, and the laboratory procedures and techniques of, molecular and cellular biology, protein biochemistry, enzymology and medicinal and pharmaceutical chemistry described herein are those well-known and commonly used in the art.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

SUMMARY

The invention generally relates to a method of generating cells capable of differentiating to a multicellular organoid unit that morphologically and/or functionally resembles the terminal ductal-lobular unit. According to the inventive method, said cells are generated by dissociating healthy or diseased mammary epithelial tissue, thereby gaining cells and culturing said cells in the presence of a compound which elevates cAMP levels in a collagen gel for at least 7 days. The collagen gel can be a collagen-I gel that is attached or free-floating. The compound that elevates cAMP levels can be an adenylylcyclase agonist, such as Forskolin. Under said culturing conditions said cells form a multicellular organoid unit facilitating to obtain a breast stem cell by isolating a single cell from said multicellular organoid unit. The culture medium may also comprise a ROCK inhibitor such as Y-27632 or Thiazovivin. Determination of whether a multicellular organoid unit is formed is envisaged to involve assessing the presence of ductal structures and multiple branch-points and/or alveoli. The method may also comprise a step of determining the capability of the multicellular organoid unit to contract a floating collagen gel, which may be indicative of alveologenesis. It is envisaged that the multicellular organoid unit can be responsive to hormones and/or growth factors. The present invention also relates to enriching cells from mammary epithelial tissue and differentiating them to a multicellular organoid that morphologically and/or functionally resembles the terminal ductal-lobular unit and use of said cells and said multicellular organoid in testing a compound. The cells can be enriched by sorting them for the surface marker combination $CD31^-$, $CD45^-$, $EpCAM^-$, $CD49f^+$ and $CD10^+$. Enrichment of cells can also be accomplished by determining their capability to form a multicellular organoid unit in a collagen gel in the presence of a compound that elevates cAMP levels after at least 7 days and/or determining whether the multicellular organoid unit is capable of contracting a floating collagen-I gel. Furthermore, the present invention relates to a composition comprising said cells or the multicellular organoid. Such cells which are capable of differentiating to a multicellular organoid unit that morphologically and/or functionally resembles the terminal ductal-lobular unit are preferably breast stem cells, preferably human breast stem cells.

FIGURE LEGENDS

FIG. 1. Identification of culture conditions that promote generation of TDLU-like structures by freshly dissociated HMEC (A) Experimental setup: generation of floating collagen gels.
(B) Bright-field microscopy: Carmine-stained representative images of different types of branched and non-branched structures (donor M8). Scale bar: 200 µm.
(C) Bright-field microscopy: haematoxylin-eosin stained section of a terminal ductal lobular unit (TDLU) from a healthy woman. Scale bar: 100 µm.
(D) Improvement of culture conditions: effect of one-time treatment with 3 µM Y-27632 at day 0 of culture and continuous treatment with 10 µM Forskolin on the generation of branched-type structures in floating collagen I gels at day 14 of culture. Star-like structures were not detected and therefore excluded from quantification. n=3 gels/condition. Structure formation per 100 seeded cells is shown (donor M8).
(E) Quantification of monoclonal and polyclonal structures formed by eGFP, mCherry and unlabeled passage 1 cells in floating collagen I gels (Donor M5). 500, 1500 and 13500 cells were seeded per well (24-well plate) and 3, 6 and 8 eGFP/mCherry positive structures among 17, 18 and 12 unlabeled structures were analyzed, respectively. Monoclonal: complete structure eGFP or mCherry positive. Polyclonal: eGFP/mCherry positive and negative areas.
(F) Confocal microscopy: representative images of monoclonal and polyclonal structures (refer to E). Scale bar: 100 µm.
Data are shown as mean±standard deviation (SD).

Figure 2:
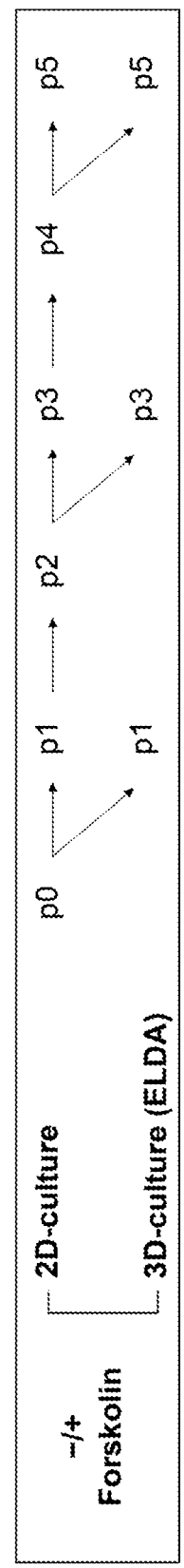
Figure 2:
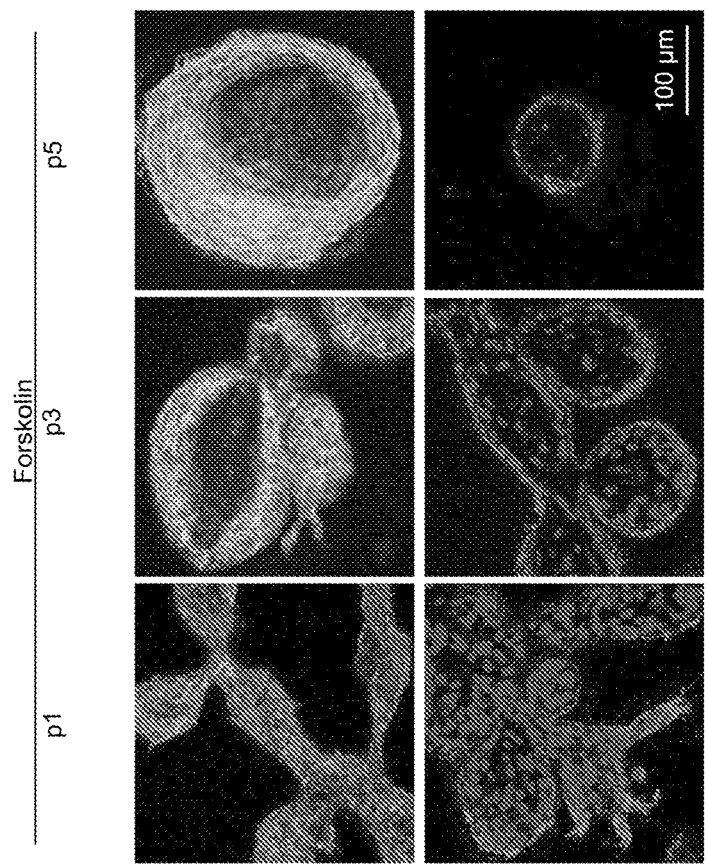
Figure 2:
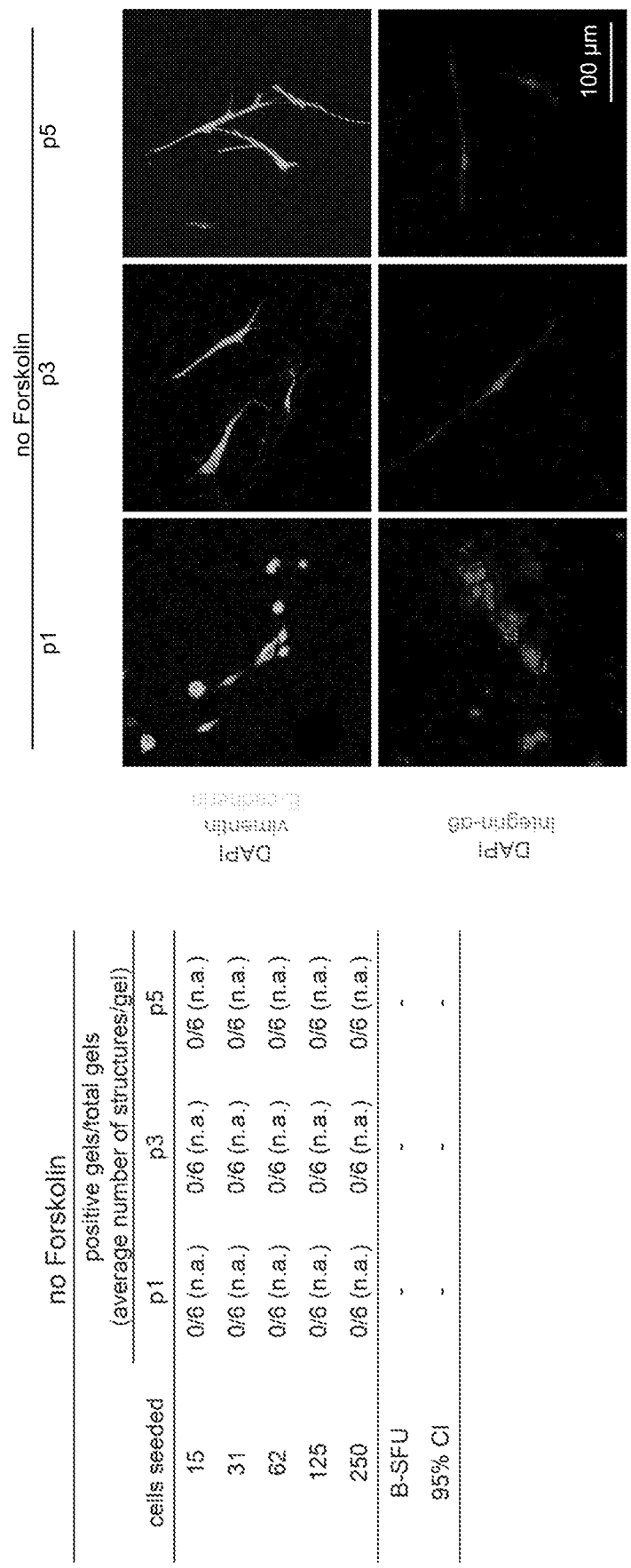

FIG. 2. Maintenance and expansion of TDLU-like structure formation during passaging and 2D-culture
(A) Experimental setup: freshly isolated HMEC (Donor M4) were cultured in 2D in the absence or presence of 10 µM Forskolin for 5 passages, and transferred to floating collagen I gels in limiting dilution at passage (p) 1, 3 and 5.
(B) Extreme limiting dilution analysis (ELDA): determination of Branched Structure-Forming Units (B-SFU) of cells cultured in the presence of Forskolin (donor M4).
(C) Confocal microscopy: representative TDLU-like structures generated in floating collagen I gels after 2D-culture in the presence of Forskolin (refer to A). Vimentin (red), E-cadherin (green), integrin-α6 (red), DAPI for cell nuclei (blue). Scale bar: 100 µm.
(D) ELDA: determination of B-SFU of cells cultured without Forskolin (donor M4).
(E) Confocal microscopy: representative clusters of cells generated in floating collagen I gels after 2D-culture without Forskolin, and transferred to floating collagen I gels at passage 1, 3 and 5 (refer to A). Vimentin (red), E-cadherin (green), integrin-α6 (red), DAPI for cell nuclei (blue). Scale bar: 100 µm.
Data are shown as mean and 95% confidence intervals (CI).

Figure 3A:
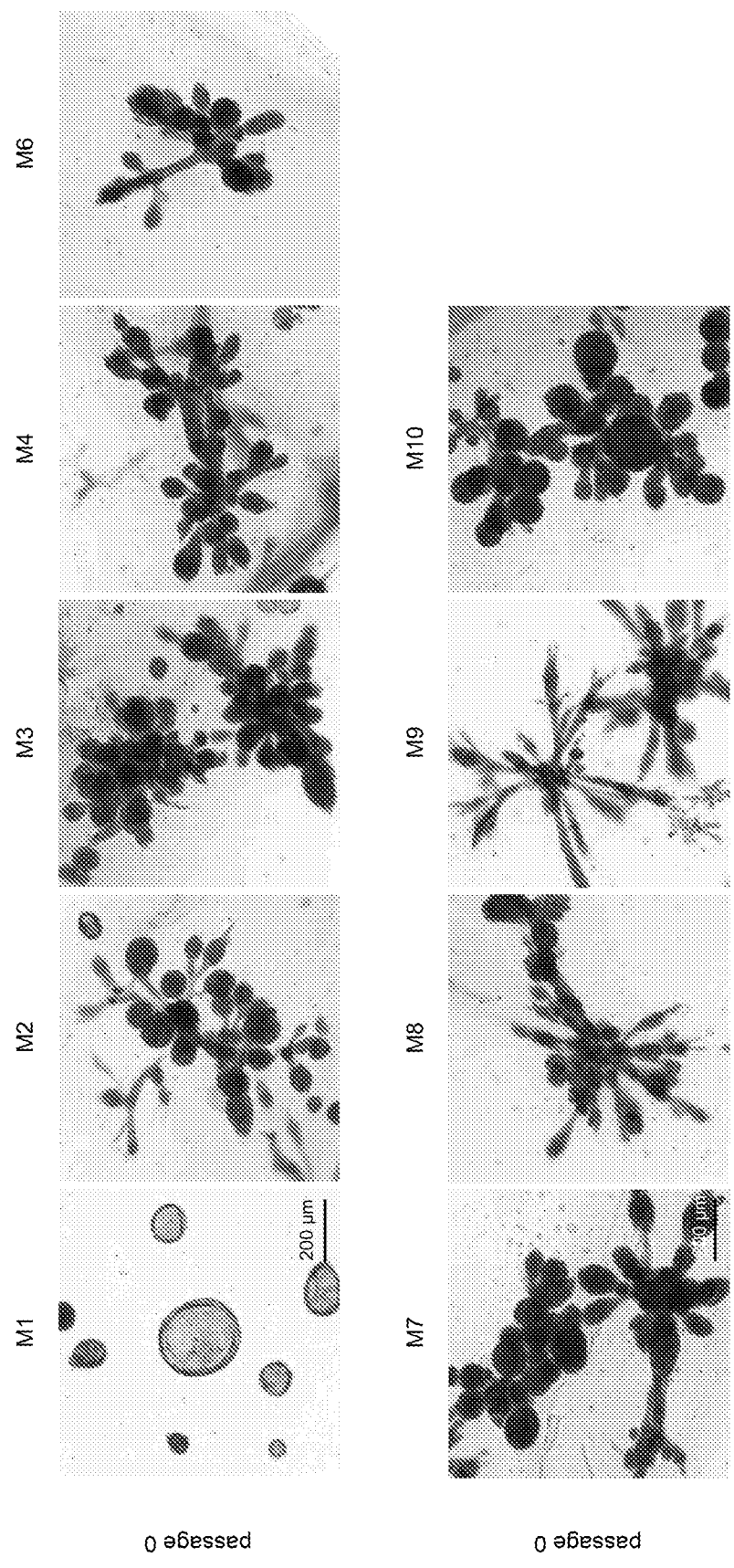
Figure 3:
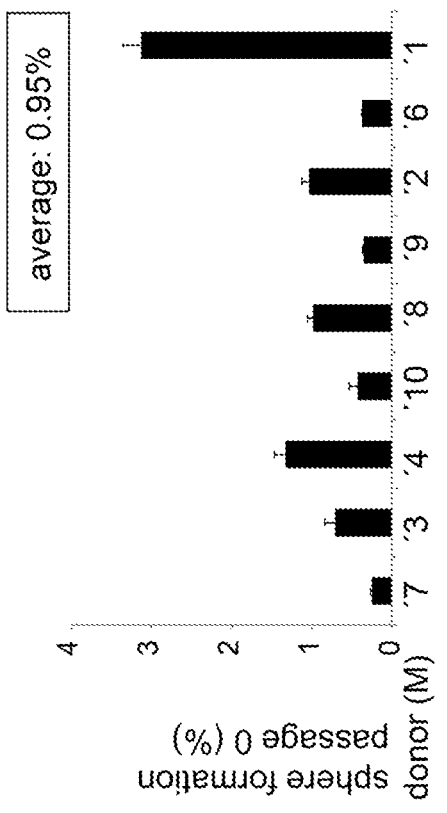
Figure 3:
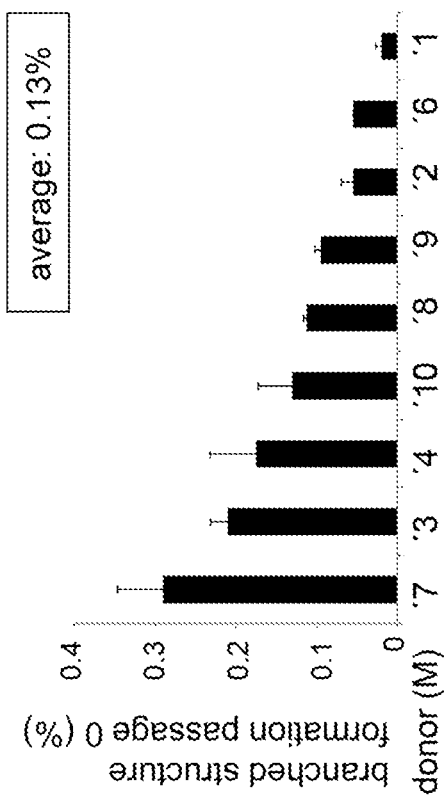
Figure 3:
Figure 3:
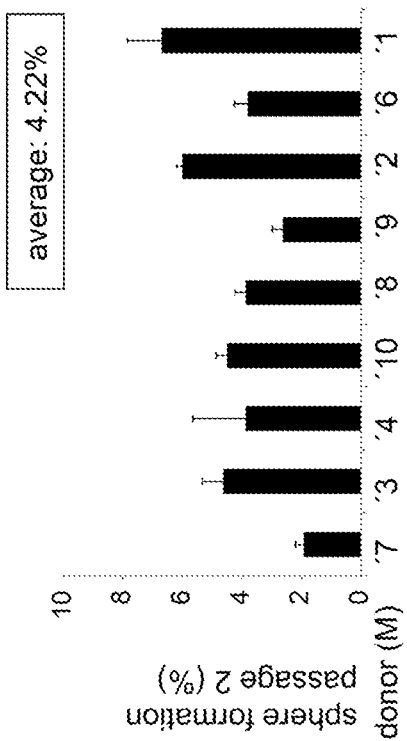
Figure 3:
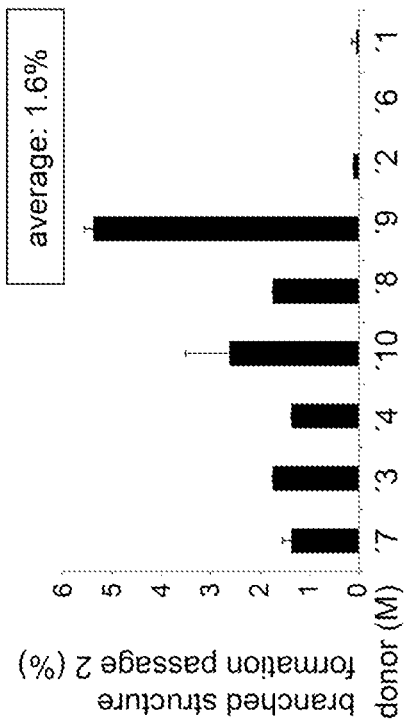

FIG. 3. Frequency of TDLU-like structure-forming cells varies between donors and is increased by 2D-culture
(A) Bright-field microscopy: Carmine-stained representative images of TDLU-like structures from freshly isolated cells of 9 donors (M1-M4, M6-M10) in floating collagen I gels. Scale bar: 200 µm.
(B) TDLU-like structure formation per 100 seeded HMEC from freshly isolated cells of 9 donors at day 9 of culture. n=2. Data are shown as mean±standard deviation (SD).
(C) Sphere formation per 100 seeded HMEC from freshly isolated cells of 9 donors (refer to A) at day 9 of culture. n=2 gels/donor. Data are shown as mean±standard deviation (SD).
(D) Extreme limiting dilution analysis (ELDA): determination of Sphere and Branched Structure-Forming Units (S-SFU and B-SFU) of HMEC in floating collagen I gels at passage 0 (Donor M8). Data are shown as mean and 95% confidence intervals (CI).
(E) Bright-field microscopy: Carmine-stained representative images of TDLU-like structures from cells of 9 donors (M1-4, M6-M10) cultured in 2D for 12 days prior transfer to floating collagen I gels. Scale bar: 200 µm.
(F) TDLU-like structure formation per 100 seeded HMEC from cells of 9 donors established in 2D-culture (refer to E) at day 9 of culture. n=2 gels/donor. Data are shown as mean±standard deviation (SD).
(G) Sphere formation per 100 seeded HMEC from cells of 9 donors established in 20-culture at day 9 of culture. n=2 gels/donor. Data are shown as mean±standard deviation (SD).
(H) Analysis of viability by Fluorescence-Activated Cell Sorting (FACS), using 7-AAD: n=10 donors (M1-M10). Data are shown as mean±standard deviation (SD).

Figure 4:
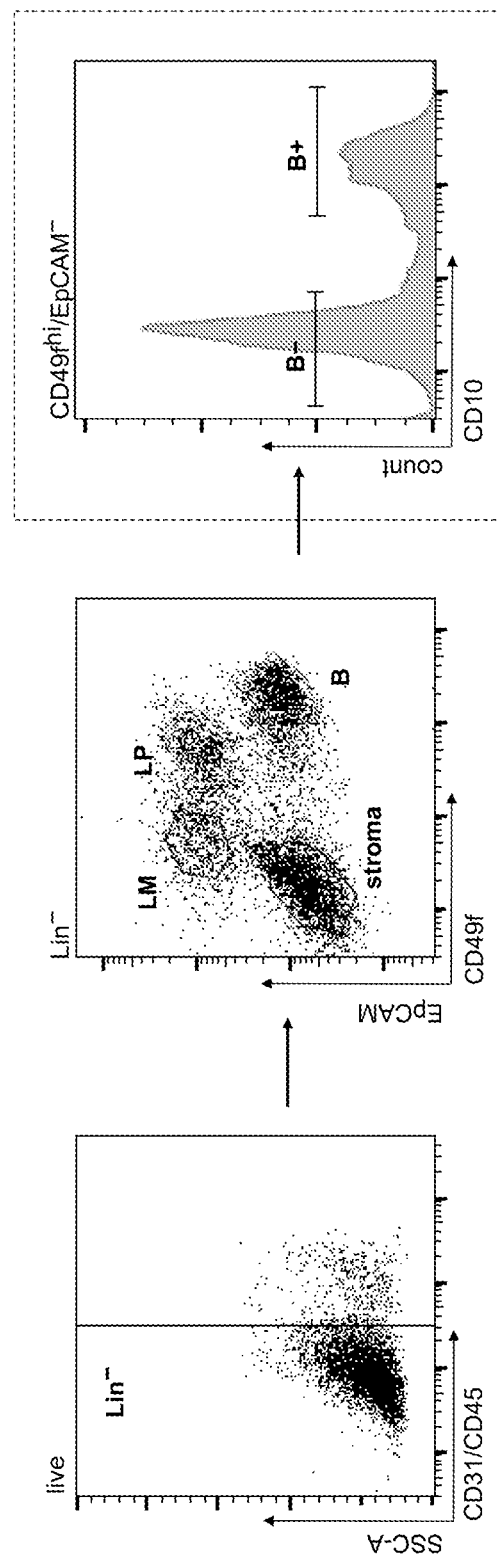
Figure 4:
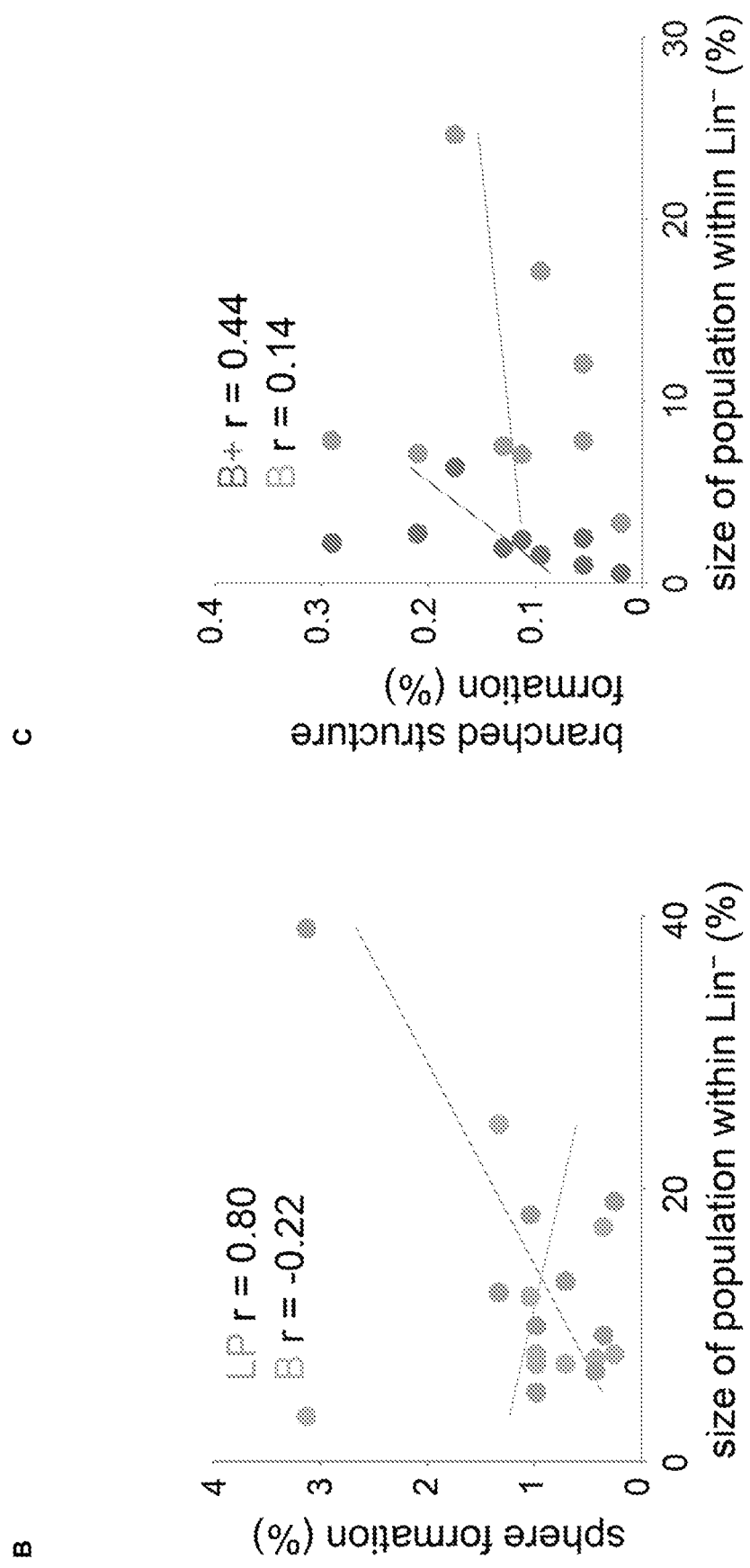
Figure 4:
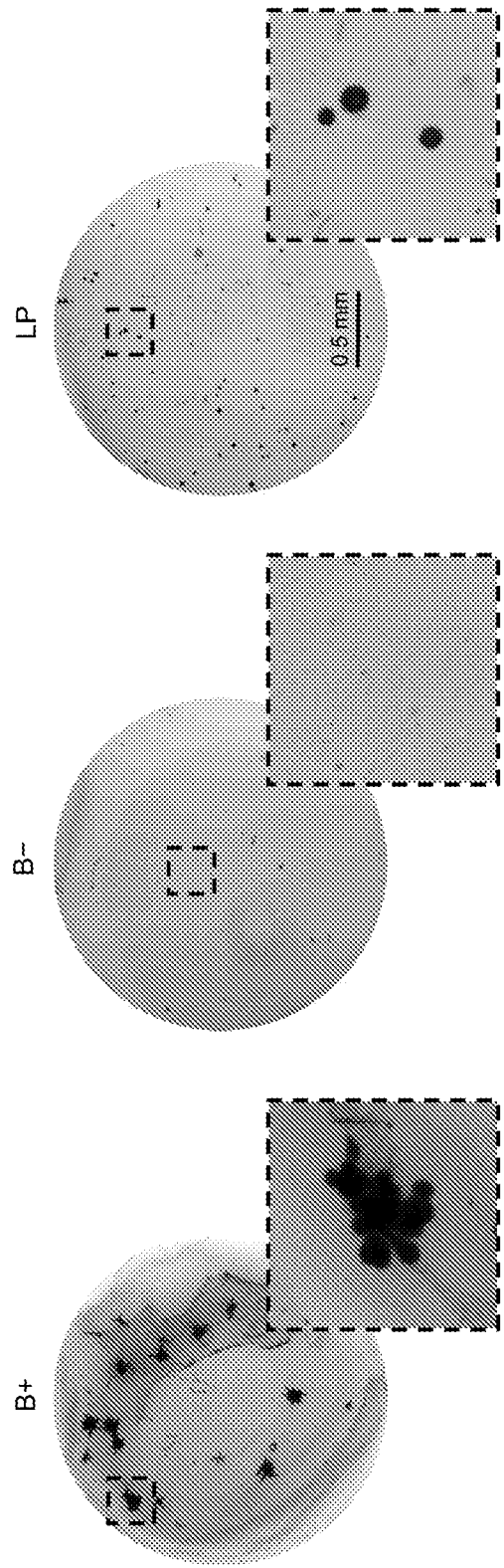

FIG. 4. TDLU-like structure-forming potential is contained within a CD10$^+$/CD49f$^{hi}$/EpCAM$^-$ basal population
(A) Fluorescence Activated Cell Sorting (FACS) of freshly isolated HMEC: dead cells were excluded (7AAD$^-$=live), hematopoietic and endothelial cells were excluded (CD45$^-$/CD31$^-$=Lin$^-$), EpCAM, and CD49f were used to depict the following populations: Stroma (CD49f$^-$/EpCAM$^-$), Luminal mature (LM, CD49f$^-$/EpCAM$^+$), Luminal progenitors (LP, CD49f$^+$/EpCAM$^+$), Basal (B, CD49f$^{hi}$/EpCAM$^-$). LP and B populations were isolated. The B population was further subdivided into B− (CD10$^-$/CD49f$^{hi}$/EpCAM$^-$) and B+ (CD10$^+$/CD49f$^{hi}$/EpCAM$^-$).
(B) Linear correlation between sphere formation (per 100 freshly isolated HMEC) and the size of the LP within Lin$^-$ population (blue dots), or the size of the B population (pink dots). One dot represents one donor. r=correlation co-efficient.
(C) Linear correlation between TDLU-like structure formation (per 100 freshly isolated HMEC) and the size of the B+ within Lin$^-$ population (red dots) or the B population (pink dots). One dot represents one donor. r=correlation co-efficient.
(D) Bright-field Microscopy: Carmine-stained representative whole collagen I gels containing B+, B− or LP cells (Donor M3). Scale bar: 0.5 mm.
(E) Extreme limiting dilution analysis (ELDA): determination of Branched Structure-Forming Units (B-SFUs) of 4 populations (B+, B−, B, LP) of freshly isolated HMEC (Donors M8, M9, M10) sorted by FACS according to (A) prior cultivation in floating collagen I gels. Data are shown as mean and 95% confidence intervals (CI).

Figure 5:
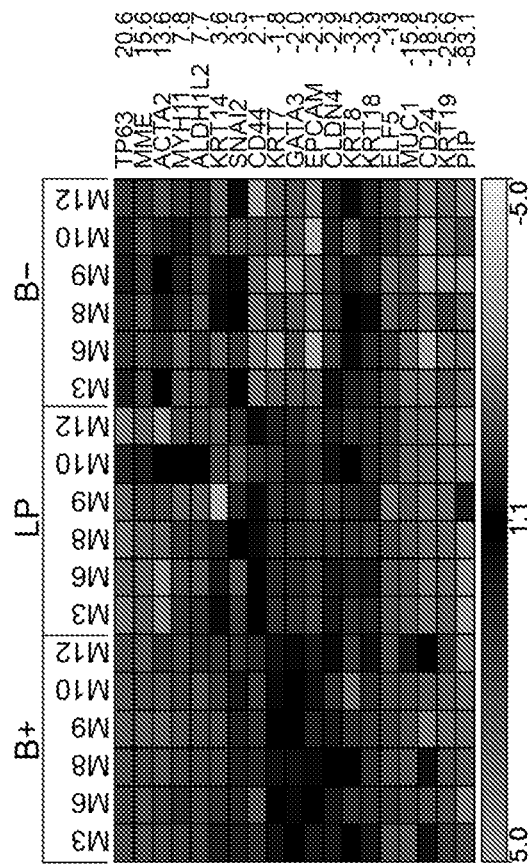
Figure 5:
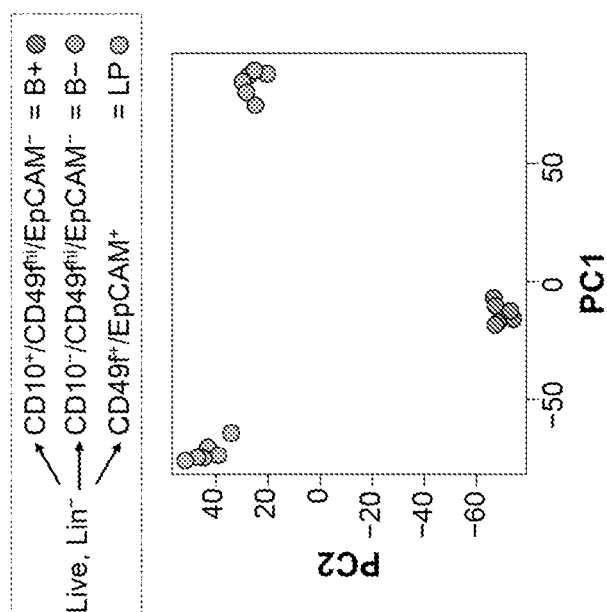
Figure 5:
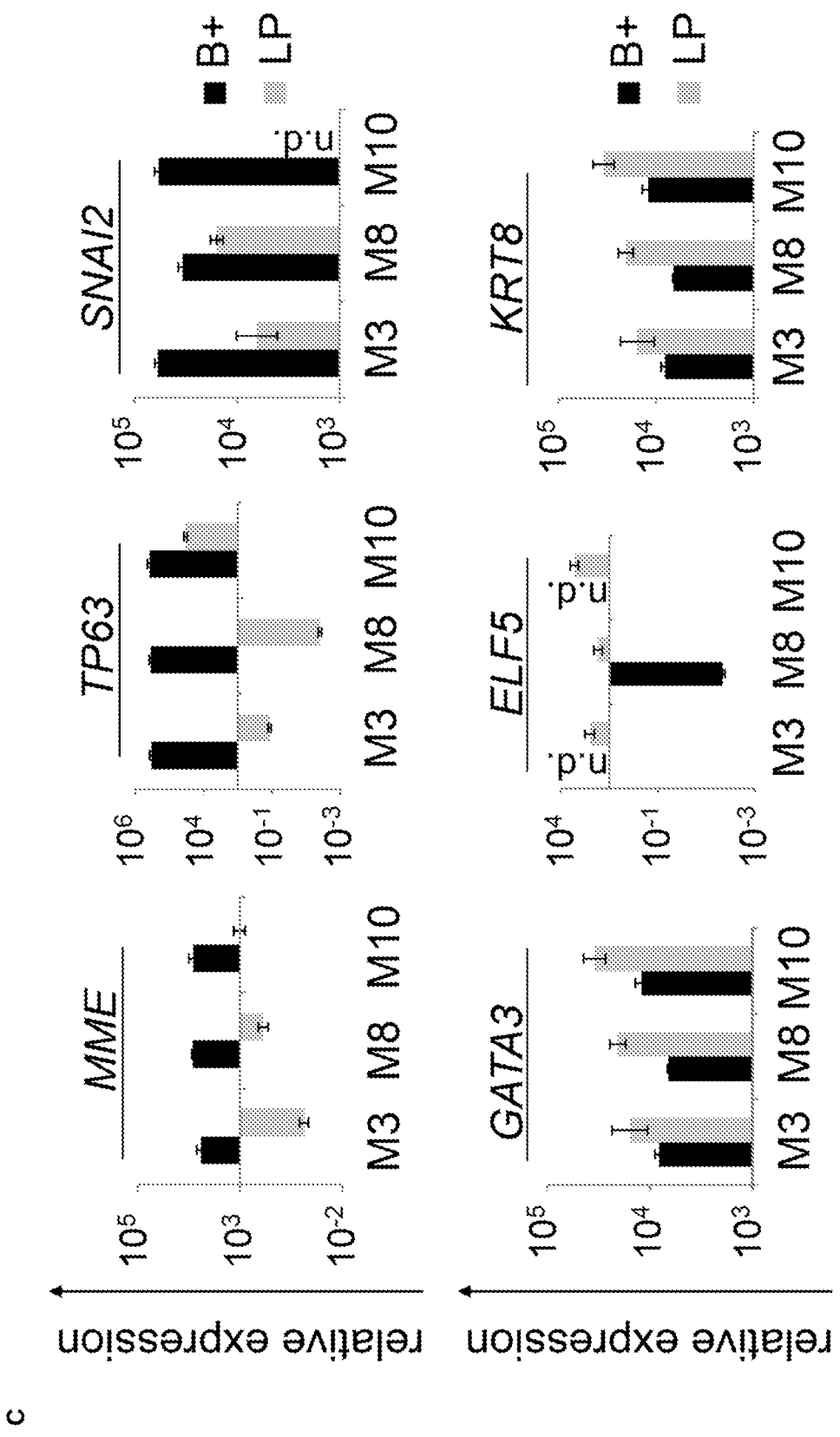
Figure 5:
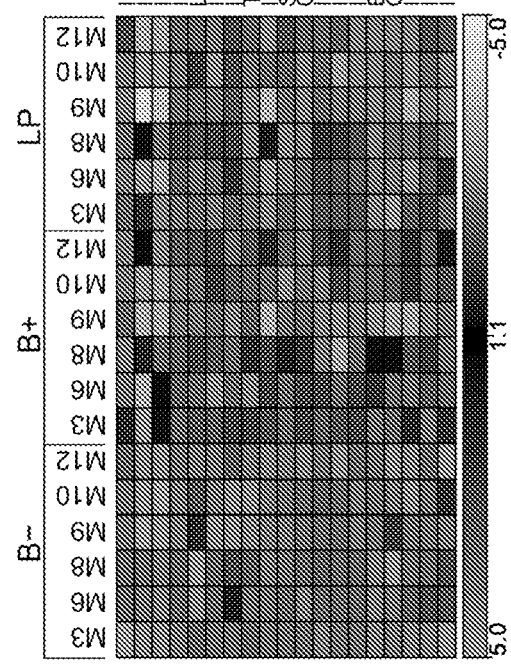
Figure 5:
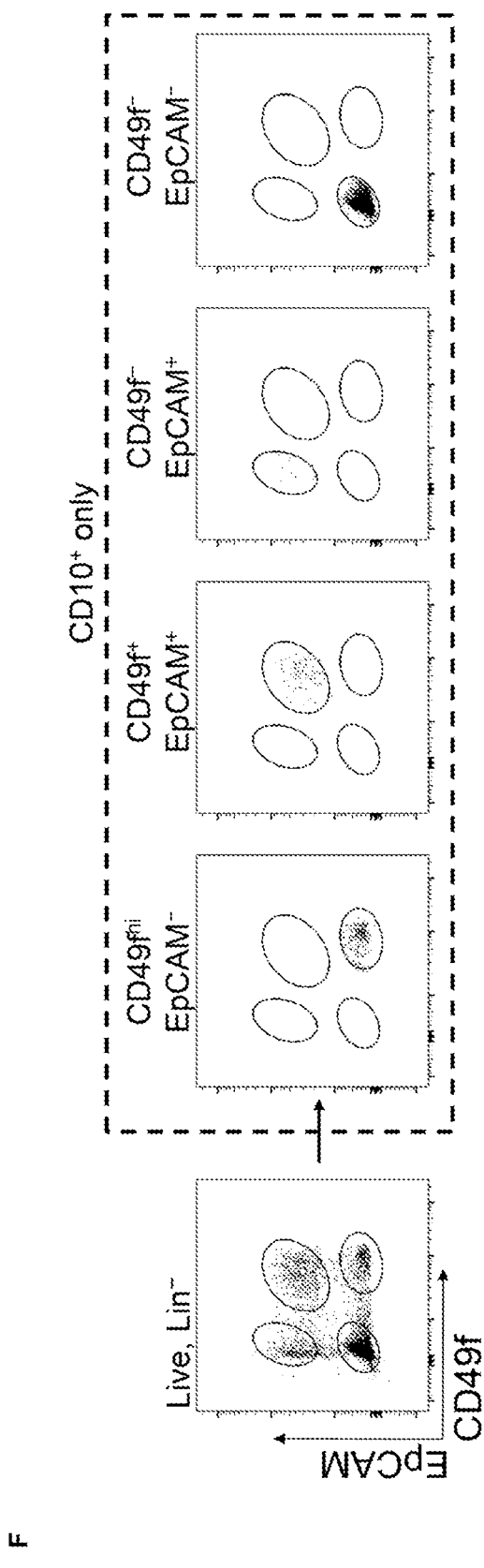
Figure 5:
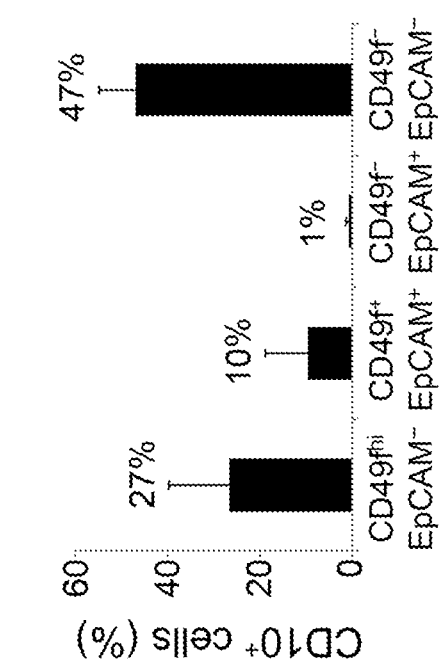

FIG. 5. CD10-staining reveals a stromal component within the CD49f$^{hi}$/EpCAM$^-$ population
(A) Gene expression profiling: RNA for microarray analysis was derived from 3 subpopulations (B+, B− and LP, as indicated) purified by FACS using freshly isolated HMEC from 6 donors (M3, M6, M8, M9, M10, M12). Following unsupervised clustering of all samples, Principal Component Analysis (PCA) was conducted.
(B) Heatmap: shown are the expression values of up- and downregulated luminal and basal signature genes in all samples. Fold change was derived by comparing B+ versus LP expression levels. Red (high) and blue (low) indicates log 2 expression values. Scale bar in log 2.
RT-PCR: MME/CD10, TP63, SNAl2, GATA3, ELF5, KRT8 mRNA expression in B+ and LP cells from 3 donors (M3, M8, M10). n.d., not detectable, n=3.
(C) Heatmap: shown are the expression values of the top-20 significantly (FDR<10%) upregulated genes in B− samples versus B+ samples with corresponding fold changes. Red (high) and blue (low) indicates log 2 expression values. Scale bar in log 2.
(D) GO term analyses: shown are selected significantly enriched terms (p<0.01) associated with genes differentially regulated between B− and B+ populations (FDR<10%, FC>3×). Shown are gene symbols of the top-20 genes from (D).
(E) Representative flow cytometry analysis showing the fraction of CD10$^+$ cells within the four populations defined by CD49f/EpCAM.
(F) Quantification of the percentage of CD10$^+$ cells within the different EpCAM/CD49f populations as in (F). Average of 10 donors (M1-M10).
Data are shown as mean±standard deviation (SD).

Figure 6:
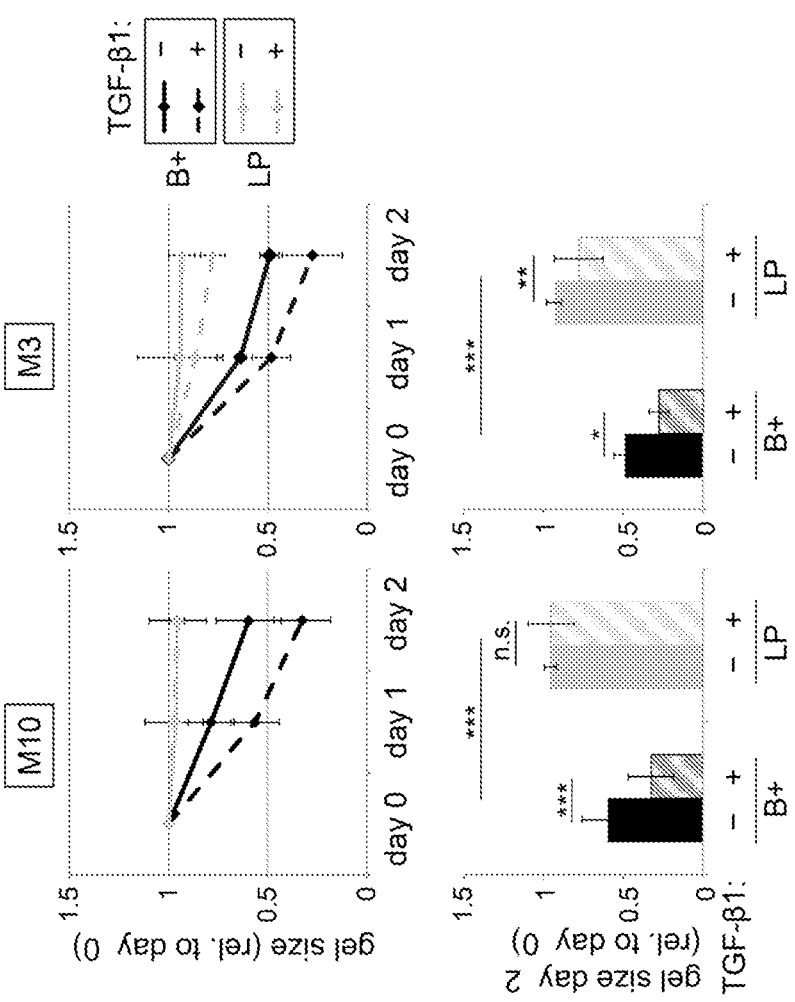
Figure 6:
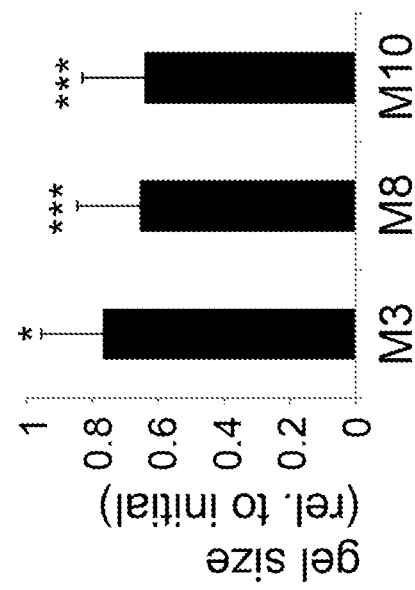
Figure 6:
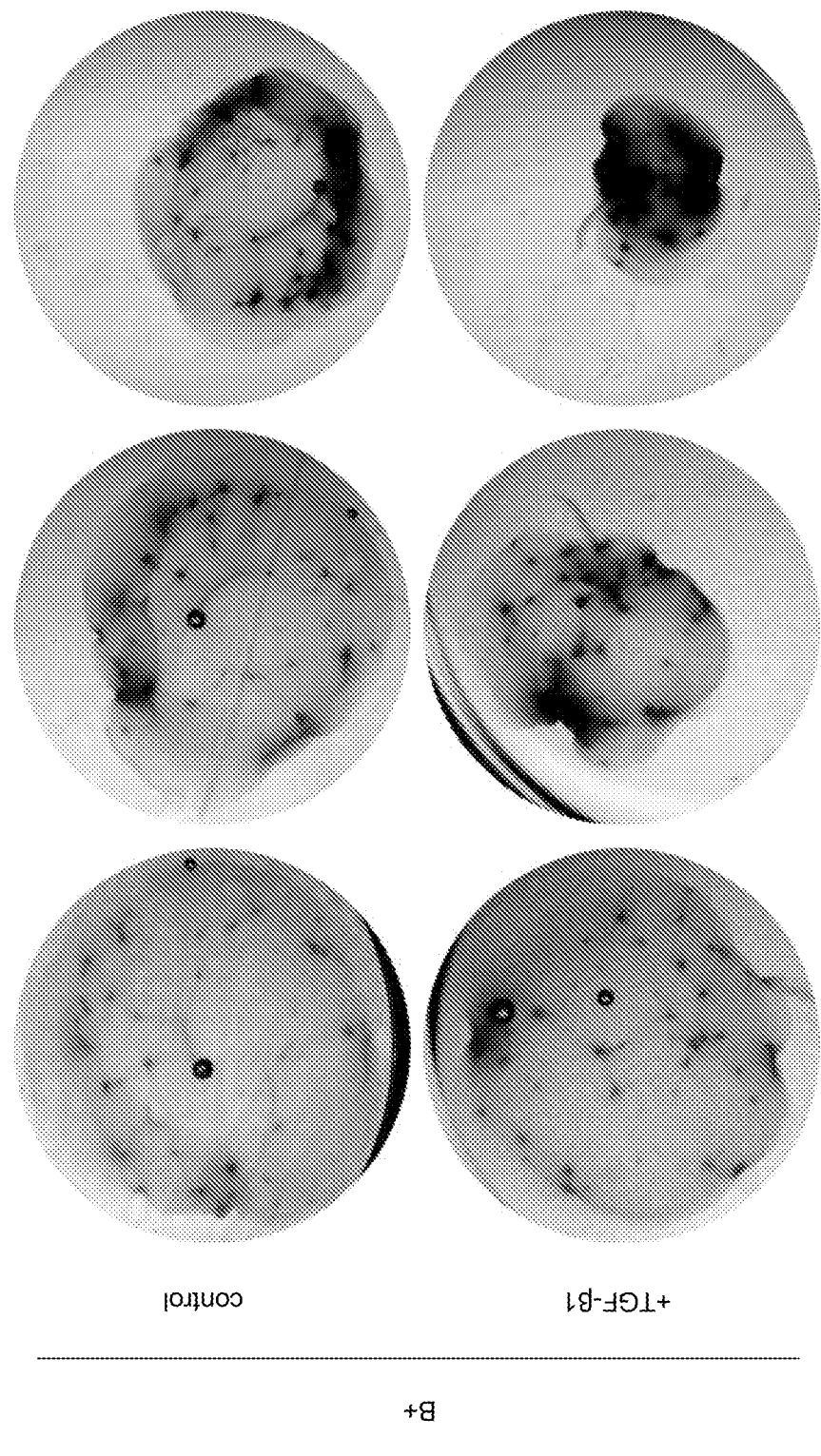
Figure 6:
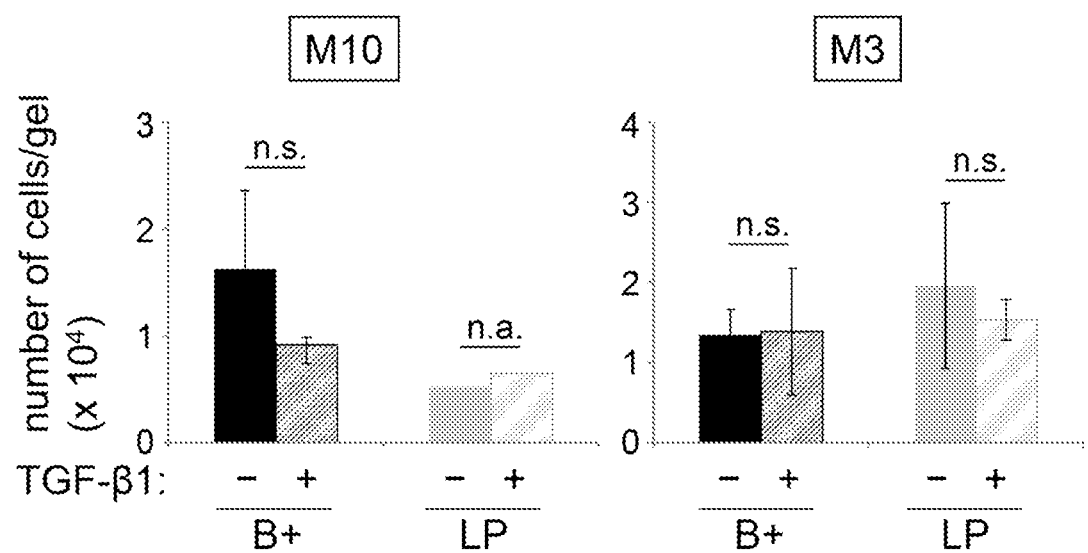
Figure 6:
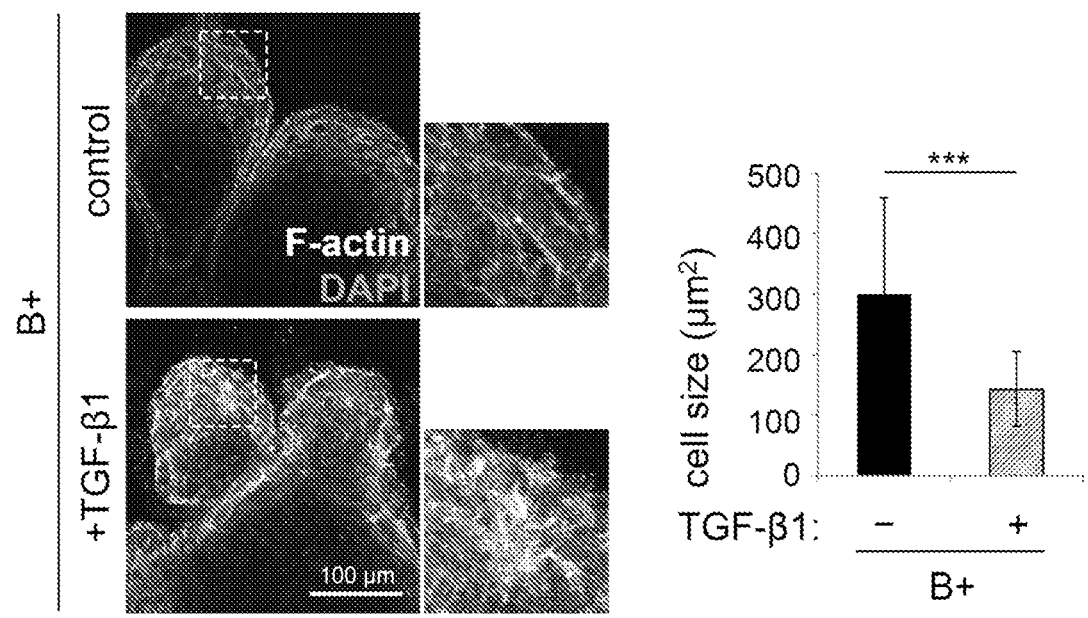

FIG. 6. TDLU-like structures derived from B+ cells recapitulate functional aspects of the mammary gland
(A) Immunohistochemistry: expression of p63, GATA-3 and CK18 in representative sections of structures derived from LP or B+ cells (Donor M10), fixed at culture day 20. For LP and B+, 6 and 5 fields of view were analyzed, respectively. Scale bar: 50 µm.
(B) Quantification of the size of floating collagen I gels containing HMEC (Donors M3, M8, M10). Gel size at day 13 (M3), day 14 (M8) and day 15 (M10) of culture is given as percentage of day 0. n=6 gels (M3, M10), n=9 gels (M8).
(C) Contraction of collagen I gels: Size of floating collagen I gels containing LP or B+ cells (Donors M3, M10) was determined at day 12 of culture (indicated as day 0), and imaged for two more days. Gel size is plotted relative to day 0. Half of the gels were treated with 2.0 ng/ml TGF-β1 once at day 0. Lower panel: Bar graphs of gel size at day 2 as percentage of day 0. n=12 gels/condition.
(D) Bright-field microscopy: Representative images of control and TGF-β1 treated gels containing B+ cells from (C) (Donor M10).
(E) Quantification of the average number of cells per gel at the end of analysis shown in (C). Gels containing LP cells from donor M10 were pooled and counted, therefore no standard deviation is given.
(F) Contraction of individual cells. Confocal microscopy (left): B+ cell derived structures (Donor M8) were treated with TGF-β1 as in (C), and stained with Phalloidin for F-actin (white) and DAPI for cell nuclei (blue). Scale bar: 100 µm. Cell size was determined per condition for 30 cells of 3 different structures using ImageJ area tool.
n.s., not significant; n.a., not applicable.
Data are shown as mean±standard deviation (SD).

Figure 7:
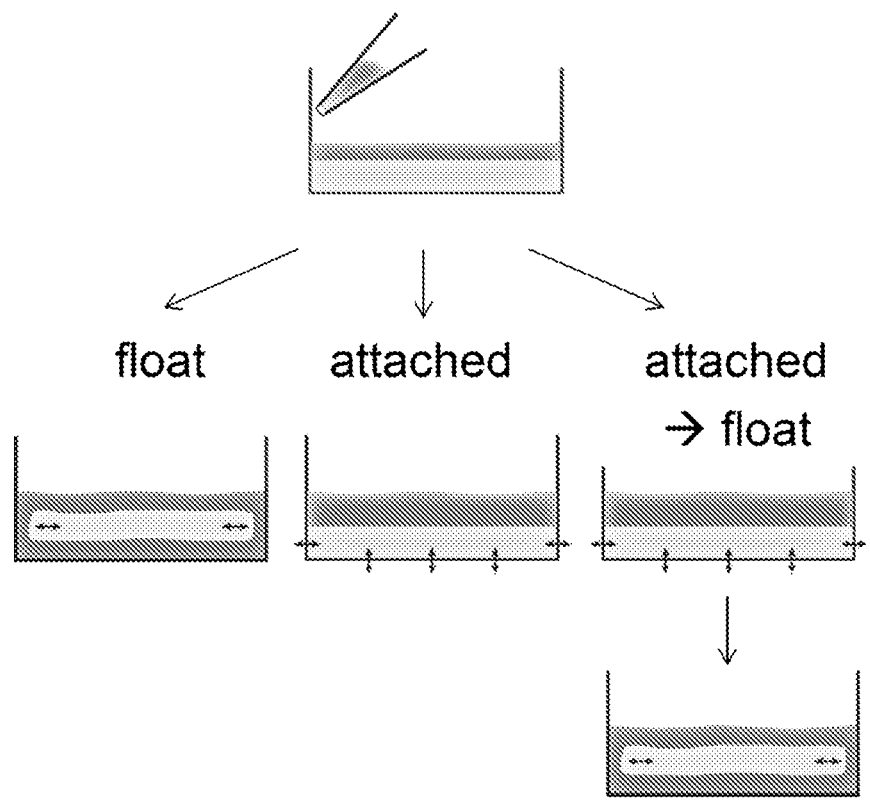
Figure 7:
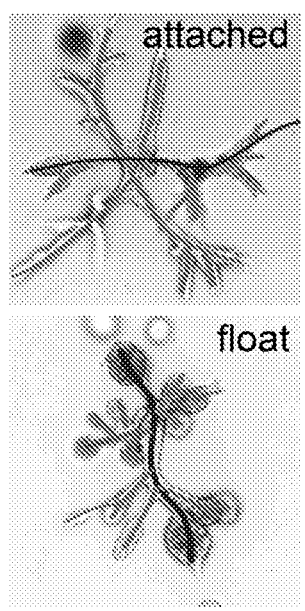
Figure 7:
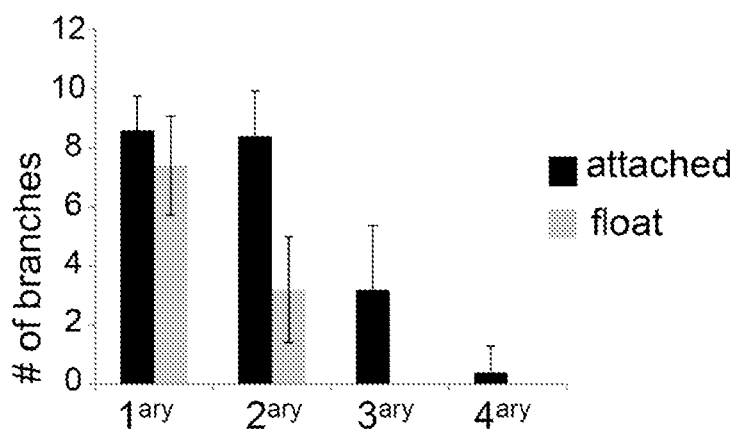
Figure 7:
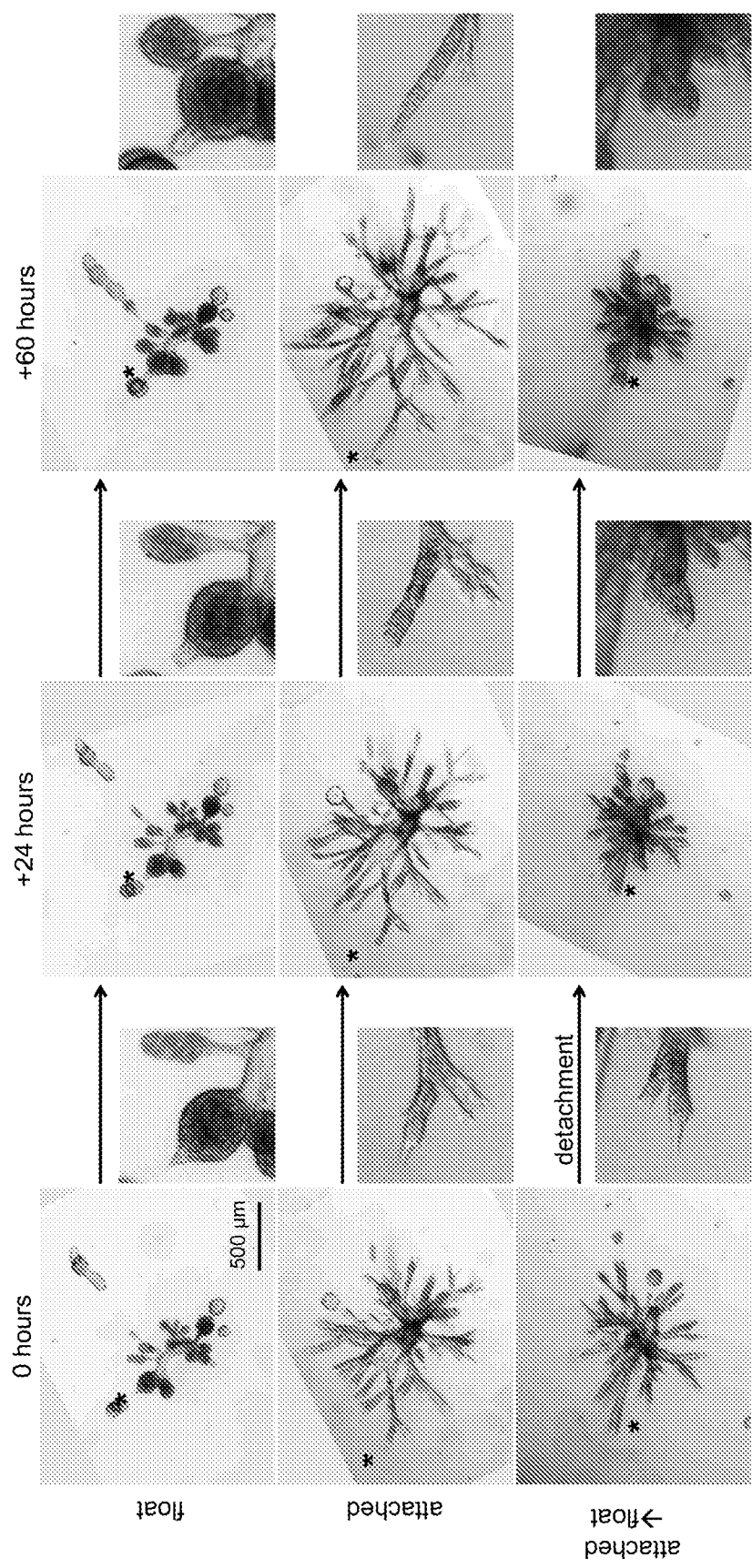
Figure 7:
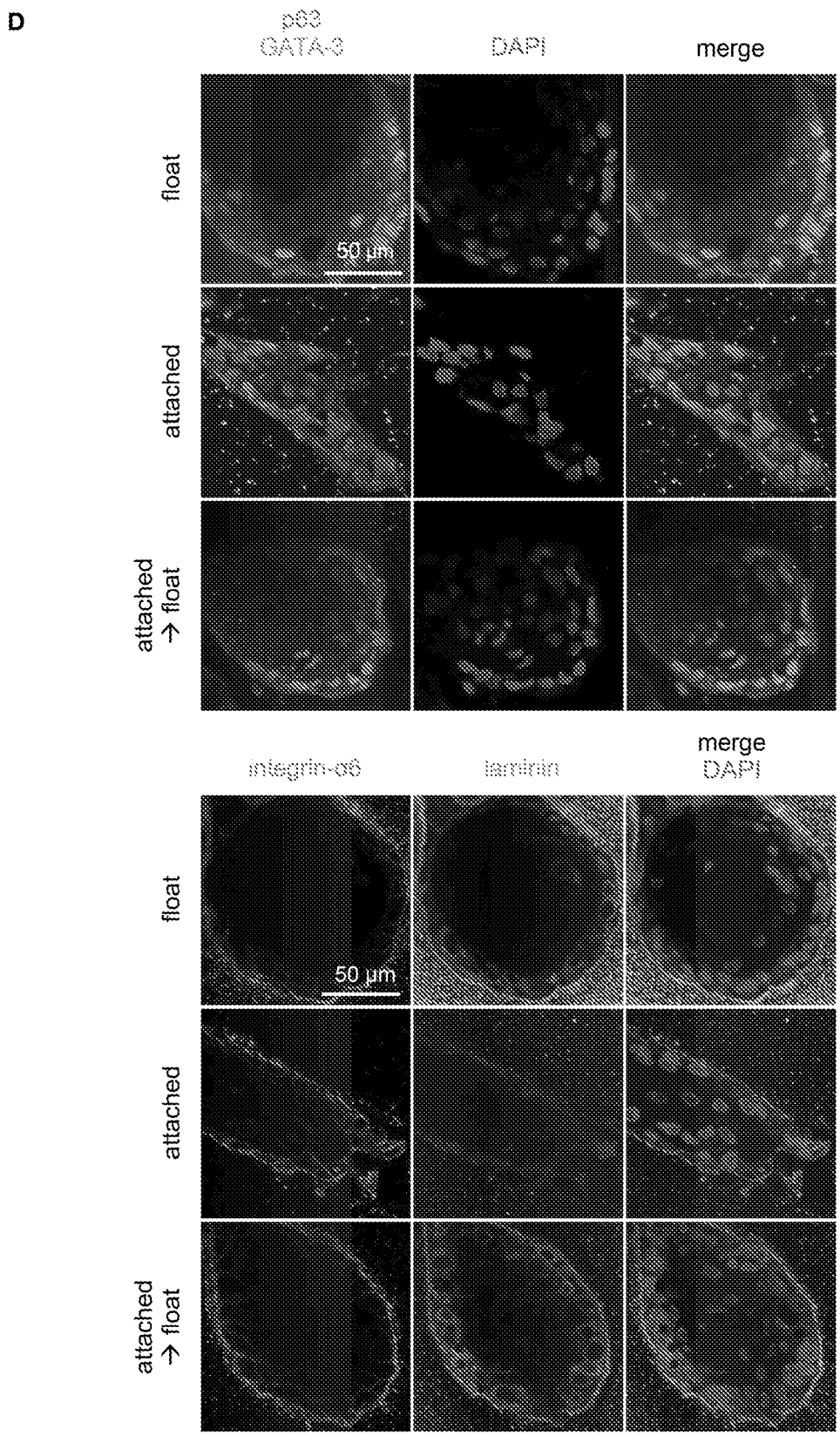

FIG. 7. Matrix compliance in floating collagen gels is necessary for alveologenesis and luminal differentiation of TDLU-like structures.
(A) Experimental layout: Freshly isolated HMEC were seeded into collagen I gels, which were immediately detached to float (left) or left attached to the cell culture dish (middle, right). Once branched structures had formed, half of the attached gels were detached (right).
(B) Bright-field microscopy: representative images of HMEC-derived branched structures (Donor M8), cultured according to (A), and imaged for 60 hours, starting at day 13 of culture. Smaller pictures are details of areas indicated with asterisk. Scale bar: 500 µm.
(C) Quantification of side branches. Left: representative image showing primary, secondary and tertiary side branches indicated by red, blue and yellow lines, respectively. Right: The number of side branches in attached and floating collagen gels at day 13 of culture was quantified for 5 structures per condition (Donor M8).
(D) Confocal microscopy: representative images of HMEC-derived branched structures (Donor M8), cultured according to (A,B): p63 (red), GATA-3 (green), integrin-α6 (red), laminin (green), DAPI for cell nuclei (blue). Scale bar: 50 µm.
Data are shown as mean±standard deviation (SD).

Figure 8:
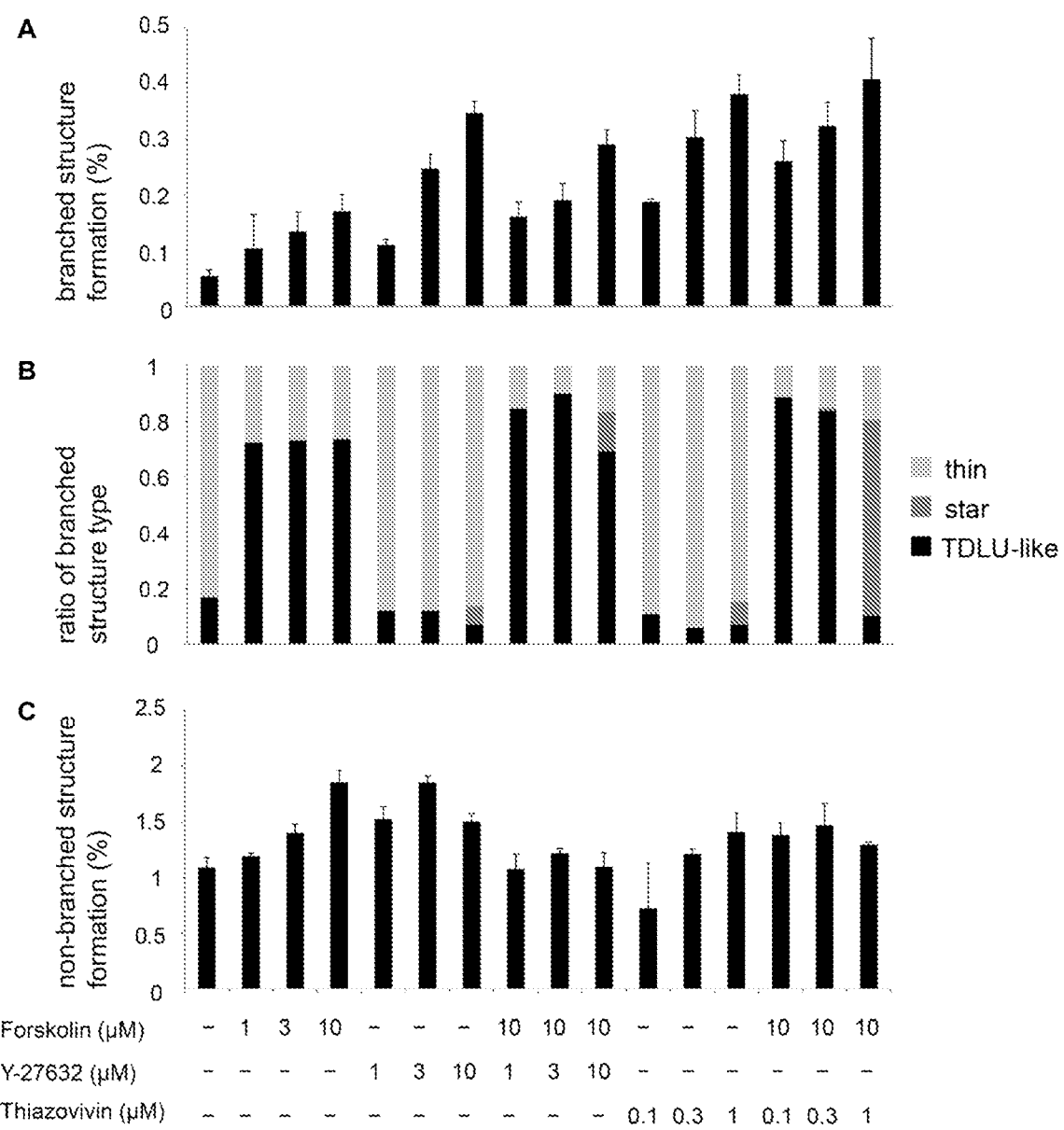

FIG. 8. referring to FIG. 1. Identification of culture conditions that promote generation of TDLU-like structures by freshly dissociated HMEC
(A) Effect of culture conditions on the generation of branched structures: HMEC (Donor M8) were cultured in presence of different concentrations of Forskolin (continuous treatment), Y-27632 and Thiazovivin (both one-time treatment at day 0 of culture) in floating collagen gels for 14 days. n=3 gels/condition. Structure formation is given per 100 seeded cells.
(B) Effect of culture conditions on the ratio of branched structure subtypes, refer to (A). n=3 gels/condition.
(C) Effect of culture conditions on the generation of non-branched structures, refer to (A). n=3 gels/condition. Structure formation is given per 100 seeded cells.

Figure 9A:
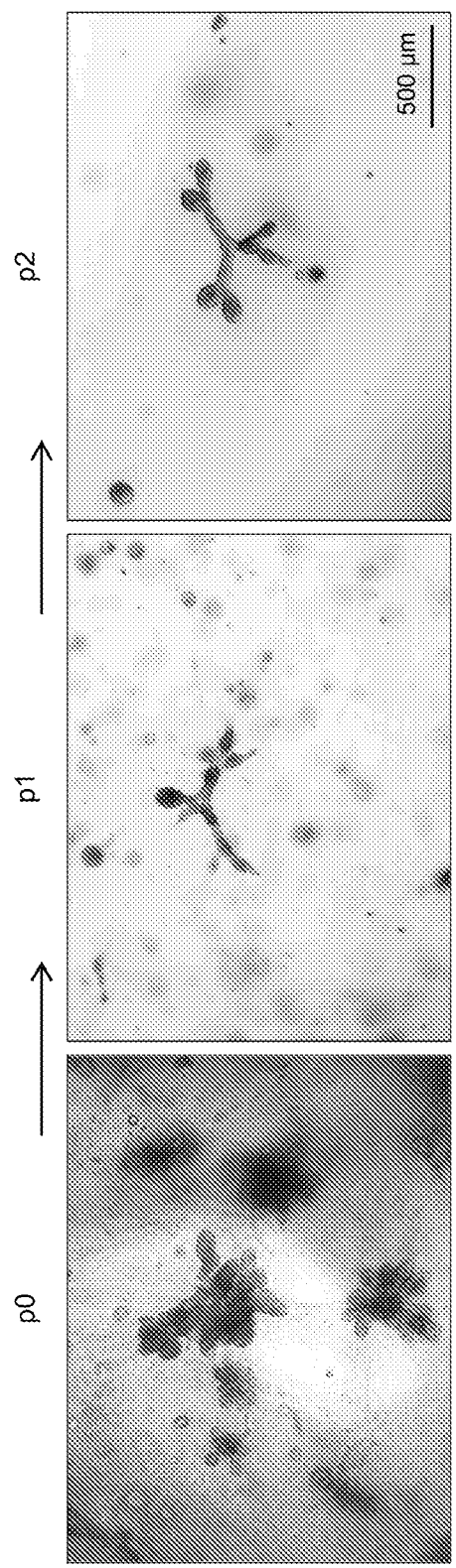
Figure 9:
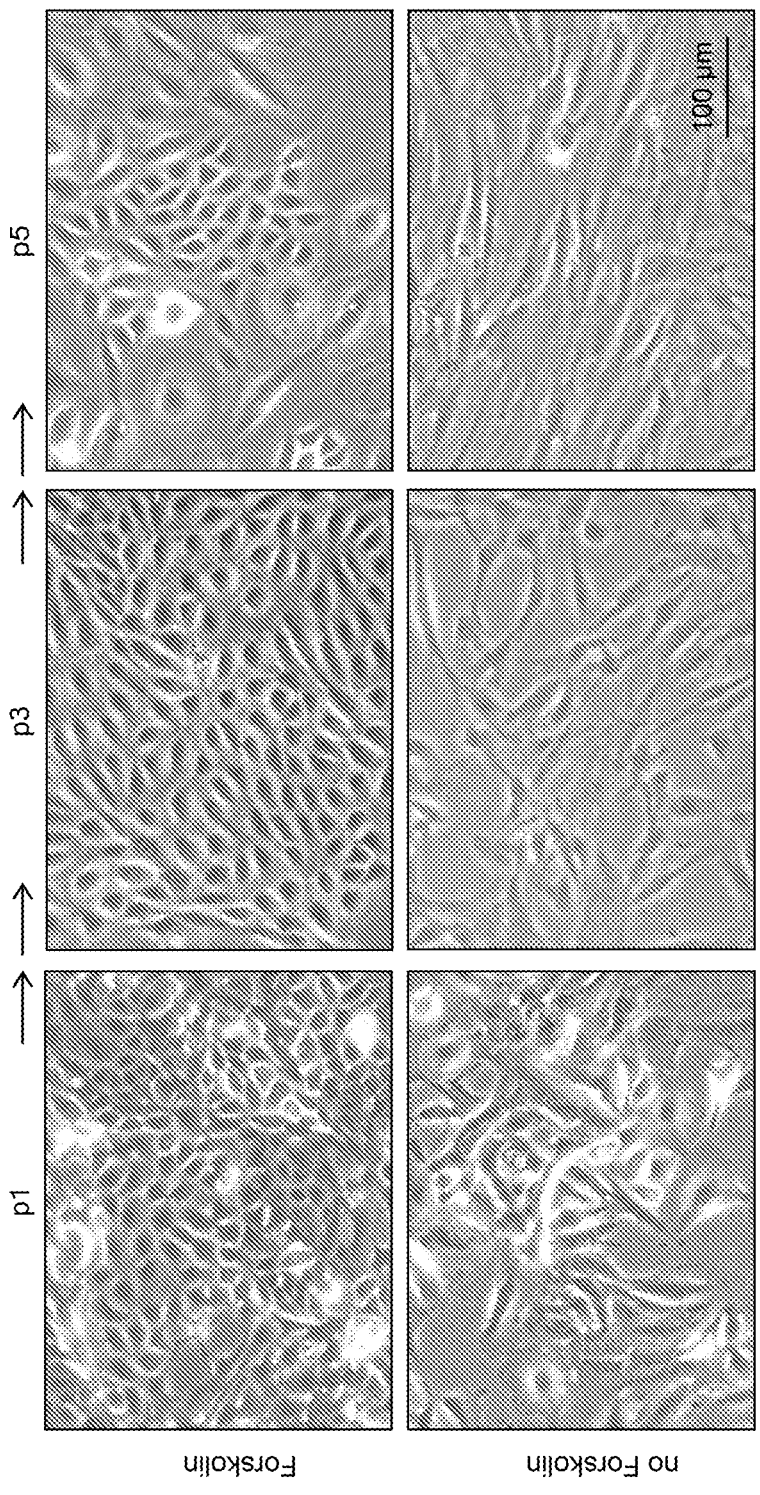
Figure 9:
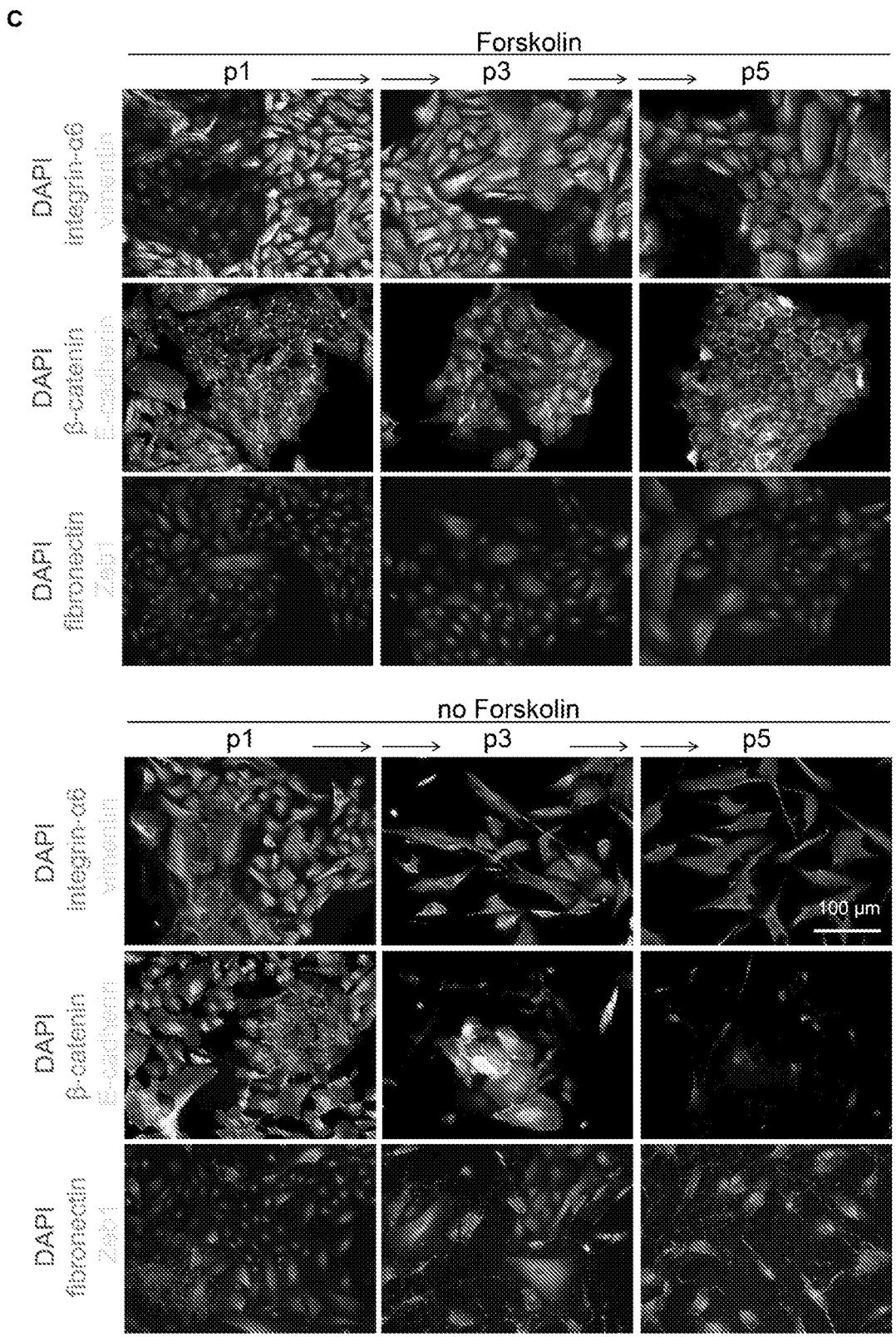
Figure 9:
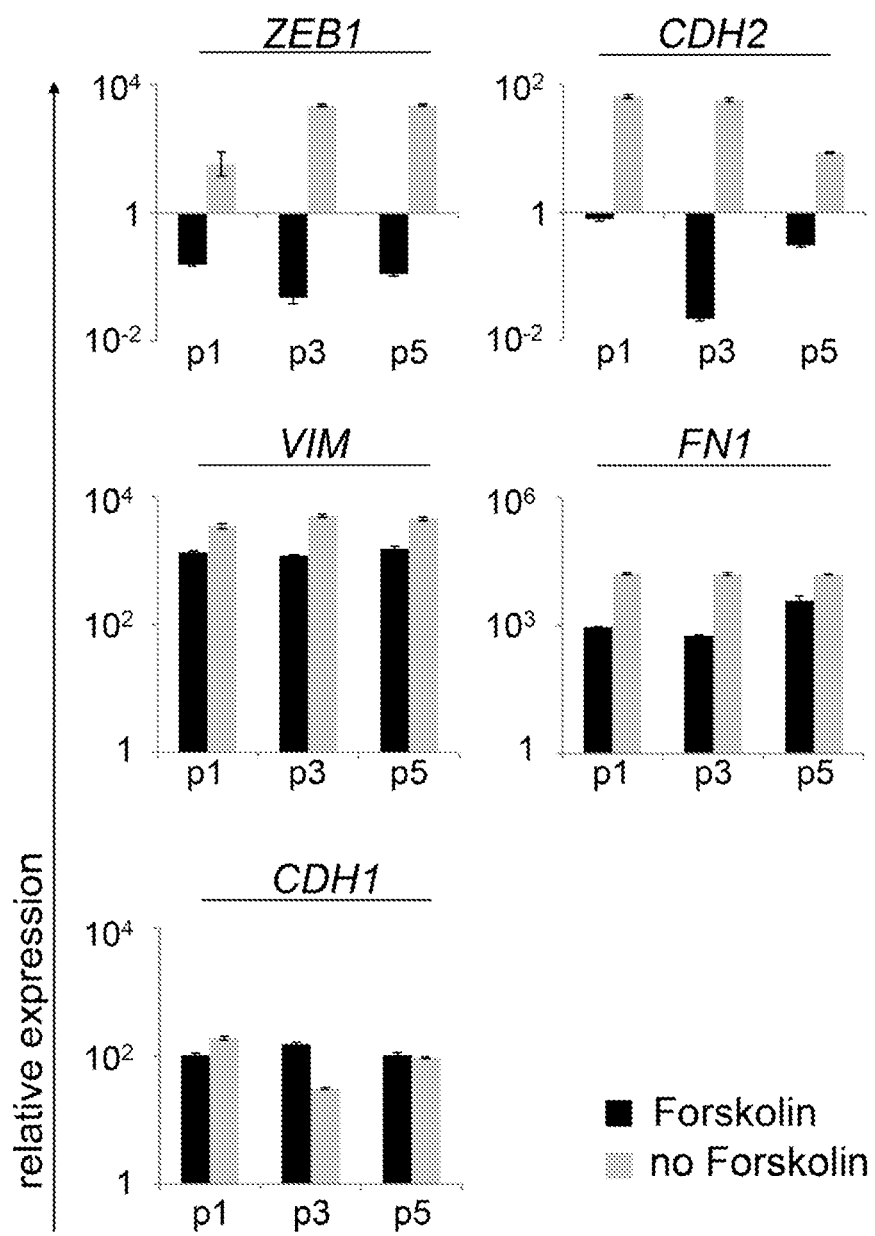
Figure 9:
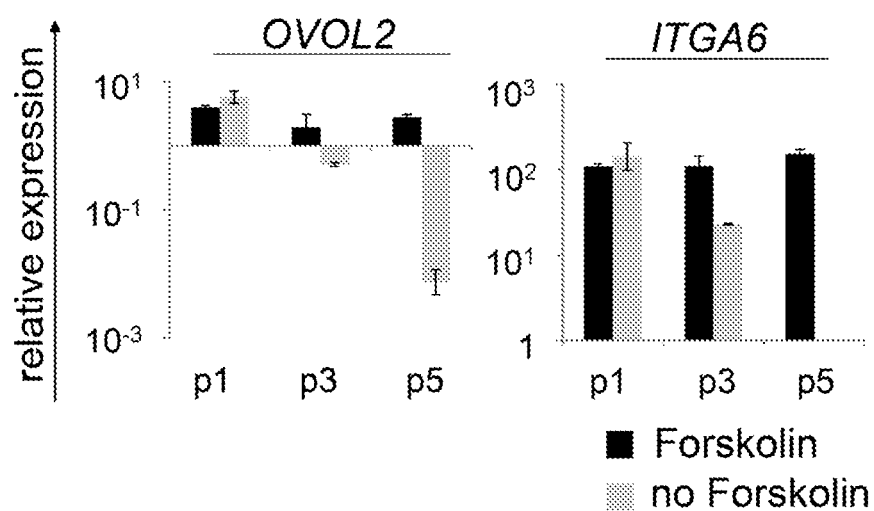
Figure 9:
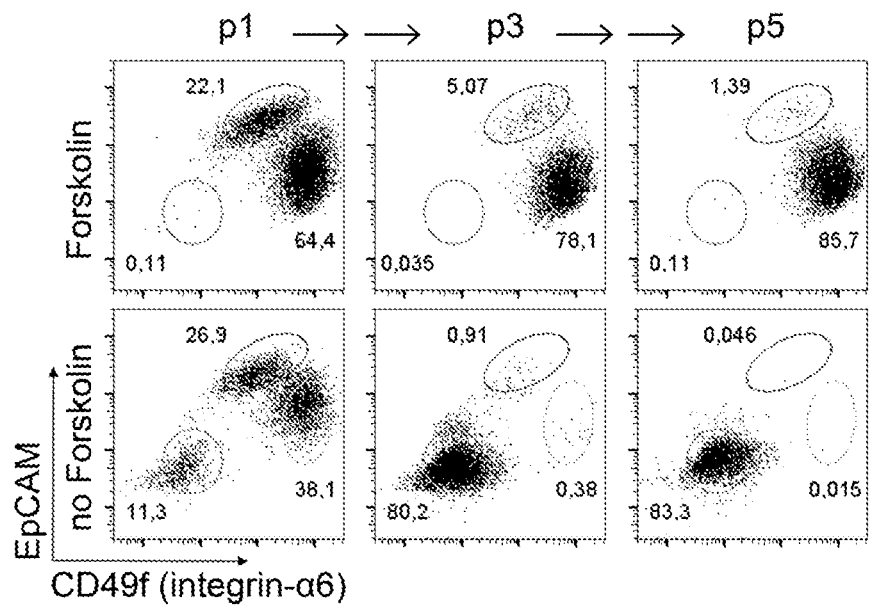

FIG. 9. referring to FIG. 2. Maintenance and expansion of TDLU-like structure formation during passaging and 2D-culture
(A) Bright-field: representative images of HMEC-derived branched structures (donor M8), at subsequent passages in 3D. Scale bar: 500 µm.
(B) Phase contrast microscopy: representative images of HMEC cultured in 2D in the absence or presence of 10 µM Forskolin at passage 1,3 and 5 (donor M4). Scale bar: 100 µm.
(C) 2D-Immunofluorescence: representative images of HMEC cultured in 2D, as described in (B). integrin-α6 (red), vimentin (green), µ-catenin (red), E-cadherin (green), fibronectin (red), Zeb1 (green), DAPI (blue). Scale bar: 100 µm.
(D) RT-PCR: ZEB1, CDH2 (N-cadherin), VIM (vimentin), FN1 (fibronectin) and CDH1 (E-cadherin), mRNA expression of HMEC cultured in 2D, as described in (B). n=3.
(E) RT-PCR: OVOL2 and ITGA6 (integrin-α6) mRNA expression of HMEC cultured, as described in (B). n=3.
(F) Flow cytometry analysis of CD49f and EpCAM expression in Lin⁻ HMEC cultured in 2D, as described in (B).
p, passage.

Figure 10:
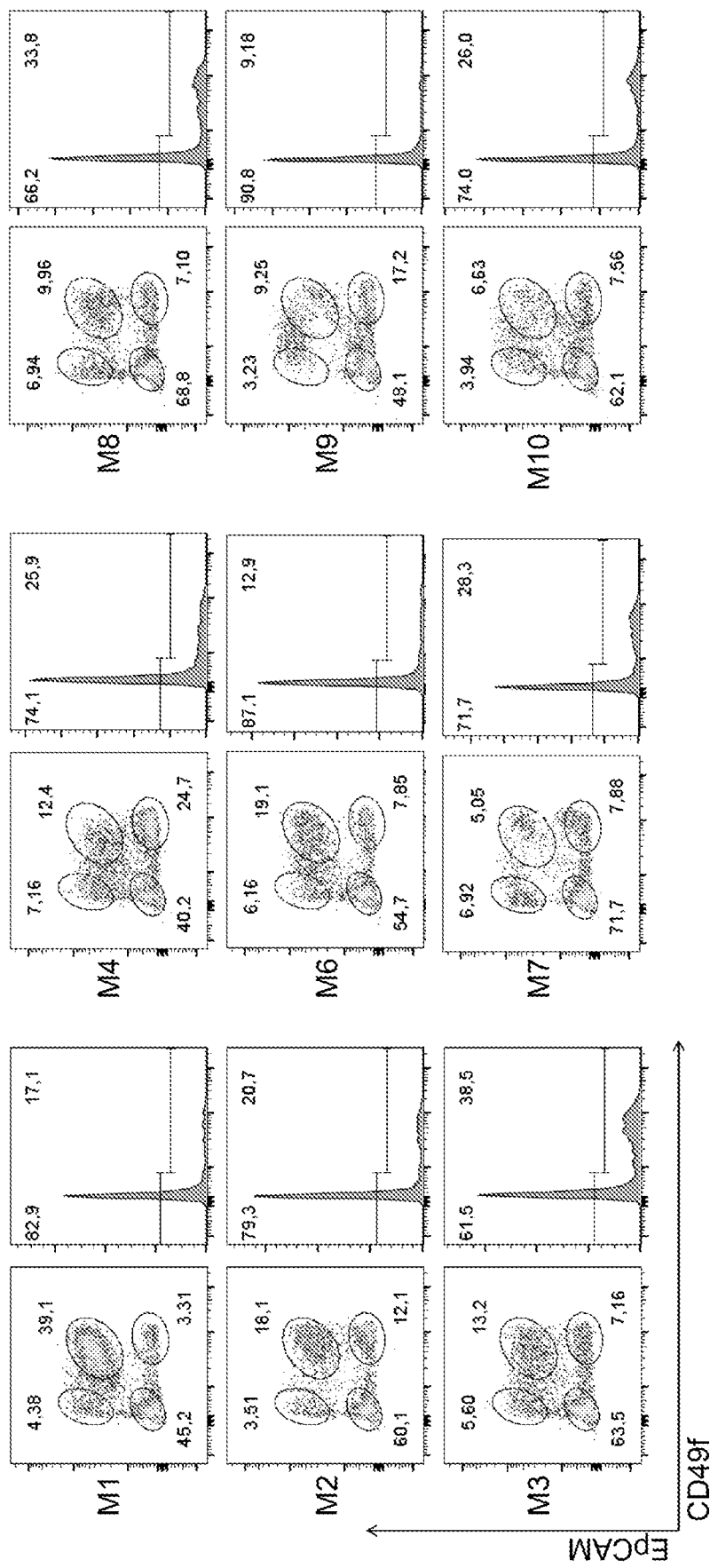
Figure 10:
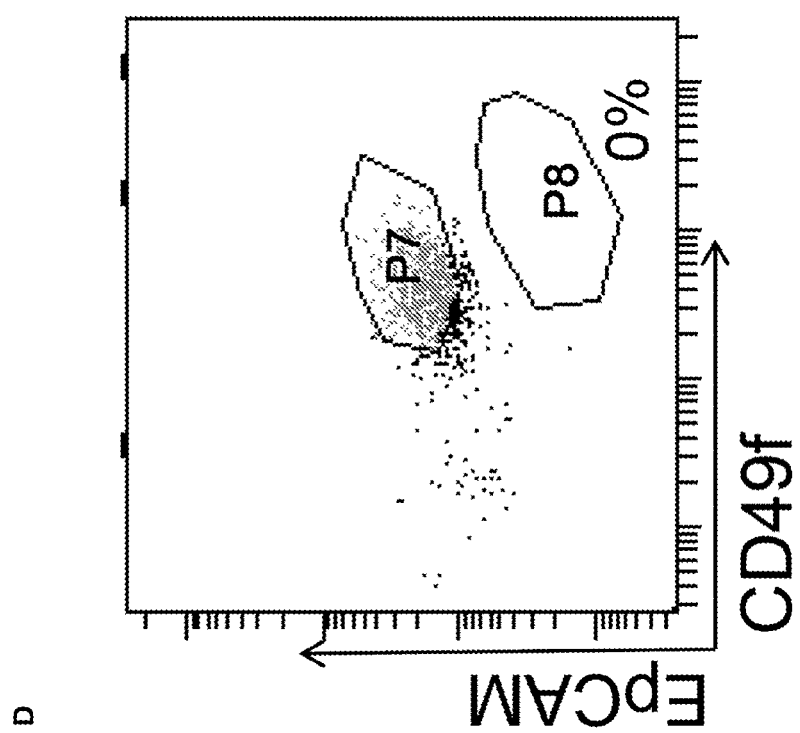
Figure 10:
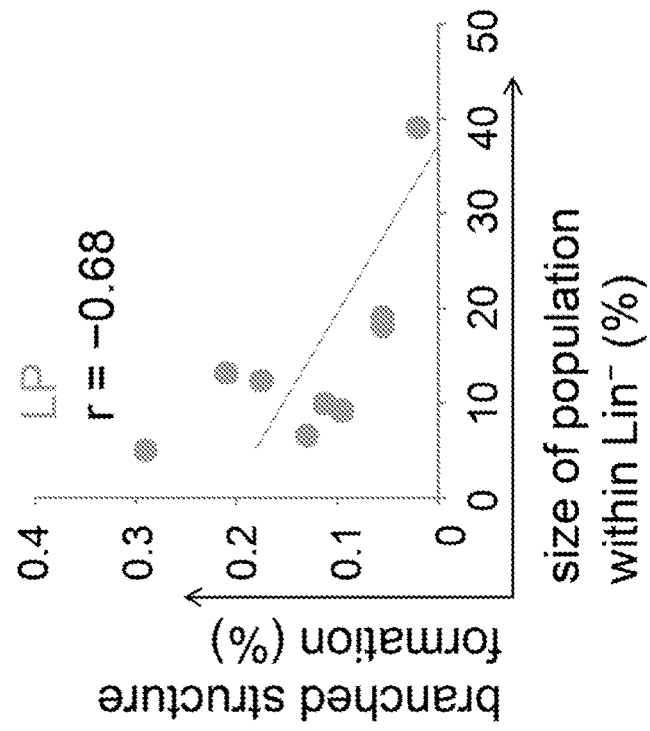
Figure 10:
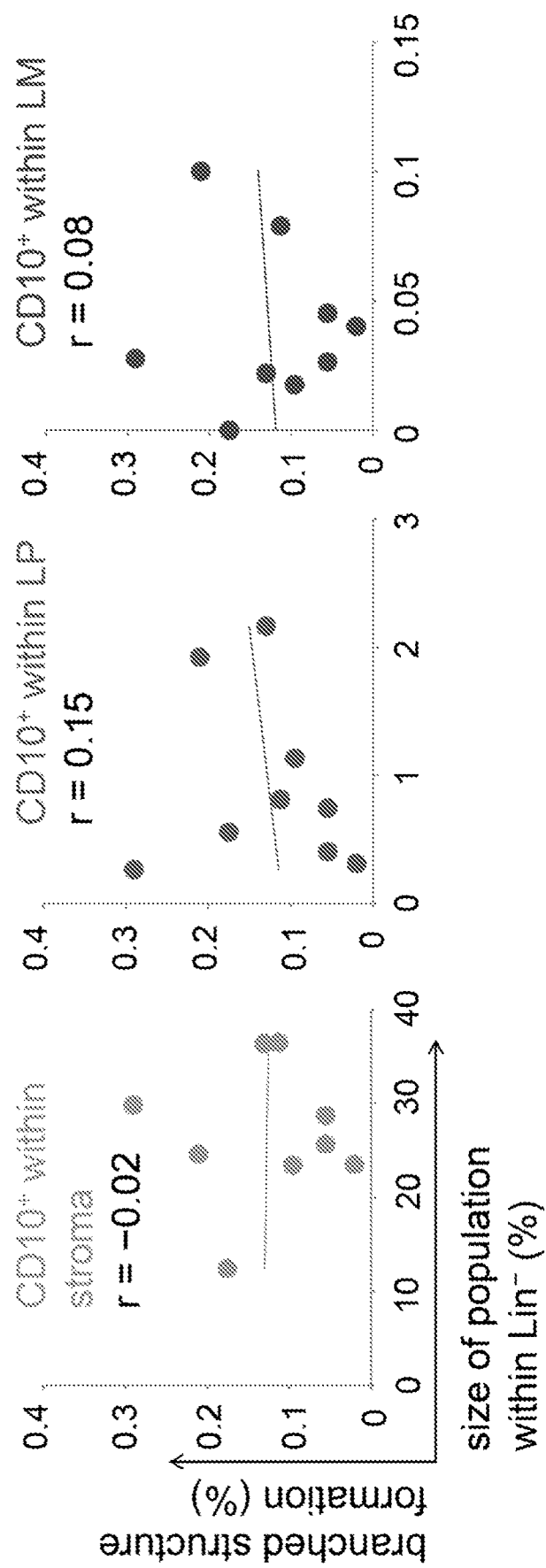

FIG. 10 referring to FIG. 4. TDLU-like structure-forming potential is contained within a $CD10^+/CD49f^{hi}/EpCAM^-$ basal population
(A) Flow cytometry analysis of CD49f, EpCAM and CD10 expression in the 7-AAD⁻, Lin⁻ subset of freshly isolated HMEC from 9 donors (M1-M4, M6-M10) used in FIGS. 3 and 4. Determined population sizes were used for correlation analysis in FIGS. 4B,C and 10B,C.
(B) Correlation between branched structure formation and the size of the LP population. One dot represents one donor.
(C) Correlation between branched structure formation and the size of the CD10+ stromal population ($CD10^+/CD49f^-/EpCAM^-$, green dots), the $CD10^+$ LP population ($CD10^+/CD49f^+/EpCAM^+$, blue dots), and CD10+ LM population ($CD10^+/CD49f^-/EpCAM^+$, dark blue dots). One dot represents one donor.
(D) Reanalysis of the purity of sorted LP cells from donor M8, used for extreme limiting dilution analysis in FIG. 4E.
r, correlation coefficient.

Figure 11:
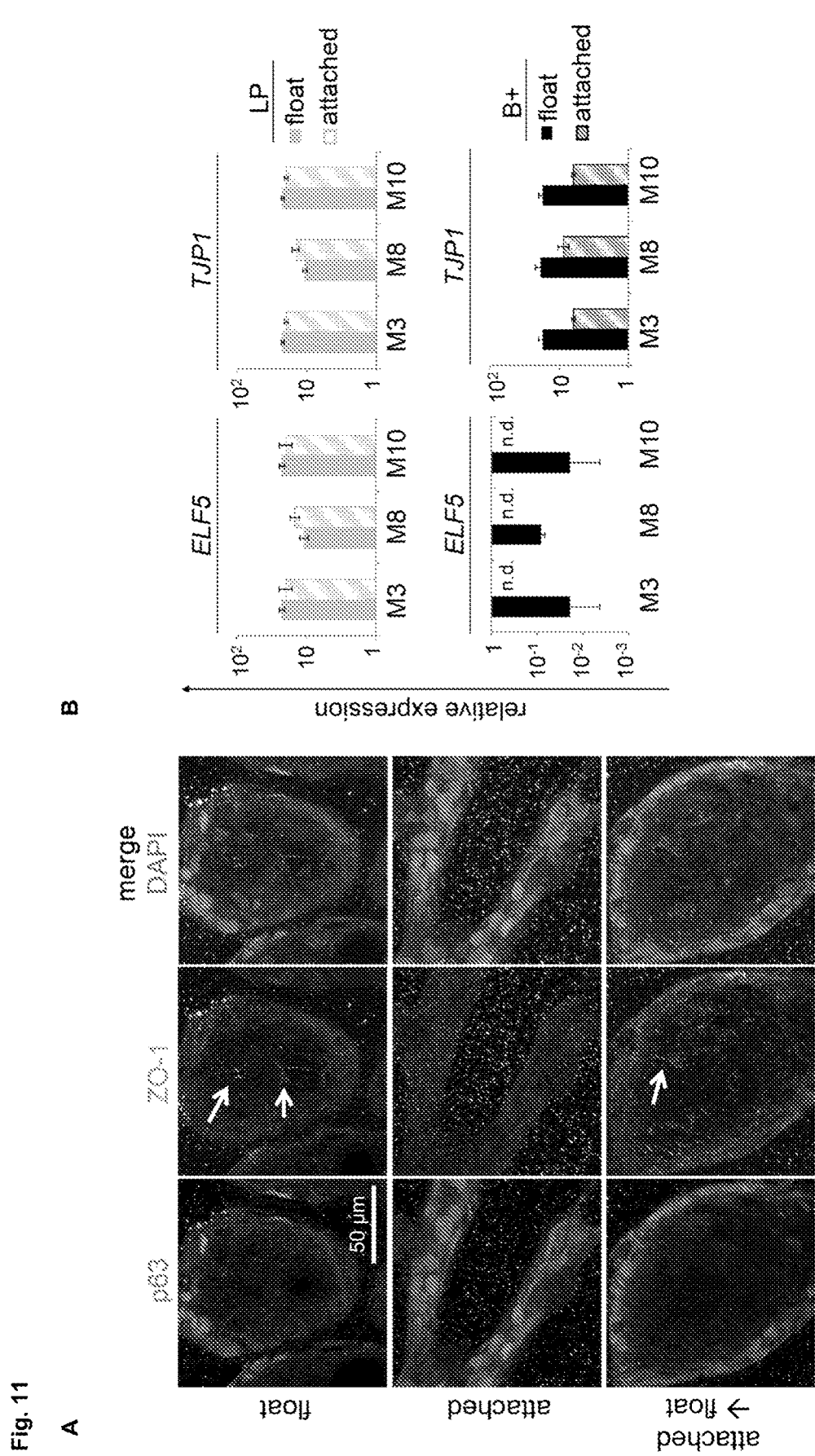
Figure 11:
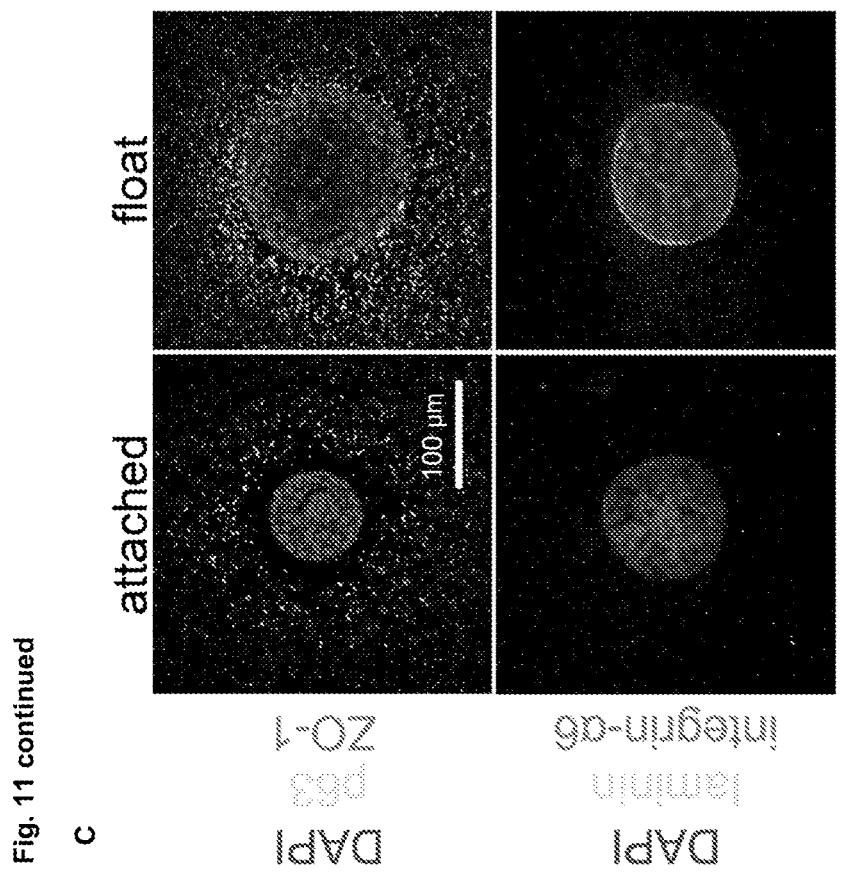
Figure 11:
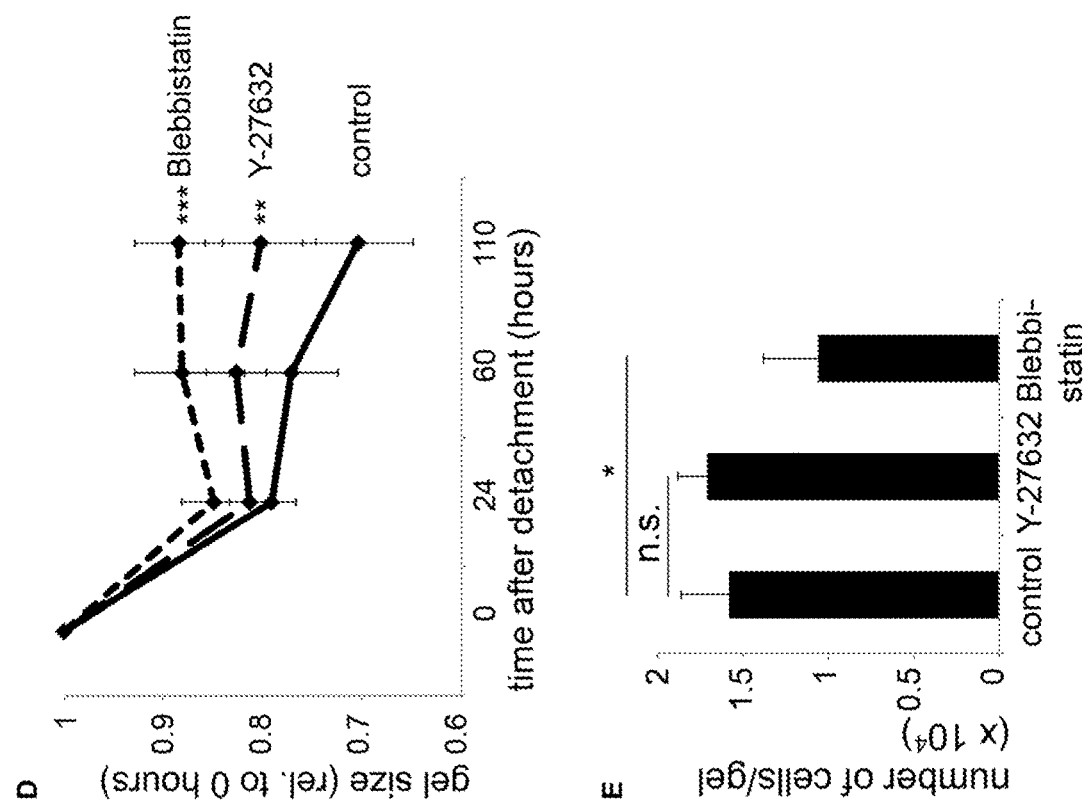

FIG. 11 referring to FIG. 7. Matrix compliance in floating collagen gels is necessary for alveologenesis and luminal differentiation of TDLU-like structures.
(A) Confocal microscopy: representative images of HMEC-derived branched structures (Donor M8), cultured according to FIG. 7A, B. p63 (red), ZO-1 (green), DAPI (blue). Arrows point to ZO-1 expression. Scale bar: 50 µm.
(B) RT-PCR: ELF5 and TJP1 (ZO-1) mRNA expression in B+ and LP cell derived structures from donors M3, M8 and M10, cultured in attached and floating collagen gels. n=3.
(C) Confocal microscopy: representative images of HMEC-derived spheres (Donor M8), cultured in floating and attached collagen gels, at day 14 of culture. p63 (green), ZO-1 (red), integrin-α6 (red), laminin (green), DAPI (blue). Scale bar: 100 µm.
(D) Contraction of collagen gels: HMEC from donor M10 were grown in attached collagen gels. Once branched structures had formed, gels were detached (day 13 of culture) and treated with 10 µM Blebbistatin or 5 µM Y-27632 every 24 hours. The size of the gels was determined directly after detachment (0 hours), and after 24, 60 and 110 hours. Gel size is plotted relative to the timepoint of detachment (0 hours). n=16 gels/condition. (E) Quantification of the average number of cells per gel at the end of analysis shown in (D), n=4.
(F) Bright-field microscopy: representative images of HMEC-derived branched structures (Donor M10) cultured in attached collagen gels for 12 days, detached on day 13 of culture, and treated with 10 µM Blebbistatin or 5 µM Y-27632 every 24 hours. Structures were imaged for 60 hours. Smaller pictures are details of areas indicated with asterisk. Scale bar: 500 µm.
n.d., not detectable
n.s., not significant

DETAILED DESCRIPTION

The present inventors pioneered in providing an organoid assay that enables single cells from mammary epithelial tissue to recapitulate mammary gland development, homeostasis and disease-development. In particular, the present inventors have developed means and methods, i.a. culturing conditions, that allow cells freshly isolated from primary mammary epithelial tissue to form structures that resemble the terminal ductal-lobular unit (TDLU), the functional unit of the breast.

The means and methods provided herein enables detection, isolation and manipulation of breast-stem cell-containing cell populations, in particular such isolated from primary tissue, and studying of key aspects of tissue architecture and function. It also allows for quantification of regenerative potential on a single-cell level. The assay is highly quantitative and scalable, and provides a highly sensitive and specific, thus reproducible functional readout that is suitable for high-throughput screening.

Accordingly, the present invention provides a method of generating cells capable of differentiating to a multicellular organoid unit that morphologically and/or functionally resembles the terminal ductal-lobular unit, comprising
(i) culturing dissociated cells from mammary epithelial tissue in a collagen gel for at least 7 days, said culture medium comprising a compound which elevates cAMP levels;
(ii) determining whether a multicellular organoid unit is formed in step (i); and
(iii) obtaining a single cell from said multicellular organoid unit of (ii).

(i) Cells and Cultivation

In step (i) of the above-described method of the invention, dissociated cells from mammary epithelial tissue are cultured. It is in general conceivable to use cells obtained from any of a wide variety of sources, e.g. the cells may be primary cells, cells of a cell line, untransformed cells, transformed cells, genetically modified cells, or non-genetically modified cells. Induced pluripotent stem cells are also envisaged. In general, any type of cell that can be obtained from mammary epithelial tissue can be used in the methods of the invention. The use of primary cells (i.e., directly derived from mammary epithelial tissue) can be particularly advantageous when it is desired to most accurately reflect cell behaviour in vivo. Primary cells dissociated from mammary epithelial tissue include, for example, mammary epithelial cells (MEC), including e.g. myoepithelial and luminal mammary epithelial cells, myoepithelial and luminal mammary progenitor cells, and adult mammary stem cells (MaSC).

In particular, the term "cells dissociated from mammary epithelial tissue" includes any type of stem cells obtainable from mammary epithelial tissue using means and methods known in the art. In general, "stem cells" are undifferentiated cells that have the ability to go through numerous cycles of cell division while maintaining the undifferentiated state (self-renewal) and can differentiate into specialized cell types (potency).The term in particular also includes "breast stem cells" as defined elsewhere herein.

It is further also conceivable to use cells dissociated from other tissues, e.g. epithelial tissues of the pancreas, lung, or kidney. Particularly envisaged in this regard are cells, in particular stem cells, having the ability of forming a multicellular organoid unit comprising ductal structures and/or multiple branch-points and/or alveoli and/or may also be capable of contracting a collagen gel, preferably a free-floating collagen-I gel. Said cells can be primary cells, cells of a cell line, untransformed cells, transformed cells, genetically modified cells, non-genetically modified cells, or induced pluripotent stem cells.

For example, primary human mammary epithelial cells (HMEC) can be derived from fresh breast reduction tissue (reduction mammoplasty) by mechanical and/or enzymatic dissociation and, if desired, can be further purified by methods such as fluorescence activated cell sorting (FACS). Human and murine breast cancer-derived established cell lines, such as MCF7, MDA-MB-231 and 4T1 cells can also be used. One of skill in the art would be aware of other cell lines (e.g., derived from other cancer types) that may be used in embodiments of the invention. The term "dissociated" means that individual cells have been released from a cell compound, cell agglomeration or tissue.

It is envisaged that "dissociated cells" are derived from healthy or diseased mammary epithelial tissue. "Diseased tissue" in particular refers to tissue comprising cells with germline or somatic mutations, e.g. in proto-oncogenes. The term includes tissue comprising cancerous and/or pre-cancerous cells and/or tissue derived from a patient diagnosed with breast cancer. "Healthy tissue", on the other hand, refers to tissue from healthy donors that preferably does not comprise germline or somatic mutations, cancerous and/or pre-cancerous cells.

In order to obtain dissociated cells, mammary epithelial tissue can be dissociated mechanically and/or enzymatically. Means and methods for mechanical and enzymatical tissue dissociation are well-known in the art. E.g., the tissue can be minced using scalpels or other suitable tools. Other means of mechanical tissue dissociation are also conceivable, e.g. sonication or others. Further, tissue dissociating agents may be used, typically including tissue degrading enzymes such as collagenase, trypsin, neutral protease or dispase, and other proteolytic enzymes. However, the tissue dissociating agents are not necessarily limited to enzymes. Other examples of tissue dissociating agents are chelating agents. The length of time required for treatment will vary depending on the sonication frequency, type of the agent, the concentration of agent, and the temperature at which treatment is conducted. Treatment is allowed to proceed until a sufficient amount of tissue has dissociated without causing undue damage to released cells or cellular aggregates. Dissociation advantageously also comprises obtaining a single-cell suspension of the dissociated cells as described in the appended examples.

Next, dissociated cells are plated in collagen gels. The collagen gel may be composed of one collagen type or a mixture of collagen types. A collagen type is, for example, type I, II, III, IV of V, with the type I being preferred. The collagen concentration may be in the range of about 0.5 to 2 mg/ml, preferably of about 0.8 to 1.8 mg/ml and even more preferred of about 1.0 to 1.5 mg/ml. The term comprises attached and free-floating collagen gels.

The term "attached gel" as used herein, refers to a rigid collagen gel that sticks to the surface of the cell culture dish. This is in contrast to a "floating gel" that has been mechanically detached from the cell culture dish after polymerization of the gel and is thereby able to float in the cell culture medium. A floating gel is therefore more compliant than an attached gel and can e.g. contract or expand.

E.g., the gel can be a collagen-I gel that is attached or free-floating in growth medium.

The growth medium is advantageously supplemented with a compound which elevates cAMP levels. Optionally, the growth medium may be supplemented with a ROCK inhibitor.

A "compound which elevates cAMP levels" can in general be any compound that is capable of increasing levels of cyclic adenosine monophosphate (cAMP). The capability of compounds to do so can be assessed e.g. by commercially available test kits such as the Promega cAMP-Glo™ Assay which is based on the principle that cyclic AMP (cAMP) stimulates protein kinase A (PKA) holoenzyme activity, decreasing available ATP and leading to decreased light production in a coupled luciferase reaction. Without wishing to be bound by theory, addition of a compound which elevates cAMP levels is thought to promote formation of TDLU-like branched structures and/or alveologenesis. The compound can for example be an activator of adenylylcyclase, or the compound can be cAMP, or a cAMP mimetic (i.e. having cAMP functionality). The term "activator of adenylylcyclase" comprises compounds that elevate cAMP levels by directly activating adenylylcyclase (e.g. by binding to adenylylcyclase). Said compounds are designated "adenylylcyclase agonists" herein. The term "activator of adenylylcyclase" also comprises compounds that elevate cAMP levels by indirectly activating adenylylcyclase, e.g. by activating stimulators of adenylylcyclase (such as activating G-protein coupled receptor subunits) or by inactivating inhibitors of adenylylcyclase (such as inhibitory G-protein coupled receptor subunits). Exemplary compounds include choleratoxin and pertussistoxin. However, particularly envisaged compounds for elevating cAMP levels are adenylylcyclase agonists, such as Forskolin.

The present inventors also discovered that addition of a ROCK inhibitor can increase formation of TDLU-like branched structures. Thus a ROCK inhibitor can be added to improve cell culture conditions. However, supplementing a ROCK inhibitor for more than about 5 days may result in dissociation of cell-cell adhesion, thereby perturbing morphogenesis. Hence, it is envisaged that the ROCK inhibitor may be removed after about 5 days from the culture medium. Changes in cell-cell adhesion and morphology can be monitored macro- and microscopically, in order to determine the need and time point of removing the ROCK inhibitor.

A "ROCK inhibitor" as used herein is compound that acts as an inhibitor of Rho-associated protein kinase, i.e. reduces or even abolishes ROCK functionality. The capability of a compound to act as a ROCK inhibitor can be assessed by various means, e.g. by determining its ability to compete with ATP for binding to ROCK and/or by assessing its effects on cell morphology, G1-S Transition and cytokinesis as described in Ishizaki T Mol Pharmacol. 2000 May; 57(5):976-83. The inhibitor may be either unspecific or specific for either of the ROCK isoforms ROCK1 and/or ROCK2. ROCK inhibitors known in the art have been reviewed in Liao et al. J Cardiovasc Pharmacol. 2007 July; 50(1): 17-24 and include Fasudil, Y-27632, Thiazovivin, Y39983, Wf-536, SLx-2119, Azabenzimidazole-aminofurazans, DE-104, Olefins, Isoquinolines, Indazoles, pyridinealkene derivatives, H-1152P, ROKα inhibitor, XD-4000, 4-(1-aminoalkyl)-N-(4-pyridyl)cyclohexane-carboxamides, HMN-1152, Rhostatin, BA-210, BA-207, BA-215, BA-285, BA-1037, Ki-23095, VAS-012, with Y-27632 or Thiazovivin being particularly envisaged for use in the method of the invention.

The present inventors have observed that culture medium comprising Y-27632 or Thiazovivin as a ROCK inhibitor and an adenylylcyclase agonist such as Forskolin as a compound which elevates cAMP levels is one particularly useful culture medium for use in the methods of the present invention. E.g., the culture medium may comprise Y-27632 in a concentration of about 1-5 µM, about 2-4 µM or about 3 µM, and Forskolin in a concentration of about 5-15 µM, about 6-14 µM, about 7-13 µM, about 8-12 µM, about 9-11 µM or about 10 µM. It is however to be noted that the ROCK inhibitor may be removed after a while from the culture medium as described herein.

(ii) Multicellular Organoid Unit

Next, it is determined whether a multicellular organoid unit has been formed in step (i).

A "multicellular organoid unit" is a multicellular structure that is formed by a single cell. It is in particular envisaged that the single cell is a stem cell, preferably a breast stem cell as described herein. The multicellular organoid unit morphologically and/or functionally resembles the terminal ductal-lobular unit (TDLU) and is therefore also termed "TDLU-like (branched) structure" herein. The term "terminal ductal-lobular unit" or "TDLU" as used herein is a structure of the breast. Each breast lobe is drained by a collecting duct terminating in the nipple. The collecting duct has several branches, which end in a terminal ductal-lobular unit (TDLU), the basic functional and histopathological unit of the breast. The TDLU is composed of a small segment of terminal duct and a cluster of ductules, which are the effective secretory units. The functional structures are surrounded by specialized connective tissue. A normal terminal ductal lobular unit ranges from 1-4 mm. The TDLU is composed of the extralobular terminal duct, intralobular terminal duct, lobule (functional unit of the breast)

However, though a multicellular organoid unit is ideally morphologically and/or functionally identical to a TDLU, it cannot be excluded that there may be differences. These differences are reflected in the term "organoid" meaning it is an organ structure (i.e. an entire organ or functional part thereof) that is formed and grown ex vivo which ideally morphologically and/or functionally resembles an organ structure. The same is true for the term "resemble". It means that a multicellular organoid unit is/behaves like an organ structure and thus morphologically and/or functionally behaves like a (natural) organ structure. However, in contrast to a (natural or in vivo) organ, an organoid structure is formed and grown ex vivo. An example for a difference between a TDLU and a multicellular organoid unit is lactation. While a TDLU being part of the (natural) breast is able to secrete milk, a multicellular organoid unit is, to the best of the knowledge of the present inventors, not able to do so. However, nonetheless, a multicellular organoid unit shares identity with the natural TDLU as regards morphology in that it comprises ductal structures, multiple branchpoints and advantageously alveoli. From a functional perspective, a multicellular organoid unit is, like a natural TDLU, capable of contraction. Contraction may be tested as described herein.

A multicellular organoid unit is in particular considered to morphologically and/or functionally resemble the TDLU when it comprises ductal structures and/or multiple branchpoints. It may also comprise alveoli at the tip of the ducts. Presence of the aforementioned features in a multicellular organoid unit can be easily assessed by the skilled person using visual examination, e.g. bright-field microscopy as described in the appended examples.

It is further envisaged that the multicellular organoid unit is responsive to hormones and/or growth factors. Hormones include steroid hormones: estrogen, progesterone and androgens, pituitary hormones: prolactin, human growth hormone, other peptide hormones: gluco- and mineralcorticoids, insulin. Growth factors and morphogenes include the following families: EGF (Epidermal Growth Factors), IGF (Insulin-like growth Factors), FGF (Fibroblast Growth Factors), Wnt (Wingless), TGF-beta (Transforming Growth Factor beta), Notch, shh (sonic hedgehog). Included are endogenous and recombinant factors, precursors and derivatives, as well as endogenous, recombinant and synthetic agonists and antagonists. Responsiveness to hormones and growth factors renders the multicellular unit of the present invention a suitable substrate to test compounds for their ability to elicit a physiologically response.

(iii) Single Cell

In step (iii) of the method of the invention, a single cell is obtained from the multicellular organoid unit formed in step (ii) of the method.

It is envisioned that said cell is a single breast stem cell. Over the course of at least 10 days single breast stem cells will generate complex gland structures, i.e. a multicellular organoid unit that morphologically and/or functionally resembles the terminal ductal-lobular unit. It can be determined whether said multicellular organoid unit comprises ductal structures and/or multiple branch-points and/or alveoli as described herein. Also or alternatively, it can be determined whether said multicellular organoid unit is capable of contracting a floating collagen gel, preferably a free-floating collagen-I gel. Such contraction may then be indicative of alveologenesis of said multicellular organoid unit.

The term "breast stem cell" as used herein thus refers to a cell capable of forming a multicellular organoid unit comprising ductal structures and/or multiple branch-points and/or alveoli and/or may also be capable of contracting a collagen gel, preferably a free-floating collagen-I gel, such a cell is a breast stem cell. In particular, the breast stem cell is envisioned to be $CD31^-$, $CD45^-$, $EpCAM^-$, $CD49f^+$ and $CD10^+$.

Such a breast stem cell can be obtained as a single cell by means and methods known in the art from said multicellular organoid unit. Indeed, the present inventors demonstrated that such a breast stem cell obtained from a multicellular organoid unit of the present invention will again, when plated in a collagen gel, form another multicellular organoid unit. This is the proof for such a cell to be a breast stem cell.

(iv) Gel Contraction

The inventors have further observed that multicellular organoid structures were able to contract floating gels, presumably reflecting the contraction of the TDLU ducts during lactation. The method of the invention may further comprise a step of determining whether the obtained multicellular organoid unit is capable of contracting a floating collagen gel. Without wishing to be bound by theory, the present inventors observed that alveoli preferably developed when cells were cultivated in compliant, floating collagen gels, and that alveologenesis further was dependent on and/or triggered by contraction of the collagen gel. Thus, contraction of a floating gel by a multicellular organoid unit is envisaged to be indicative of alveologenesis.

Contraction of the collagen gel may be quantified by measurement of the gel size at various times with a ruler or with image analysis software, such as NIH Image or Image Pro-Plus (MediaCybernetics) and can be correlated to breast stem cell content.

As set out herein, the present inventors have discovered that alveologenesis may be triggered by contraction of the collagen gel. Consequently, the present invention also provides a method for influencing the behaviour, i.e. triggering cell differentiation and hence alveologenesis, by providing the mechanic stimulus via detachment of an attached collagen gel. It is therefore possible to synchronize alveologenesis in a multitude of multicellular organoids.

(v) Enrichment

As set out elsewhere herein, the present inventors identified a combination of surface markers that can be used to enrich cells, in particular breast stem cells, from a population of mammary epithelial cells. Without wishing to be bound by theory, the present inventors noted that the cell surface marker combination of $CD31^-$, $CD45^-$, $EpCAM^-$, $CD49f^+$ and $CD10^+$ correlated to multicellular organoid unit formation capacity. It is speculated that the aforementioned combination of surface markers is specific for breast stem cells of the basal mammary epithelial cell population. Accordingly, the method may further comprise a step of enriching a population of cells by sorting the cells for the cell surface marker combination $CD31^-$, $CD45^-$, $EpCAM^-$, $CD49f^+$ and $CD10^+$ prior to culturing said cells in a collagen gel.

Enrichment of cells with the desired surface markers can be accomplished using methods known in the art, e.g. by fluorescence-activated cell sorting (FACS) as described in the appended examples.

This step can advantageously be used to enrich cells capable of differentiating to a multicellular organoid unit that morphologically and/or functionally resembles the terminal ductal-lobular unit, but is not a mandatory prerequisite to obtain a single breast stem cell from said multicellular organoid unit, since such a breast stem cell can readily be obtained as described above, i.e., without prior enrichment, but merely on the basis that, when plated in a collagen gel, preferably a collagen-I gel, it is capable of differentiating to a multicellular organoid unit that morphologically and/or functionally resembles the terminal ductal-lobular unit as described herein.

(vi) Pre-Cultivation

The method of the invention may further comprise a step of culturing the dissociated cells in 2D-culture (or other methods) prior to transferring them to collagen gels. This step is also referred to as "pre-cultivation" herein.

Without wishing to be bound by theory, it is thought that 2D-pre-cultivation may increase the ability of primary mammary epithelial cells to form multicellular organoid units. Pre-cultivation, in particular 2D pre-cultivation, further allows genetic manipulation of the cells prior to cultivation in the collagen gel. Pre-cultivation can be accomplished using standard protocols known in the art, depending on the type of cell, length of cultivation, desired cell morphology and density and other parameters. An exemplary protocol for pre-cultivation of human primary epithelial cells can be found in the appended examples.

Breast Stem Cell

Furthermore, the present invention relates to a breast stem cell obtainable by the methods of the invention, in particular using a collagen-I gel for cultivation. Said breast stem cell is envisaged to be capable of differentiating in a collagen gel to a multicellular organoid unit that morphologically and/or functionally resembles the terminal ductal-lobular unit, wherein said multicellular organoid unit comprises ductal structures and multiple branch-points and/or is capable of contracting a floating collagen gel. In particular, the breast stem cell may be $CD31^-$, $CD45^-$, $EpCAM^-$, $CD49f^+$ and $CD10^+$.

It is further envisioned that the breast stem cell of the present invention may be genetically modified. Said genetic modification can be caused by stable or transient introduction of various genetic elements, (e.g., viral vectors, plasmids, extrachromosomal replicating vectors, etc.) encoding one or more genes, e.g. the catalytic subunit of the human telomerase holoenzyme (hTERT) to generate immortalized cell lines. Such cell lines can be further genetically modified and transformed, e.g. by introducing the Simian Virus 40 (SV40), Large T antigen encoding gene, and the haRAS oncogene. In some embodiments, gene expression of one or more genes may be knocked-out by insertional mutagenesis using e.g. restriction enzymes or genetic elements which are inserted in the coding region or down-regulated by genetically modifying cells to express a short hairpin RNA (shRNA), microRNA (miRNA) or miRNA precursor, miRNA sponge, etc. It will be appreciated that a variety of different oncogenes and/or tumor suppressor genes can be used to genetically modify cells. One of skill in the art would be aware of suitable vectors and genetic elements (e.g., regulatory elements such as promoters, enhancers, etc.) for transfection of mammalian cells. In some embodiments, a regulatable (e.g., inducible and/or repressible) expression control element (e.g., promoter) is used to achieve regulatable expression of an RNA or protein of interest in cells.

The invention thus also provides a multicellular organoid unit that morphologically and/or functionally resembles the terminal ductal-lobular unit, comprising breast stem cells of the present invention.

Compound Testing

The breast stem cell or the multicellular organoid unit obtainable by the methods of the present invention can advantageously be used to test a variety of compounds for their potential to elicit a cellular response on said breast stem cell or multicellular organoid unit. A "cellular response" can be the frequency of a certain type of cell, cell growth (size of cell), cell proliferation, growth arrest, cell survival, apoptosis, necrosis, autophagy, senescence, DNA damage, differentiation, de-differentiation, trans-differentiation, migration, invasion, self-renewal, oncogenesis, and changes in the morphology of cells in the multicellular structure pertaining to: cell-cell adhesion, cell-matrix adhesion, apical-basal polarity, planar polarity as well as gene expression, regulatory RNA expression, protein expression, changes in metabolism, andothers. Cellular responses can be assessed using standard protocols known in the art. Compounds that can be tested for their ability to provoke a cellular response include a drug, hormone, growth factor, antibody, nucleotide molecule, peptide, protein or (co-cultured) cell.

A method for testing a compound for its ability to elicit a cellular response according to the invention comprises the following steps:
(i) bringing a breast stem cell or a multicellular organoid unit obtained by the above-described methods of the invention into contact with said compound; and
(ii) determining whether said compound elicits a cellular response.

Pharmaceutical Composition

Further, the present invention relates to a composition comprising a breast stem cell or the multicellular organoid unit as disclosed herein.

Said composition can be a pharmaceutical composition. The term "pharmaceutical composition" particularly refers to a composition suitable for administering to a human or animal, i.e., a composition containing components which are pharmaceutically acceptable. In particular, a pharmaceutical composition comprises a breast stem cell or a multicellular organoid unit as described herein together with a carrier, diluent or pharmaceutical excipient such as buffer, preservative and tonicity modifier. Pharmaceutical compositions of the invention comprise a therapeutically effective amount of a breast stem cell or a multicellular organoid unit and can be formulated in various forms, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for topical or oral administration.

The pharmaceutical composition may further comprise a solvent such as water, a buffer for adjusting and maintaining the pH value, and optionally further agents for stabilizing the breast stem cell or multicellular organoid unit C or preventing degradation of the same. It may additionally comprise further breast stem cells or multicellular organoid units, other pharmaceutically active agents, such as adjuvants etc.

By "therapeutically effective amount" is meant an amount of breast stem cells or multicellular organoid units that elicit the desired therapeutic effect. The exact amount dose will depend on the purpose of the treatment, and will be ascertainable by one skilled in the art using known techniques. As is known in the art and described above, adjustments for age, body weight, general health, sex, diet, drug interaction and the severity of the condition may be necessary, and will be ascertainable with routine experimentation by those skilled in the art.

A variety of routes are applicable for administration of the pharmaceutical composition, including, but not limited to, orally, topically, transdermally, subcutaneously, intravenously, intraperitoneally, intramuscularly or intraocularly. However, any other route may readily be chosen by the person skilled in the art if desired.

Binding Molecules

As set out elsewhere herein, the present inventors have for the first time found a combination of surface markers that allow for enrichment of breast stem cells having TDLU-like structure formation potential. Said markers can be detected by binding molecules. The present invention thus also relates to the use of binding molecules directed against CD31, CD45, EpCAM, CD49f and CD10 for enriching breast stem cells from a population of primary mammary epithelial cells.

The term "binding molecule" as used herein in general refers to any molecule able to recognize and bind to CD31, CD45, EpCAM, CD49f or CD10, and in particular includes antibodies or functional fragments thereof such as Fab or F(ab)2 or antibody derivatives such as bispecific antibodies (for example, scFvs), chimeric antibodies, humanized antibodies, single domain antibodies such as VHH antibodies (also known as Nanobodies) or domain antibodies (dAbs) or an lipocalin muteins (also known as anticalins) and others.

It is in particular envisaged that the binding molecules are employed to enrich $CD31^-$, $CD45^-$, $EpCAM^-$, $CD49f^+$ and $CD10^+$ cells. As described elsewhere herein, enrichment of cells having the desired combination of markers can be accomplished using standard protocols known in the art such as FACS as described in the appended examples.

Accordingly, the present invention also provides a method of enriching breast stem cells from a population of primary mammary epithelial cells, comprising
(i) sorting cells for the cell surface marker combination $CD31^-$, $CD45^-$, $EpCAM^-$, $CD49f^+$ and $CD10^+$.

Said method may further comprise the following steps:
(ii) culturing sorted cells in a collagen gel for at least 7 days, said culture medium comprising a compound which elevates cAMP levels;
(iii) determining whether a multicellular organoid unit is formed in step (ii); and
(iv) obtaining a single cell form said multicellular organoid unit of (iii).

It will be appreciated that method steps (ii)-(iv) correspond to method steps (i)-(iii) of the method for generating cells capable of differentiating into multicellular organoid structures also described in detail elsewhere herein. Hence, the definitions and explanations with regard to the latter are also applicable to the method for enrichment of breast stem cells, mutatis mutandis.

Breast stem cells can also be enriched from a population of cells from mammary epithelial tissue by a method comprising the step(s) of
(i) determining whether cells from said population of cells from mammary epithelial tissue are capable of forming a multicellular organoid unit in a collagen-I gel in the presence of a compound which elevates cAMP levels after at least 7 days and/or (ii) determining whether said multicellular organoid unit is capable of contracting a floating collagen-I gel.

Again, in step (i) determination of whether a multicellular organoid unit is formed is accomplished by assessing the presence of ductal structures and multiple branch-points in said multicellular organoid unit. As described elsewhere herein, it is contemplated that capability of the multicellular organoid unit to contract the floating gel (step (ii)) is indicative of alveologenesis.

As described in greater detail in the context of other methods of the invention, the culture medium may comprise a Rho-kinase (ROCK) inhibitor, said ROCK inhibitor being either unspecific or specific for either ROCK1 and/or ROCK2. It is in particular envisaged that the ROCK inhibitor is Y-27632 or Thiazovivin and the compound which elevates cAMP levels, is an adenylylcyclase agonist such as Forskolin.

Progenitor Cells

Furthermore, the inventors discovered that luminal progenitor cells may be cultured, similar to breast stem cells, in a collagen gel. Without wishing to be bound by theory, luminal progenitor cells may be the cells-of-origin for breast cancer. In contrast to breast stem cells, luminal progenitor cells typically form spheres when cultured in a collagen gel. However, in rare cases luminal progenitor cells de-differentiate spontaneously and thereby acquire stem-cell attributes resulting in the generation of branched structures, in particular multicellular organoid units, in a collagen gel. Upon de-differentiation luminal progenitor cells down-regulate the expression of the cell lineage markers CK8, CK18, GATA3 and up-regulate the expression of Vimentin. De-differentiation of luminal progenitor cells is indicative of an abnormality and may be a first step in the development of breast cancer. Hence, the de-differentiation capacity of luminal progenitor cells may indicate an increased breast cancer risk.

Accordingly, the present invention relates to a method for determining the rate of spontaneous de-differentiation of luminal progenitor cells, comprising:

(i) enriching a luminal progenitor cell containing population by sorting the cells for the cell surface marker combination $CD31^-$, $CD45^-$, $EpCAM^+$, $CD49f^+$;

(ii) culturing said cells in a collagen gel, in particular a collagen I gel; and (iii) determining whether a multicellular organoid unit is formed in step (ii).

Means and methods for determining whether a multicellular organoid unit is formed have been described elsewhere herein and are applicable mutatis mutandis.

Furthermore, the present invention relates to a method for generating a de-differentiated luminal progenitor cell, comprising:

(i) enriching luminal progenitor cell containing population by sorting the cells for the cell surface marker combination $CD31^-$, $CD45^-$, $EpCAM^+$, $CD49f^+$;

(ii) culturing said cells in a collagen gel;

(iii) determining whether a multicellular organoid unit is formed in step (ii); and (iv) obtaining a single cell from the multicellular organoid unit.

The culture medium used for luminal progenitor cells may comprise a Rho-kinase (ROCK) inhibitor, said ROCK inhibitor being either unspecific or specific for either ROCK1 and/or ROCK2 and/or a compound which elevates cAMP levels, as described herein.

Furthermore, the luminal progenitor cells may be dissociated cells from mammary epithelial tissue, wherein said epithelial tissue is healthy or diseased tissue, wherein said diseased mammary epithelial tissue comprises germ-line or somatic mutations.

Luminal progenitor cells, obtainable as described herein, can be used for testing a compound, such as a drug, hormone, growth factor, antibody, nucleotide molecule, peptide, protein or (co-cultured) cell and others. Upon treatment, the de-differentiated luminal progenitor cells may show a cellular response, e.g., frequency of a certain type of cell, cell growth (size of cell), cell proliferation, growth arrest, cell survival, apoptosis, necrosis, autophagy, senescence, DNA damage, differentiation, de-differentiation, trans-differentiation, migration, invasion, self-renewal, oncogenesis, and changes in the morphology of cells in the multicellular structure pertaining to: cell-cell adhesion, cell-matrix adhesion, apical-basal polarity, planar polarity as well as gene expression, regulatory RNA expression, protein expression, changes in metabolism, and others. The luminal progenitor cells can thus be used a tool for testing compounds for their potential to modulate cellular responses as described herein. Provided herein is therefore the use of luminal progenitor cells for testing compounds, e.g. for their potential to induce or inhibit differentiation and/or de-differentiation, thereby e.g. assessing their carcinogenic potential. For example, compounds capable of inhibiting differentiation and/or inducing de-differentiation may be potentially cancerogenous compounds. Methods for determining the cellular responses such as differentiation and de-differentiation are well-known in the art and include, e.g., microscopy, PCR techniques such as real-time PCR or digital PCR, cell sorting/flow cytometry, immunocytochemistry, western blotting, and biomarker analysis.

Another potential use for the de-differentiated luminal progenitor cells is their use as a preclinical model of invasive breast cancer.

EXAMPLES

The following Examples illustrate the invention, but are not to be construed as limiting the scope of the invention.

I. Experimental Procedures

1. Isolation and Culture of Human Mammary Epithelial Cells

Mammary gland tissue was obtained from healthy women undergoing reduction mammoplasty at the Nymphenburg Clinic for Plastic and Aesthetic Surgery (Christian Gabka), in accordance with the regulations of the ethics committee of the Ludwig-Maximilian University Munich (proposal 397-12). Single cell suspensions of primary HMEC were generated as previously described with minor modifications (Stingl et al., 2005). Briefly, the ductal tree was minced into about 1.0 $mm^3$ pieces and digested in collagenase I and hyaluronidase (both Sigma), and subsequently with Trypsin-EDTA and dispase (Life Technologies), and then cryopreserved. Before further processing, cells were filtered through a 40 µm strainer, to remove residual tissue fragments and cell aggregates. Cells were seeded in 2D on polystyrene cell culture plates or in collagen I gels in Mammary Epithelial Cell Growth Medium (MECGM, PromoCell) supplemented with 1% Pen/Strep (Invitrogen), 0.5% FCS (Pan Biotech), 3 µM Y-27632 (Biomol) and 10 µM Forskolin (Biomol), unless stated otherwise. After an establishment period of 5 days, medium was changed to MECGM supplemented with 1% Pen/Strep and 10 µM Forskolin, unless stated otherwise.

2. 3D-Collagen I Gels

Single cell suspensions containing the desired amount of cells were quickly mixed with neutralizing solution, and acidified rat tail collagen I (Corning) was added, resulting in a final collagen I concentration of 1.3 mg/ml. Next, the gel mixture was plated into siloxane-coated 24-well or 48-well plates. After polymerization of the gel, medium with supplements was carefully added and gels were detached from the well. Attached and attached-to-floating gels were prepared in uncoated 24-well plates. Cells were maintained for 8 up to 20 days (shorter periods for quantification and longer periods for long term treatments).

3. Extreme Limiting Dilution Analysis (ELDA)

For determination of structure-forming units (SFU), limiting dilution collagen gels with at least 6 gels per cell-dose were prepared in 48-well plates, as described above. Structures were stained with Carmine solution and were imaged on a Zeiss SteREO Lumar.V12 microscope with a NeoLumar S 0.8× objective (10-20× Zoom). Gels with at least one branched structure were counted as positive. Branched structures were defined as containing branching points and being $\geq 0.057$ mm$^2$ in size. Limiting dilutions were analyzed using a webtool, as described previously (Hu and Smyth, 2009).

4. Immunofluorescence

Cells were fixed with 4% paraformaldehyde. For immunofluorescence, cells were permeabilized with 0.2% Triton X-100 and blocked with 10% goat or donkey serum in 0.1% BSA. Primary and secondary antibodies used for stainings are listed in Tables 3 and 4, respectively. Cell nuclei were visualized with DAPI.

5. Flow Cytometry and Fluorescence-Activated Cell Sorting (FACS)

Single cell suspensions of HMEC were stained with CD31-PB, CD45-V450, CD49f-PE, EpCAM-FITC, and CD10-APC antibodies (see Table 5). Prior to sorting, 7AAD (BD Biosciences) was added to distinguish dead and live cells. After excluding 7AAD$^+$ and CD31$^+$/CD45$^+$ (Lin$^+$) cells, HMEC were sorted into three or four populations (LP: CD49f$^+$/EpCAM$^+$, B: CD49f$^{hi}$/EpCAM$^-$, B−: CD10$^-$/CD49f$^{hi}$/EpCAM$^-$ and B+: CD10$^+$/CD49f$^{hi}$/EpCAM) using a FACS Aria III (BD Biosciences). The separated populations were re-analyzed to ensure the purity of the sort. FlowJo V10 was used for post-analysis.

6. Expression Profiling and Statistical Transcriptome Analysis

Total RNA from freshly sorted HMEC from Donors M3, M6, M8, M9, M10 and M12 was amplified using the Ovation Pico WTA System V2 in combination with the Encore Biotin Module (Nugen). Amplified cDNA was hybridized on Affymetrix Human Gene 2.0 ST arrays. Array data has been submitted to GEO (GSE64248).

7. Statistical Analysis

Data are presented as mean±standard deviation (SD) except for SFUs which are shown as mean and 95% confidence intervals (CI). The student's t test (two-tailed, unpaired) was used to compare two groups. A p-value p<0.05 was considered significant; *p<0.05, p<0.005, *p<0.0005.

8. Expanded Procedure: Isolation and Culture of Human Mammary Epithelial Cells

Mammary gland tissue was obtained from healthy women undergoing reduction mammoplasty at the Nymphenburg Clinic for Plastic and Aesthetic Surgery (Prof. Christian Gabka), in accordance with the regulations of the ethics committee of the Ludwig-Maximilian University Munich (proposal 397-12). Single cell suspensions of primary HMEC were generated as previously described with minor modifications (Stingl et al., 2005). Briefly, the ductal tree was minced into about 1 mm$^3$ pieces and enzymatically digested in tissue digestion buffer (F12:DME/HEPES, 1.5% w/v BSA) supplemented with 1 µg/ml insulin, 300 U/ml collagenase and 100 U/ml hyaluronidase (all Sigma) at 37° C. over night. The stromal compartment was optionally separated by differential centrifugation and cryopreserved. The pellet enriched for epithelial cells was further dissociated in 0.15% Trypsin-EDTA and 5 mg/ml dispase (Life Technologies) and then cryopreserved. Before further processing, cells were filtered through a 40 µm strainer, to remove residual tissue fragments and cell aggregates. Freshly isolated primary HMEC were seeded in Mammary Epithelial Cell Growth Medium (MECGM, PromoCell) supplemented with 1% Pen/Strep (Invitrogen), 0.5% FCS (Pan Biotech), 3 µM Y-27632 (Biomol) and 10 µM Forskolin (Biomol), unless otherwise stated. After an establishment period of 5 days, medium was changed to MECGM supplemented 1% Pen/Strep and 10 µM Forskolin, unless otherwise stated. Upon establishment, medium was replaced every 3-4 days. Cells were maintained in 5% CO2, 3% O$_2$ for the whole culture period.

9. Expanded Procedure: 3D-Collagen Gels

In case of floating collagen gels tissue culture plastics were siloxane-coated by pretreatment with a solution of 25 g/l dichloro-octamethyltetrasiloxane (Santa Cruz, sc-229834) in n-heptane (Applichem, #1948) for approximately 30 seconds and subsequently rinsed one time each with PBS and water. Siloxane-coating facilitates detachment of gels. For attached or attached-to-floating collagen gels the culture plates were left uncoated.

Three-dimensional floating collagen gels were prepared based on a published protocol (Wozniak and Keely, 2005) with modifications described below.

Neutralizing solution (11×PBS, 550 mM HEPES, comprising $\frac{1}{10}^{th}$ of the volume of collagen) was added to a single cell suspension in growth medium containing the desired amount of cells. Quickly, acidified rat tail collagen type I (Corning) was added, resulting in a final concentration of collagen of 1.3 mg/ml. Next, the gel mixture was quickly plated into 24-well (400 µl) or 48-well (200 µl) tissue culture plastics on ice and left to polymerize at 37° C. for 1 hour after which 600 µl (24-well plate) or 300 µl (48-well plate) medium with supplements was carefully added. The concentrations of supplements were calculated for the total volume of the gel with medium.

In case of floating collagen gels, the gels were detached from the well by encircling them with a pipet tip followed by gently shaking the plate. Cells were cultured for 8 up to 20 days.

For improvement of culture conditions, 1×10$^4$ HMEC/400 µl collagen gel were seeded.

For comparison of structure formation by 9 different donors in passage 0 and in passage 2, 2×10$^4$ HMEC/400 µl collagen gel and 8×10$^2$ HMEC/400 µl collagen gel were plated, respectively.

For contraction assays, 5×10$^3$ HMEC were plated or 3×10$^3$ sorted B+ cells/400 µl collagen gel and 1×10$^4$ LP cells/400 µl collagen gel. At day 12 of culture, 2 ng/µl TGF-β1 (R&D Systems) was added to the culture medium once. For inhibition of contraction experiments, 3×10$^3$ HMEC (Donor M10) were plated/400 µl collagen gel, and the gels were left attached to the culture dish. At day 13 of culture, when structures had formed, gels were detached and 10 µM Blebbistatin or 5 µM Y-27632 were added to the culture medium every 24 hours. To determine the number of cells per gel, collagen gels were minced using a scalpel, digested with 300 U/ml collagenase I (Sigma) for 1 hour at 37° C., followed by 0.15% trypsin (5 minutes at 37° C.), and filtered to obtain single cells. Cells were counted with a hemocytometer. Images of structures in the gels were acquired on a Leica DM IL LED microscope equipped with a HiPlan 10×/0.22 PH1 objective and images of whole gels were taken with a Zeiss SteREO Lumar.V12 microscope with a NeoLumar S 0.8×objective (6.4× Zoom).

10. 3D-Matrigel Culture

Single cells were resuspended in Growth Factor Reduced Matrigel (Corning), plated into 24-well plates on ice (400 µl/well) and Matrigel was left to polymerize at 37° C. for 1 hour. After this, medium was added and gels were treated like the 3D-collagen gels.

11. Expanded Procedure: 2D-Immunofluorescence

Cells grown on poly-D-lysine-coated glass coverslips were fixed with 4% paraformaldehyde for 15 minutes, permeabilized with 0.2% Triton X-100 for 2 minutes, and then blocked with 10% goat or donkey serum in 0.1% BSA for 1 hour. Slides were incubated with primary antibodies in 0.1% BSA for 1 hour, followed by incubation with secondary antibodies in 0.1% BSA for 2-3 hours. Cell nuclei were stained with 167 ng/ml DAPI. Coverslips were mounted with AQUA-POLY/MOUNT mounting medium (Polysciences). All steps were performed at room temperature. Images were acquired on an Axioplan 2 imaging light/fluorescence microscope using a 20× objective and processed with Axiovision Rel 4.7 and Gimp 2.8.2/Adobe Photoshop CS5 software.

12. Expanded Procedure: 3D-Immunofluorescence

Cells in 3D collagen gels were washed with PBS for 10 minutes, fixed with 4% paraformaldehyde for 15 minutes, washed with PBS for 10 minutes, quenched with 0.15 M Glycine for 10 minutes, and washed again with PBS for 10 minutes. Then, cells were permeabilized with 0.2% Triton-X-100 for 10 minutes and washed with PBS for 10 minutes. Cells were blocked with 10% goat or donkey serum (both Biozol) in 0.1% BSA for 3 hours at room temperature or overnight at 4° C. After washing with PBS for 10 minutes, gels were incubated with primary antibodies in 0.1% BSA at 4° C. overnight. Gels were washed with PBS three times for 10 minutes and incubated with secondary antibodies in 0.1% BSA for 2-3 hours at room temperature, followed by further two times washing with PBS for 10 minutes (for antibodies, see Tables 3,4). Cell nuclei were stained with 167 ng/ml DAPI (Sigma) for 2 minutes. Then, gels were washed with PBS three times for 10 minutes and with water two times for 5 minutes. The fixation, quenching, permeabilization, and all washing steps were performed at room temperature on a shaker. Collagen gels were transferred to a microscope slide, excess liquid was removed with a tissue, and mounted with AQUA-POLY/MOUNT mounting medium (Polysciences). Samples were imaged on an inverted confocal laser scanning microscope equipped with 4 laser lines (405, 488, 543, and 633 nm) and UPLSAPO 60×, 40× and 20× objective lenses. FV-10-ASW 1.7 Viewer and Gimp 2.8.2/Adobe Photoshop CS5 software were used to adjust brightness across the entire image field.

13. Immunohistochemistry

For immunohistochemistry, collagen gels were fixed in 4% paraformaldehyde and embedded in paraffin. Staining was performed on 2 µm thick sections according to manufacturer's recommendations and standard protocols. Antibodies are listed in Table 3 and were detected with the ultraView Universal DAB Detection Kit (Roche). For hematoxylin and eosin staining, formalin-fixed and paraffin-embedded (FFPE) breast tissues from cosmetic breast reduction surgeries were selected from the tissue archives of the Institute of Pathology, Ludwig-Maximilians-University Munich, Munich, Germany. 2 µm thick H&E-stained sections were examined by two pathologists for no evidence of dysplasia or malignancy. Tissue samples had been anonymized according to the local ethics committee regulations.

14. Carmine Staining

Carmine-alum solution was prepared according to standard protocols. Collagen gels were fixed with 4% paraformaldehyde, as described above, and were incubated in Carmine solution on a shaker overnight at room temperature and then mounted with Roti-Aqua Mount (Roth). Structures in gels were imaged on a Leica DM IL LED microscope with a HiPlan 10×/0.22 PH1 objective and whole mount pictures were taken with a Zeiss SteREO Lumar.V12 microscope with a NeoLumar S 0.8× objective (10-20× Zoom).

15. RNA Preparation and Quantitative PCR Analysis

After homogenization using the QIAshredder, RNA was isolated with the RNeasy Mini Kit in combination with the RNase-Free DNase Set (all Qiagen), according to manufacturer's instructions. RNA was reverse transcribed using the EasyScript Plus cDNA Synthesis Kit (Abm) according to the manufacturer's Oligo(dT) protocol. In case of small amounts of RNA, total RNA was amplified using the Ovation Pico WTA System V2 in combination with the Encore Biotin Module (Nugen). Real-Time quantitative PCR was performed with the Power SYBR Green PCR Master Mix (Life Technologies) on a QuantStudio 12K Flex qPCR System. Data were analyzed using the $\Delta Ct$ method to present data as fold change expression compared to the housekeeping gene RPL32 (Schmittgen and Livak, 2008) Primers are listed in Table 2.

16. Morphological Analysis of Gels, Structures and Cells

Size of gels, structures, and cells was determined with the ImageJ tool for measurement of areas. Quantification of structures was carried out using the ImageJ cell counter. Structures with at least two branching points were considered as branched. For branching point analysis, branches were traced, one main branch was set, and one branching point was counted for each side-branch.

17. Plasmids, Virus Production and Infection of Target Cells

The mCherry coding sequence was amplified using primers mCherry_XbaI_FW (ttTCTAGAcaggatcccgccaccatg) and mCherry_SaII_RV (ttGTCGACttacttgtacagctcgtccatgc) and cloned into pRRL.SIN.cPPT.CMV-GFP.WPRE (gift from Timm Schröder, ETH Basel, Switzerland) using XbaI and SalI. HEK293T high performance cells (ATCC) were transfected with pMD2.G (Addgene plasmid 12259), psPAX2 (Addgene plasmid 12260), and pRRL coding either for GPF or mCherry. Cell-free supernatants were collected during 48 hours and 1 ml of lentiviral suspension were applied to a 10 cm dish of HMEC passage 0, in the presence of 3.3 µg/ml protamine sulfate. After 4 hours, cells were trypsinized and seeded into floating collagen gels.

18. Expanded Procedure: Expression Profiling and Statistical Transcriptome Analysis Total RNA from freshly sorted HMEC from donors M3, M6, M8, M9, M10, M12 was amplified using the Ovation Pico WTA System V2 in combination with the Encore Biotin Module (Nugen). Amplified cDNA was hybridized on Affymetrix Human Gene 2.0 ST arrays. Staining and scanning was done according to the Affymetrix expression protocol including minor modifications as suggested in the Encore Biotion protocol. Expression console (v.1.3.0.187, Affymetrix) was used for quality control and to obtain annotated normalized RMA gene-level data (standard settings including median polish and sketch-quantile normalization). Statistical analyses were performed by utilizing the statistical programming environment R (R Development Core Team, 2008) implemented in CARMAweb (Rainer et al., 2006). Genewise testing for differential expression was done employing the (limma) t-test and Benjamini-Hochberg multiple testing correction (FDR<10%).

To reduce the background, sets of regulated genes were filtered for average expression>10 in at least one of the three groups. Heatmaps were generated with CARMAweb and GO term and pathway enrichment analyses (p<0.01) were done with GePS (Genomatix). Array data has been submitted to GEO (GSE64248).

II. Results

Example 1: Identification of Culture Conditions That Promote Generation of TDLU-Like Structures by Freshly Dissociated HMEC To develop a 3D-culture system in which HMEC recapitulate morphogenesis, collagen type I was chosen as a substrate. On the one hand, collagen I constitutes a main component of extracellular matrix in the human MG and provides an environment of defined composition. On the other hand, its physical properties can be modified and supplemented to model different microenvironments. To generate hydrogels for 3D-culture, it was built on observations that a breast carcinoma cell line generated tubular structures when cultured in collagen gels that freely float in the growth medium (FIG. 1A; Experimental Procedures; (Wozniak and Keely, 2005). Within a period of 10-12 days, freshly isolated single-cell suspensions of HMEC cultured in freely floating collagen gels gave rise to a variety of multicellular structures that were subdivided into 3 types of branched (TDLU-like, thin, star) and 3 types of non-branched structures (stick, sphere, multi-sphere, FIG. 1B). The TDLU-like structures were labeled as such, because they displayed side-branched ducts with rounded, alveolar tips, similar to the morphology of TDLU in situ (FIG. 1B,C). TDLU are histological units of the breast consisting of a cluster of up to 100 alveoli, i.e. round buds at the tips of branches, and a small segment of the terminal duct that drains into larger ducts, leading to the nipple. Because TDLU are the functional units of the MG, the focus was on characterizing cells and conditions enabling the formation of these particular organoids.

Since only about 1 in 2000 primary HMEC plated into the gels was able to generate any of the branched-type structures (FIG. 1D), firstly, culture conditions were sought to be improved. Recent studies have shown that inhibitors of Rho-associated kinase (ROCK) increase colony formation in 2D- and 3D-culture, and allow for the acquisition of regenerative capacity by mouse MEC (Guo et al., 2012; Makarem et al., 2013; Prater et al., 2014). Thus, ROCK inhibitor Y-27632 was added to the growth medium upon plating of freshly dissociated cells to promote initial survival. After a period of 5 days, the growth medium was replaced and the ROCK inhibitor removed. It could be observed that treatment with 3 μM of the ROCK inhibitor Y-27632 increased branched structure formation by approximately 5-fold (FIGS. 1D, 8A). Similar observations were made with Thiazovivin, another ROCK inhibitor (FIG. 8A). Importantly, higher concentrations of ROCK inhibitors led to formation of star-like agglomerations and loss of TDLU-like branched structures (FIG. 8B). Continuous treatment with Y-27632 after 5 days of initial culture resulted in dissolution of cell-cell adhesion, thereby perturbing morphogenesis (data not shown).

Though addition of ROCK inhibitors increased formation of branched structures, it was visible that these were thin in diameter with few alveoli at their tips (FIG. 1D). To increase alveologenesis, Forskolin was added to the growth medium, an agonist of Protein Kinase A, to increase intracellular cAMP levels (Fradkin et al., 1982). Compounds that raise cAMP levels are in widespread use for epithelial cultures (Stampfer, 1982) and promote polarization and lumen formation in spheres derived from MCF10A mammary epithelial cells (Nedvetsky et al., 2012). Indeed, the addition of 10 μM Forskolin promoted the formation of TDLU-like branched structures by approximately 12-fold, while overall branched structure-forming potential was increased 3-fold (FIGS. 1D, 8A,B). Formation of non-branched structures (mostly spheres) was only slightly increased (approximately 1.5-fold, FIG. 8C). Together, these results indicated that Forskolin promotes the formation of alveolar buds in branched structures. In conclusion, treatment with 3 μM Y-27632 during initial establishment of the organoid cultures and continuous treatment with 10 μM Forskolin was used as standard condition for all experiments, unless stated otherwise. Under these conditions, the predominant types of structures generated by freshly isolated HMEC were TDLU-like branched structures and spheres.

Matrigel, a basement membrane protein mixture derived from murine sarcoma cells, is a commonly used substrate for the 3D-culture of mammary epithelial cells (Benton et al., 2014; Mailleux et al., 2008). To determine whether experiments performed in collagen gels were comparable to those performed in Matrigel, HMEC was seeded into Matrigel while not changing any of the other parameters. Strikingly, Matrigel did not support the growth of freshly isolated HMEC (data not shown). Indeed, it has been argued that primary HMEC need to be established in 2D-culture before cultivation in Matrigel (Dontu et al., 2003) or, alternatively, need support by stromal cells (Eirew et al., 2008).

Example 2: Single HMEC Give Rise to TDLU-Like Structures in Floating Collagen Gels Single murine MEC are able to repopulate a mouse mammary fat pad cleared of endogenous epithelium (Shackleton et al., 2006; Stingl et al., 2006). HMEC with comparable repopulating potential were identified by transplantation under the renal capsule of NOD-SCID mice, where they generated epithelial structures (Eirew et al., 2008). Thus, to test for clonality of TDLU-like structures, a portion of freshly isolated HMEC was labeled with eGFP or mCherry fluorescent protein by lentiviral transduction before plating cells in decreasing concentrations. After 8 days of culture, nuclei were stained with DAPI to determine the frequency of clonal (complete overlap of eGFP or mCherry with DAPI) and polyclonal structures (eGFP or mCherry with areas of DAPI-only staining) by confocal microscopy. In gels containing 500 cells, 67% of the positive structures showed a complete overlap of eGFP or mCherry with DAPI, suggesting that they were derived from a single cell. At higher cell densities (4500-13500 cells/gel), up to 100% of structures were positive for cells labeled with eGFP or mCherry together with DAPI-only areas, and thus were derived from more than one cell (FIG. 1E). Interestingly, in the majority of multicolored structures, one part of the structure was uniformly positive for eGFP or mCherry, whereas the other part was DAPI-only, suggesting that they were the result of two monoclonal structures that had merged (FIG. 1F, middle). A minority of multicolored structures exhibited eGFP or mCherry positive areas intermingled with DAPI-only areas, suggesting that multiple cells had merged at the very beginning of structure formation (FIG. 1F, right). Together, these observations demonstrated that single HMEC give rise to TDLU-like structures in floating collagen gels when seeded at low densities and that generally, TDLU-like structures do not arise from collaboration of cells at the beginning of structure formation.

Example 3: Maintenance and Expansion of TDLU-Like Structure Formation During Passaging and 2D-Culture To test for the presence of HMEC with regenerative capacity over multiple passages, collagen gels were enzymatically digested to yield single cell suspensions, which were re-plated into floating collagen gels. Formation of branched structures over 2 such passages could be observed (FIG. 9A). After passage 2, 3D-cultured HMEC predominantly generated spheres, suggesting a loss of regenerative, but not proliferative capacity (data not shown). Genetic manipulation is facilitated by cultivation of cells in 2D- rather than 3D-culture. Therefore, it was tested whether the capacity to form TDLU-like structures is maintained in 2D-culture. For this purpose, cells were cultured on polystyrene cell culture dishes and plated into floating collagen gels at passage 1, 3 and 5 to determine TDLU-like structure-forming units by Extreme Limiting Dilution Analysis (ELDA; FIG. 2A; (Hu and Smyth, 2009). In passage 1 and 3, branching potential was comparable, with ~1/290 and ~1/250 cells giving rise to a TDLU-like structure, respectively (FIG. 2B,C). However, TDLU-like structure formation dramatically decreased by passage 5. It could be noted that HMEC exhibited an epithelial morphology in 2D-culture (FIG. 9B,C). Since mesenchymal, rather than epithelial traits, have been associated with stemness in basal populations of murine and human MEC (Mani et al., 2008; Morel et al., 2008), induction of an Epithelial-Mesenchymal Transition (EMT) might promote regenerative capacity. Forskolin promoted an alveolar, more differentiated phenotype of branched structures in floating collagen gels. Therefore, it was tested whether it inhibited mesenchymal attributes in 2D-culture. Indeed, in the absence of Forskolin, HMEC cultured in 2D spontaneously acquired mesenchymal attributes, as evidenced by acquisition of front-to-back polarization, downregulation of E-cadherin expression at the protein level and upregulation of mesenchymal markers at the protein and transcript level (FIG. 9B-D).

To assess whether the mesenchymal phenotype led to increased formation of TDLU-like structures, cells were again transferred from 2D-culture to floating collagen gels in limiting dilution for passage 1, 3 and 5. Surprisingly, while proliferating vigorously in 2D-culture without Forskolin, cells transferred to floating collagen gels generated only a few loose cell agglomerations (FIG. 2D,E). Immunofluorescence revealed that cells maintained a mesenchymal phenotype, remained negative for E-cadherin and positive for vimentin expression (FIG. 2E). These results suggested that HMEC depend on repression of mesenchymal transdifferentiation to manifest regenerative potential. The transcription factor OVOL2, a negative regulator of EMT-associated genes, has recently been found essential for morphogenesis and regeneration in the mouse MG (Watanabe et al., 2014). At passage 1, transcript levels of OVOL2 were similar in HMEC cultured both with and without Forskolin. However, after passage 1, the expression of OVOL2 started to decrease dramatically in HMEC cultured without Forskolin (FIG. 9E). Similar dynamics of repression at the transcript and protein level were observed for ITGA6/integrin-α6 (CD49f), a cell surface marker for basal and luminal progenitors (FIG. 9E,F). In summary, HMEC cultured in 2D without Forskolin upregulate expression of mesenchymal genes, followed by downregulation of the epithelial gatekeeper OVOL2 and ITGA6. Together, these results indicate that upregulation of mesenchymal genes during spontaneous EMT in 2D-culture may directly interfere with regenerative capacity of HMEC, as loss of TDLU-like structure formation precedes the downregulation of epithelial cell-fate determinants.

Example 4: Frequency of TDLU-Like Structure-Forming Cells Varies Between Donors and is Increased by 2D-Culture HMEC from individual donors may behave differently due to genetic background, age and parity, and may be particularly responsive to changes in hormone status (Tanos et al., 2012). To determine the level of reproducibility for observations made with cells from one donor tissue to another, TDLU-like structure formation of 9 donors were compared, representing different ages (17-71 years) and parity (0-2, Table 1). As expected, structure-forming potential was very heterogeneous (FIG. 3A-C). For example, cells from donor tissue M1 almost exclusively formed spheres, whereas M7 exhibited high TDLU-like structure but relatively low sphere formation (FIG. 3A-C). To quantify representative TDLU-like-Structure Forming Units (B(ranched)-SFU) and Sphere-Structure Forming Units (S-SFU), an ELDA was performed with a moderately TDLU-like structure- and sphere-forming donor tissue. Thereby, a B-SFU of 1/1005 and S-SFU of 1/55 were determined (FIG. 3D). In summary, these results show that heterogeneity between donors is reflected by differences in the frequency of cells that generate TDLU-like structures and spheres. Within the limited number of donor tissues analyzed so far, these effects appeared to be independent of age or parity.

Next, it was determined whether HMEC from all donors maintained structure-forming ability following establishment in 2D-culture. For this purpose, HMEC were established in 2D-culture and then transferred to floating collagen gels. Both freshly isolated and 2D-cultured HMEC generated TDLU-like structures with similar morphologies, suggesting that short-term 2D-culture did not significantly change cell behavior (FIG. 3A,E). Interestingly, it could be observed that 2D-culture increased the formation of TDLU-like structures on average by ~12 fold and the formation of spheres by ~4 fold (FIG. 3F,G). This observation might be largely due to the fact that approximately 50% of freshly isolated HMEC are not viable, as determined by 7-AAD labeling (FIG. 3H). Given the overnight processing of tissue required for dissociation of the human MG, this amount of cell death is expected. Consequently, many of the freshly isolated HMEC plated will not generate structures, resulting in underestimation of TDLU-like structure-forming potential. In addition, these data suggest that either TDLU-like structure-forming cells expand preferentially or, alternatively, some HMEC acquired structure-forming ability de novo. In line with the latter hypothesis, it has recently been proposed that mouse myoepithelial cells acquire regenerative potential during 2D-culture in the presence of ROCK-inhibitor (Prater et al., 2014).

Example 5: TDLU-Like Structure-Forming Potential is Contained Within a CD10$^+$/CD49f$^{hi}$/EpCAM Basal Population MaSC have been shown to reside within the basal MEC population in both the human and murine MG (Shackleton et al., 2006; Stingl et al., 2006). Therefore, it was determined whether the size of the basal and luminal cell population, respectively, predicts the frequency of TDLU-like structure and sphere formation in floating collagen gels. Using Fluorescence Activated Cell Sorting (FACS), viable CD45$^-$/CD31$^-$ (Lin$^-$) cells were further subdivided based on CD49f and EpCAM expression, as previously described (FIG. 4A, (Eirew et al., 2008; Lim et al., 2009a). In line with existing data, mature luminal cells (termed LM, CD49f$^-$/EpCAM$^+$) did not show clonogenic activity in floating collagen gels (data not shown and (Lim et al., 2009b). Therefore, the focus was on the luminal progenitor (termed LP; CD49f$^+$/EpCAM$^+$) and basal population (termed B; CD49f$^{hi}$/EpCAM$^-$). Thus, respective proportions of LP and B populations within the Lin compartment of 9 donors (FIG. 10A) were correlated with organoid formation by freshly isolated bulk HMEC (FIG. 4B,C).

It was found that sphere formation correlated with the size of the LP population, but not with the size of the B population (FIG. 4B). This observation suggests that spheres predominantly arise from LP. However, neither the size of the LP, nor the size of the B population was predictive of TDLU-like structure formation (FIGS. 4C, 10B). Considering that regenerative capacity was shown to reside within the CD49f$^{hi}$/EpCAM$^-$ population (Eirew et al., 2008; Lim et al., 2009), it could be concluded that heterogeneity within the B population probably accounted for the missing correlation between size of the B population and TDLU-like structure formation.

To unravel regenerative capacity within the B population, expression of the cell surface metalloendopeptidase CD10 was analyzed, which was previously suggested as a potential MaSC-marker (Bachelard-Cascales et al., 2010). Two distinct subpopulations were found within the B population; the majority of cells were CD10$^-$ (referred to as B–) and a smaller subset was CD10$^+$ (referred to as B+, FIG. 4A). CD10$^+$ cells were also found among the stromal, LM and LP populations. However, TDLU-like structure formation correlated better with the size of the B+ population, than with the percentage of CD10$^+$ cells within these other populations (FIGS. 4C, 10C). To determine whether CD10 expression within the B population enriches for branching potential, sorted B+, B–, B and LP cell populations were plated in floating collagen gels for ELDA. Indeed, B-SFUs were enriched ~7-fold in the B+ population over the B population and ~30-fold over the B– population (FIG. 4D,E).

Together, these data demonstrate that CD10 enriches for B-SFU within the B population. It should be noted that the result of ELDA is likely a stark underestimation of true B-SFU. Furthermore, it can be estimated that at least 50% of viable HMEC die after sorting due to stress inflicted by the FACS-procedure, as was recently described for murine MEC (Prater et al., 2014).

Example 6: CD49f$^+$/EpCAM$^+$ Luminal Progenitor Cells Predominantly Form Spheres in Floating Collagen Gels LP cells from two donors, M9 and M10, gave rise to spheres, but did not generate any branched structures, as determined by ELDA. Interestingly, LP cells from donor M8 displayed TDLU-like structure-forming ability (FIG. 4E). The appearance of TDLU-like structures in LP-derived cultures could not be explained by contamination with other cells during the sorting procedure (FIG. 10D). Considering that this phenomenon was observed for one donor only, these data suggest that the LP population of this particular donor was more plastic and thereby able to acquire branching ability. Plasticity of LP cells has been described before: when transplanted under the renal capsule or into a humanized fat pad of immune compromised mice, human LP cells can give rise to structures containing both luminal and basal cells (Keller et al., 2010; Shehata et al., 2012). In conclusion, LP cells cultured in floating collagen gels predominantly give rise to spheres. However, under certain conditions, LP cells might become plastic and acquire the ability to generate more complex structures.

Example 7: CD10-Staining Reveals a Stromal Component within the CD49f$^{hi}$/EpCAM$^-$ Population ELDA demonstrated that sorting for the CD10$^+$ population within the B population enriched for cells with regenerative ability. To assess differences between B– and B+ cells at the phenotypic level, gene expression profiling was performed. For this purpose, freshly isolated cells from 6 donors of various age and parity were separated into B+, B– and LP populations by FACS (see FIG. 4A, Table 1). Principal component analysis (PCA) of global gene expression revealed 3 distinct clusters corresponding to these different populations (FIG. 5A). Thus, while sizes of the B+, B– and LP populations vary greatly between different donors (FIG. 10A), isolated populations cluster tightly across donors at the transcriptional level. In conclusion, robustness in function, i.e. structure formation, is reflected at the transcriptional level. Together, these results support the applicability of employing cell surface markers to isolate distinct subpopulations from primary HMEC in order to determine regenerative potential.

PCA confirmed that B– and B+ cells represent distinct populations. To understand the cellular identity of these populations, transcript levels of luminal and basal cell fate determinants were compared (FIG. 5B). As expected, basal genes (such as TP63 and ACTA2) were strongly upregulated within B+ compared to LP cells. Conversely, luminal genes (such as KRT19, MUC1, ELF5) were highly upregulated in LP cells compared to B+ cells. Gene expression levels of MME (CD10), TP63, SNAl2, GATA3, ELF5 and KRT8 were confirmed by qPCR for three donors, strongly suggesting that B+ cells are basal/myoepithelial (FIG. 5C). Surprisingly, the expression of both basal and luminal cell-fate determinants was low in B– cells compared to B+ and LP cells (FIG. 5B). In particular, the comparatively lower expression of both basal (KRT14) and luminal cytokeratins (KRT8, 18, 19) by the B– population, together with the absence of structure formation in floating collagen gels, called into question the epithelial identity of these cells (FIG. 5B,C). Indeed, the 20 most highly upregulated transcripts (FDR<10%) in the B– versus B+ population included IGK (encoding immunoglobulin chains), LYVE1 and CDH5 (encoding VE-cadherin), indicative of B-cells, T-cells, as well as lymph- and vascular-endothelial cells (FIG. 5D). In support of these data, GO-term analysis revealed groups of genes associated with circulatory system development, cytokine receptor binding, antigen binding, VEGF and angiogenesis to be significantly over-represented within the B– compared to the B+ gene expression profile (FIG. 5E). These results suggested that the CD49f$^{hi}$/EpCAM$^-$ population, commonly referred to as basal, contains stromal cells, including hematopoietic and endothelial cells. Importantly, a systematic analysis of cell fate markers in the human MG by immunohistochemistry recently revealed that all cells at basal positions express CD10, supporting the conclusion that the B– population contains non-basal cells (Santagata et al., 2014). CD31 and CD45, as employed in the study, are commonly used markers to exclude endothelial and hematopoietic cells from sorted cell populations. However, the data suggest that these markers do not allow for complete exclusion of such cells. Indeed, it has been shown that certain types of endothelial cells, such as in spleen and kidney capillaries, are negative for CD31 (Pusztaszeri et al., 2006). The gene expression profile of the B– population also suggested the presence of B– cells or T-cells: Indeed, transitional B-cells as well as plasmablasts and plasma cells are known to downregulate CD45 and might therefore be included in the B– population (Zikherman et al., 2012).

Thus, using CD10 as a cell surface marker within the CD49f$^{hi}$/EpCAM$^-$ population does not merely enrich regenerative cells within the basal cell population, but rather yields a purified basal population. To analyze whether CD10 can replace CD49f in the FACS protocol, its expression was determined in the different subpopulations derived by staining with CD49f and EpCAM. Importantly, CD10 was not only expressed within the CD49f$^{hi}$/EpCAM$^-$ population. Among 10 donors, on average 1% of LM (CD49f$^-$/EpCAM$^+$), 10% of LP (CD49f$^+$/EpCAM$^+$) and 47% of stromal cells (CD49f$^-$/EpCAM$^-$) were found to express CD10 (FIG. 5F,G). Taken together, the results indicate that stromal cells have the following cell-surface marker profiles: CD10$^{-/+}$/CD49f$^{-/+}$/EpCAM$^{-/+}$. Therefore, only sorting of CD10$^+$/CD49f$^+$/EpCAM$^-$ cells allows for exclusion of different stromal populations in order to purify basal cells.

Example 8: Branched Structures Derived From the B+ Population Display Markers of the Luminal Lineage Since B+ cells were able to form structures in floating collagen gels that resemble TDLU in situ, it was hypothesized that they might give rise to cells of the luminal lineage, analogous to bipotential progenitors or MaSC. By contrast, LP cells, which mainly formed spheres in floating collagen gels, were expected to be mostly restricted to a luminal cell fate. Therefore, B+ and LP populations were sorted of freshly isolated HMEC, the cells were plated into floating collagen gels, and they were cultured for a period of 20 days, to allow for differentiation. Next, immunohistochemistry was performed on serial sections for nuclear expression of the transcription factors p63 and GATA-3, critical determinants of basal and luminal cell fate, respectively (Asselin-Labat et al., 2007; Kouros-Mehr et al., 2006). It could be observed that all TDLU-like structures derived from B+ cells contained p63-positive cells in basal positions and were also GATA-3-positive in luminal positions, suggesting that B+ cells gave rise to cells expressing markers of the luminal lineage (FIG. 6A). However, expression of the luminal marker cytokeratin (CK)18 could not be detected in structures derived from B+ cells, suggesting that CK18 might be induced later in the differentiation process. As expected, spheres derived from LP cells were p63-negative, but GATA-3- and CK18-positive (FIG. 6A). In conclusion, the data suggest that B+ cells exhibit bipotent features in floating collagen gels by giving rise to GATA-3 positive cells. The observation that LP cells did not give rise to any p63-positive cells suggests that they are largely lineage-restricted.

Example 9: TDLU-Like Structures Derived From B+ Cells Recapitulate Functional Aspects of the Mammary Gland A major function of the basal/myoepithelial cells in the MG is contraction of the ducts during lactation, supporting milk ejection. Indeed, it could be observed that gels containing TDLU-like structures began to contract after approximately 12 days of culture, thus shrinking in diameter (FIG. 6B). To determine which cells exerted contractility, sorted B+ and LP cells were cultured in floating collagen gels for 12 days to allow for generation of TDLU-like structures and spheres, respectively. Gels were photographed from this time point on every 24 hours for 2 more days. At this point, gels containing B+ cells were contracted to about half of their initial size (FIG. 6C,D). These observations suggest that B+ cells, which give rise to TDLU-like structures, exert contractile activity in floating collagen gels, whereas LP cells, which generate spheres, do not.

The morphogen TGF-β1 promotes contractility (Scharenberg et al., 2014). Indeed, one-time treatment with 2.0 ng/ml recombinant TGF-β1 increased contraction of the gels containing B+ derived TDLU-like structures by approximately 2-fold (FIG. 6C,D). By contrast, TGF-β1 did not have an effect on the size of gels containing LP-derived spheres from donor M10, which is in accordance with the non-contractile function of these cells in situ. Interestingly, TGF-β1 did induce a slight contraction of collagen gels containing M3 luminal cells. However, this contraction was much less pronounced than the contraction of gels containing B+ cells. Importantly, determining the average number of cells per gel revealed that contraction was not correlated with differences in proliferation (FIG. 6E). To confirm the increase in contraction after TGF-β1-treatment at a cellular level, detection of F-actin was performed using phalloidin, and the average cell size was determined. In accordance with the decreased gel size, single cells were significantly smaller in diameter in TGF-β1-treated structures as compared to controls (FIG. 6F).

In conclusion, contractility, an essential function of myoepithelial cells in the adult MG, is recapitulated in floating epithelial gels and can be further stimulated by TGF-β1-treatment. Indeed, it was recently shown that murine MaSC are myoepithelial and thus, contractile (Prater et al., 2014). Therefore, determining contractility in floating collagen gels might serve as a functional assay for the identification and characterization of human MaSC.

Example 10: Matrix Compliance in Floating Collagen Gels is Necessary for Alveologenesis and Luminal Differentiation of TDLU-Like Structures To test whether contraction of gels is required for formation of TDLU-like structures, HMEC were either cultured in floating collagen gels or in gels that remained attached to the bottom and walls of the polystyrene culture dish, thereby preventing gel-contraction. Additionally, HMEC were plated into attached collagen gels that were detached to float once branched structures had formed (FIG. 7A). Substantial differences in morphology were displayed in floating versus attached gels: while cells in floating gels developed alveoli at the tips of branched structures, cells in attached gels formed thin and elongated ducts with a significantly increased number of side branches and complete lack of alveologenesis (FIG. 7B,C). Remarkably, formation of alveoli could be induced within 24 hours in attached gels that were detached to float (FIG. 7B). Together, these results indicated that a rigid collagen matrix that cannot be contracted by B+ cells promotes elongation and side branching whereas a compliant matrix in floating gels promotes alveologenesis.

To further investigate whether switching from a rigid to a compliant matrix environment promoted differentiation at the cellular level, confocal immunofluorescence was performed. In floating/compliant collagen gels, cells of the outer layers adjacent to the collagen matrix expressed the basal marker p63. In contrast, cells in the inner layer were p63-negative and expressed the transcription factor GATA-3 and the tight-junction protein ZO-1 at luminal positions (FIGS. 7D, 11A), consistent with the earlier observations (FIG. 6A) and similar to lineage marker expression in situ. Furthermore, integrin-α6 (CD49f) was exclusively localized at the basal position and co-localized with its ligand laminin, indicating deposition of basement membrane components by the basal cell layer. By contrast, branched structures in attached/rigid gels did not form round buds and showed no polarized expression of p63, integrin-α6, and low to undetectable levels of laminin (FIG. 7B,D). Furthermore, ZO-1 was not detectable in branched structures within attached collagen gels, whereas GATA-3 staining was only observed in rare cells that were localized at both basal and luminal positions (FIGS. 7D, 11A). These observations were further supported by the finding that mRNA levels of ELF5 and TJP1/ZO-1 were not detectable or lower in B+ cell-derived branched structures grown in attached compared to floating collagen gels (FIG. 11B). However, expression of GATA3 mRNA was detected in all conditions (data not shown). As expected by the non-contractile function of luminal cells, attachment of the gels did not have any detectable effect on the morphology, as well as on the expression of ELF5 and TJP1/ZO-1 in LP-derived spheres (FIG. 11B,C). Taken together, these results indicated that culture within a floating/compliant collagen matrix promotes alveologenesis and luminal differentiation of basal HMEC.

To test whether contractility of basal cells was required for alveologenesis, freshly isolated HMEC were again plated into attached collagen gels. Once branched structures had formed, gels were detached and simultaneously treated with either the myosin-II inhibitor Blebbistatin (Prater et al., 2014) or the ROCK-inhibitor Y-27632 to prevent cellular contraction (FIG. 11D,E). While structures in the control condition acquired an alveolar morphology after detachment, this was prevented by treatment with either of the compounds (FIG. 11F). Together, these results indicate that the contractile function of basal cells is crucial for alveologenesis and differentiation.

Tables

TABLE 1

Reduction mammoplasty donors

| Donor | Age (years) | Parity |
|---|---|---|
| M1 | 44 | 1 |
| M2 | 68 | 1 |
| M3 | 71 | 2 |
| M4 | 68 | 2 |
| M5 | 48 | 2 |
| M6 | 69 | 1 |
| M7 | 35 | 2 |
| M8 | 53 | 2 |
| M9 | 17 | 0 |
| M10 | 42 | 1 |
| M12 | 54 | 0 |

TABLE 2

Primers used for qPCR

| Target | Sequence (Fw, Rv) |
|---|---|
| CDH1 | TGCCCAGAAAATGAAAAAGG (SEQ ID No: 1), GTGTATGTGGCAATGCGTTC (SEQ ID No: 2) |
| ELF5 | TAGGGAACAAGGAATTTTTCGGG (SEQ ID No: 3), GTACACTAACCTTCGGTCAACC (SEQ ID No: 4) |
| FN1 | CAGTGGGAGACCTCGAGAAG (SEQ ID No: 5), TCCCTCGGAACATCAGAAAC (SEQ ID No: 6) |
| GATA3 | GCCCCTCATTAAGCCCAAG (SEQ ID No: 7), TTGTGGTGGTCTGACAGTTCG (SEQ ID No: 8) |
| KRT8 | TCCTCAGGCAGCTATATGAAGAG (SEQ ID No: 9), GGTTGGCAATATCCTCGTACTGT (SEQ ID No: 10) |
| RPL32 | CAGGGTTCGTAGAAGATTCAAGGG (SEQ ID No: 11), CTTGGAGGAAACATTGTGAGCGATC (SEQ ID No: 12) |
| MME | TGGATCTTGTAAGCAGCCTCA (SEQ ID No: 13), GCACAACGTCTCCAAGTTGC (SEQ ID No: 14) |
| CDH2 | ACAGTGGCCACCTACAAAGG (SEQ ID No: 15), CCGAGATGGGGTTGATAATG (SEQ ID No: 16) |
| OVOL2 | ACAGGCATTCGTCCCTACAAA (SEQ ID No: 17), CGCTGCTTATAGGCATACTGC (SEQ ID No: 18) |
| TP63 | AGAGAGAGGGACTTGAGTTCT (SEQ ID No: 19), TGGTCGATGCTGTTCAGGAGC (SEQ ID No: 20) |
| SNAI2 | GGGGAGAAGCCTTTTTCTTG (SEQ ID No: 21), TCCTCATGTTTGTGCAGGAG (SEQ ID No: 22) |
| VIM | GAGAACTTTGCCGTTGAAGC (SEQ ID No: 23), GCTTCCTGTAGGTGGCAATC (SEQ ID No: 24) |
| ZEB1 | GCACAAGAAGAGCCACAAGTAG (SEQ ID No: 25), GCAAGACAAGTTCAAGGGTTC (SEQ ID No: 26) |
| TJP1 | CTTACCACACTGTGCGTCCAT (SEQ ID No: 27), AGGAGTCGGATGATTTTAGAGCA (SEQ ID No: 28) |

TABLE 3

Primary antibodies for immunohistochemistry and immunofluorescence

| Epitope [Clone] | Conjugation | Host | Supplier |
|---|---|---|---|
| Immunohistochemistry | | | |
| GATA3 [L50-823] | — | mouse | Biocare Medical (CM405) |
| CK18 [Ks18.04] | — | mouse | Progen (61028) |
| p63 [BC4A4] | — | mouse | Biocare Medical (PM163AAK) |
| Immunofluorescence | | | |
| E-cadherin [24E10] | Alexa 488 | rabbit | NEB, Whitby, Canada |

TABLE 3-continued

Primary antibodies for immunohistochemistry and immunofluorescence

| Epitope [Clone] | Conjugation | Host | Supplier |
|---|---|---|---|
| E-cadherin [EP700Y] | — | rabbit | Biozol, Eching |
| GATA-3 [L50-823] | — | mouse | Biocare Medical (CM405) |
| integrin-α6 [GOH3] | — | rat | Santa Cruz, Dallas, USA |
| laminin | — | rabbit | Sigma, Steinheim |
| p63 [BC4A4] | — | mouse | Abcam, Cambridge, UK |
| p63 [H-137] | — | rabbit | Santa Cruz, Dallas, USA |
| Phalloidin | Atto 647N | — | Sigma, Steinheim |
| vimentin [D21H3] XP | — | rabbit | Biozol, Eching |
| vimentin [V9] | — | mouse | Abcam, Cambridge, UK |
| ZO-1 | Alexa 594 | mouse | Invitrogen, Karlsruhe |
| ZO-1 [1A12] | — | mouse | Life Technologies |

TABLE 4

Secondary antibodies

| Host | Epitope | Conjugation | Supplier |
|---|---|---|---|
| Goat | Mouse IgG | Alexa 594 | Life Technologies, Darmstadt |
| Goat | Rabbit IgG | Alexa 488 | Life Technologies, Darmstadt |
| Donkey | Mouse IgG | Alexa 488 | Life Technologies, Darmstadt |
| Donkey | Rabbit IgG | Alexa 546 | Life Technologies, Darmstadt |
| Donkey | Rabbit IgG | Alexa 488 | Life Technologies, Darmstadt |
| Donkey | Rabbit IgG | Alexa 594 | Life Technologies, Darmstadt |
| Donkey | Rat IgG | Cy3 | Dianova, Hamburg |

TABLE 5

Antibodies used for flow cytometry and fluorescence activated cell sorting

| Epitope [Clone] | Conjugation | Host | Supplier |
|---|---|---|---|
| 7-AAD | — | — | BD, Heidelberg |
| CD10 [HIC10a] | APC | mouse | Biozol, Eching |
| CD31 [WM59] | PB | mouse | Biozol, Eching |
| CD326/EpCAM [VU-1D9] | FITC | mouse | Biozol, Eching |
| CD45 (HI30) | V450 | mouse | BD, Heidelberg |
| CD49f [GoH3] | PE | rat | BD, Heidelberg |

REFERENCES

Alitalo, A. and Detmar, M. (2012). Interaction of tumor cells and lymphatic vessels in cancer progression. *Oncogene* 31, 4499-4508.

Anderson, E., Clarke, R. B. and Howell, A. (1998). Estrogen responsiveness and control of normal human breast proliferation. *J Mammary Gland Biol Neoplasia* 3, 23-35.

Asselin-Labat, M.-L., Sutherland, K. D., Barker, H., Thomas, R., Shackleton, M., Forrest, N. C., Hartley, L., Robb, L., Grosveld, F. G., van der Wees, J., et al. (2007). Gata-3 is an essential regulator of mammary-gland morphogenesis and luminal-cell differentiation. *Nat. Cell Biol.* 9, 201-209.

Bachelard-Cascales, E., Chapellier, M., Delay, E., Pochon, G., Voeltzel, T., Puisieux, A., Caron de Fromentel, C. and Maguer-Satta, V. (2010). The CD10 enzyme is a key player to identify and regulate human mammary stem cells. *Stem Cells* 28, 1081-1088.

Bainer, R. and Weaver, V. (2013). Cell biology. Strength under tension. *Science* 341, 965-966.

Benton, G., Arnaoutova, I., George, J., Kleinman, H. K. and Koblinski, J. (2014). Matrigel: From discovery and ECM mimicry to assays and models for cancer research. *Adv. Drug Deliv. Rev.* 79-80C, 3-18.

Betterman, K. L., Paquet-Fifield, S., Asselin-Labat, M.-L., Visvader, J. E., Butler, L. M., Stacker, S. A., Achen, M. G. and Harvey, N. L. (2012). Remodeling of the lymphatic vasculature during mouse mammary gland morphogenesis is mediated via epithelial-derived lymphangiogenic stimuli. *Am. J. Pathol.* 181, 2225-2238.

Brisken, C. and Duss, S. (2007). Stem cells and the stem cell niche in the breast: an integrated hormonal and developmental perspective. *Stem Cell Rev and Rep* 3, 147-156.

Brisken, C. and O'Malley, B. (2010). Hormone action in the mammary gland. *Cold Spring Harb Perspect Biol* 2, a003178.

Celià-Terrassa, T., Meca-Cortés, O, Mateo, F., de Paz, A. M., Rubio, N., Arnal-Estapé, A., Ell, B. J., Bermudo, R., Diaz, A., Guerra-Rebollo, M., et al. (2012). Epithelial-mesenchymal transition can suppress major attributes of human epithelial tumor-initiating cells. *J. Clin. Invest.* 122, 1849-1868.

Chaudhuri, O., Koshy, S. T., Branco da Cunha, C., Shin, J.-W., Verbeke, C. S., Allison, K. H. and Mooney, D. J. (2014). Extracellular matrix stiffness and composition jointly regulate the induction of malignant phenotypes in mammary epithelium. *Nature Materials* 13, 970-978.

Cheung, K. J., Gabrielson E., Werb Z. and Ewald A. J. (2013). Collective invasion in breast cancer requires a conserved basal epithelial program. *Cell* 155, 1639-1651.

Dontu, G., Abdallah, W. M., Foley, J. M., Jackson, K. W., Clarke, M. F., Kawamura, M. J. and Wicha, M. S. (2003). In vitro propagation and transcriptional profiling of human mammary stem/progenitor cells. *Genes Dev.* 17, 1253-1270.

Ehmann, U. K., Peterson, W. D. and Misfeldt, D. S. (1984). To grow mouse mammary epithelial cells in culture. *J. Cell Biol.* 98, 1026-1032.

Eirew, P., Stingl, J., Raouf, A., Turashvili, G., Aparicio, S., Emerman, J. T. and Eaves, C. J. (2008). A method for quantifying normal human mammary epithelial stem cells with in vivo regenerative ability. *Nat. Med.* 14, 1384-1389.

Fradkin, J. E., Cook, G. H., Kilhoffer, M. C. and Wolff, J. (1982). Forskolin stimulation of thyroid adenylate cyclase and cyclic 3",5"-adenosine monophosphate accumulation. *Endocrinology* 111, 849-856.

Fridriksdottir, A. J. R., Petersen, O. W. and Rnnov-Jessen, L. (2011). Mammary gland stem cells: current status and future challenges. *Int. J. Dev. Biol.* 55, 719-729.

Gudjonsson, T., Villadsen, R., Nielsen, H. L., Rønnov-Jessen, L., Bissell, M. J. and Petersen, O. W. (2002). Isolation, immortalization, and characterization of a human breast epithelial cell line with stem cell properties. *Genes Dev.* 16, 693-706.

Guo, W., Keckesova, Z., Donaher, J. L., Shibue, T., Tischler, V., Reinhardt, F., Itzkovitz, S., Noske, A., Zürrer-Härdi, U., Bell, G., et al. (2012). Slug and Sox9 Cooperatively Determine the Mammary Stem Cell State. *Cell* 148, 1015-1028.

Hu, Y. and Smyth, G. K. (2009). ELDA: extreme limiting dilution analysis for comparing depleted and enriched populations in stem cell and other assays. *J. Immunol. Methods* 347, 70-78.

Keller, P. J., Lin, A. F., Arendt, L. M., Klebba, I., Jones, A. D., Rudnick, J. A., DiMeo, T. A., Gilmore, H., Jefferson, D. M., Graham, R. A., et al. (2010). Mapping the cellular and molecular heterogeneity of normal and malignant breast tissues and cultured cell lines. *Breast Cancer Res.* 12, R87.

Kouros-Mehr, H., Slorach, E. M., Sternlicht, M. D. and Werb, Z. (2006). GATA-3 maintains the differentiation of the luminal cell fate in the mammary gland. *Cell* 127, 1041-1055.

Levental, K. R., Yu, H., Kass, L., Lakins, J. N., Egeblad, M., Erler, J. T., Fong, S. F. T., Csiszar, K., Giaccia, A., Weninger, W., et al. (2009). Matrix crosslinking forces tumor progression by enhancing integrin signaling. *Cell* 139, 891-906.

Lim, E., Vaillant, F., Di Wu, Forrest, N. C., Pal, B., Hart, A. H., Asselin-Labat, M.-L., Gyorki, D. E., Ward, T., Partanen, A., et al. (2009a). Aberrant luminal progenitors as the candidate target population for basal tumor development in BRCA1 mutation carriers. *Nat. Med.* 1-9.

Lim, E., Vaillant, F., Wu, D., Forrest, N. C., Pal, B., Hart, A. H., Asselin-Labat, M.-L., Gyorki, D. E., Ward, T., Partanen, A., et al. (2009b). Aberrant luminal progenitors as the candidate target population for basal tumor development in BRCA1 mutation carriers. *Nat. Med.* 15, 907-913.

Lu, P., Sternlicht, M. D. and Werb, Z. (2006). Comparative mechanisms of branching morphogenesis in diverse systems. *J Mammary Gland Biol Neoplasia* 11, 213-228.

Magee, J. A., Piskounova, E. and Morrison, S. J. (2012). Cancer Stem Cells: Impact, Heterogeneity, and Uncertainty. Cancer *Cell* 21, 283-296.

Maguer-Satta, V., Chapellier, M., Delay, E. and Bachelard-Cascales, E. (2011). CD10: a tool to crack the role of stem cells in breast cancer. *Proc. Natl. Acad. Sci. U.S.A.* 108, E1264—author reply E1265.

Mailleux, A. A., Overholtzer, M. and Brugge, J. S. (2008). Lumen formation during mammary epithelial morphogenesis: insights from in vitro and in vivo models. cc 7, 57-62.

Makarem, M., Kannan, N., Nguyen, L. V., Knapp, D. J. H. F., Balani, S., Prater, M. D., Stingl, J., Raouf, A., Nemirovsky, O., Eirew, P., et al. (2013). Developmental changes in the in vitro activated regenerative activity of primitive mammary epithelial cells. *Plos Biol* 11, e1001630.

Mani, S. A., Guo, W., Liao, M.-J., Eaton, E. N., Ayyanan, A., Zhou, A. Y., Brooks, M., Reinhard, F., Zhang, C. C., Shipitsin, M., et al. (2008). The epithelial-mesenchymal transition generates cells with properties of stem cells. *Cell* 133, 704-715.

Morel, A.-P., Lièvre, M., Thomas, C., Hinkal, G., Ansieau, S. and Puisieux, A. (2008). Generation of breast cancer stem cells through epithelial-mesenchymal transition. *PLoS ONE* 3, e2888.

Muschler, J. and Streuli, C. H. (2010). Cell-matrix interactions in mammary gland development and breast cancer. *Cold Spring Harb Perspect Biol* 2, a003202-a003202.

Nedvetsky, P. I., Kwon, S.-H., Debnath, J. and Mostov, K. E. (2012). Cyclic AMP regulates formation of mammary epithelial acini in vitro. *Mol. Biol. Cell* 23, 2973-2981.

Nigam, S. K. (2013). Concise review: can the intrinsic power of branching morphogenesis be used for engineering epithelial tissues and organs? *Stem Cells Transl Med* 2, 993-1000.

Ocaña, O. H., Córcoles, R., Fabra, A., Moreno-Bueno, G., Acloque, H., Vega, S., Barrallo-Gimeno, A., Cano, A. and Nieto, M. A. (2012). Metastatic Colonization Requires the Repression of the Epithelial-Mesenchymal Transition Inducer Prrx1. *Cancer Cell* 1-16.

Parmar, H. and Cunha, G. R. (2004). Epithelial-stromal interactions in the mouse and human mammary gland in vivo. *Endocrine Related Cancer* 11, 437-458.

Paszek, M. and Weaver, V. (2010). Biophysics. Enforcing order on signaling. *Science* 327, 1335-1336.

Paszek, M. J., Zahir, N., Johnson, K. R., Lakins, J. N., Rozenberg, G. I., Gefen, A., Reinhart-King, C. A., Margulies, S. S., Dembo, M., Boettiger, D., et al. (2005). Tensional homeostasis and the malignant phenotype. *Cancer Cell* 8, 241-254.

Prater, M. D., Petit, V., Alasdair Russell, I., Giraddi, R. R., Shehata, M., Menon, S., Schulte, R., Kalajzic, I., Metzger, D., Faraldo, M. M., et al. (2014). Mammary stem cells have myoepithelial cell properties. *Nat. Cell Biol.*

Proia, D. A. and Kuperwasser, C. (2006). Reconstruction of human mammary tissues in a mouse model. *Nat Protoc* 1, 206-214.

Provenzano, P. P. and Keely, P. J. (2009). The role of focal adhesion kinase in tumor initiation and progression. *Cell Adh Migr* 3, 347-350.

Pusztaszeri, M. P., Seelentag, W. and Bosman, F. T. (2006). Immunohistochemical expression of endothelial markers CD31, CD34, von Willebrand factor, and Fli-1 in normal human tissues. *J. Histochem. Cytochem.* 54, 385-395.

Rainer, J., Sanchez-Cabo, F., Stocker, G., Sturn, A. and Trajanoski, Z. (2006). CARMAweb: comprehensive R- and bioconductor-based web service for microarray data analysis. *Nucleic Acids Res.* 34, W498-503.

Rios, A. C., Fu, N. Y., Lindeman, G. J. and Visvader, J. E. (2014). In situ identification of bipotent stem cells in the mammary gland. *Nature* 1-19.

Santagata, S., Thakkar, A., Ergonul, A., Wang, B., Woo, T., Hu, R., Harrell, J. C., McNamara, G., Schwede, M., Culhane, A. C., et al. (2014). Taxonomy of breast cancer based on normal cell phenotype predicts outcome. *J. Clin. Invest.* 124, 859-870.

Scharenberg, M. A., Pippenger, B. E., Sack, R., Zingg, D., Ferralli, J., Schenk, S., Martin, I. and Chiquet-Ehrismann, R. (2014). TGF-β-induced differentiation into myofibroblasts involves specific regulation of two MKL1 isoforms. *Journal of Cell Science* 127, 1079-1091.

Schedin, P. and Keely, P. J. (2011). Mammary gland ECM remodeling, stiffness, and mechanosignaling in normal development and tumor progression. *Cold Spring Harb Perspect Biol* 3, a003228-a003228.

Scheel, C., Eaton, E. N., Li, S. H.-J., Chaffer, C. L., Reinhardt, F., Kah, K.-J., Bell, G., Guo, W., Rubin, J., Richardson, A. L., et al. (2011). Paracrine and autocrine signals induce and maintain mesenchymal and stem cell states in the breast. *Cell* 145, 926-940.

Schmittgen, T. D. and Livak, K. J. (2008). Analyzing real-time PCR data by the comparative C(T) method. *Nat Protoc* 3, 1101-1108.

Shackleton, M., Vaillant, F., Simpson, K. J., Stingl, J., Smyth, G. K., Asselin-Labat, M.-L., Wu, L., Lindeman, G. J. and Visvader, J. E. (2006). Generation of a functional mammary gland from a single stem cell. *Nature* 439, 84-88.

Shehata, M., Teschendorff, A., Sharp, G., Novcic, N., Russell, I. A., Avril, S., Prater, M., Eirew, P., Caldas, C., Watson, C. J., et al. (2012). Phenotypic and functional characterisation of the luminal cell hierarchy of the mammary gland. *Breast Cancer Res.* 14, R134.

Stampfer, M. R. (1982). Cholera toxin stimulation of human mammary epithelial cells in culture. *In Vitro* 18, 531-537.

Sternlicht, M. D. (2006). Key stages in mammary gland development: the cues that regulate ductal branching morphogenesis. *Breast Cancer Res.* 8, 201.

Stingl, J., Eirew, P., Ricketson, I., Shackleton, M., Valliant, F., Choi, D., Li, H. I. and Eaves, C. J. (2006). Purification and unique properties of mammary epithelial stem cells. *Nature* 439, 993-997.

Stingl, J., Emerman, J. T. and Eaves, C. J. (2005). Enzymatic dissociation and culture of normal human mammary tissue to detect progenitor activity. *Methods Mol. Biol.* 290, 249-263.

Tanos, T., Rojo, L., Echeverria, P. and Brisken, C. (2012). ER and PR signaling nodes during mammary gland development. *Breast Cancer Res.* 14, 210.

Tanos, T., Sflomos, G., Echeverria, P. C., Ayyanan, A., Gutierrez, M., Delaloye, J.-F., Raffoul, W., Fiche, M., Dougall, W., Schneider, P., et al. (2013). Progesterone/RANKL is a major regulatory axis in the human breast. *Sci Transl Med* 5, 182ra55-182ra55.

Tran, H. D., Luitel, K., Kim, M., Zhang, K., Longmore, G. D. and Tran, D. D. (2014). Transient SNAIL1 Expression is Necessary for Metastatic Competence in Breast Cancer. *Cancer Res.* 74, 6330-6340.

Tsai, J. H., Donaher, J. L., Murphy, D. A., Chau, S. and Yang, J. (2012). Spatiotemporal regulation of epithelial-mesenchymal transition is essential for squamous cell carcinoma metastasis. *Cancer Cell* 22, 725-736.

van Amerongen, R., Bowman, A. N. and Nusse, R. (2012). Developmental Stage and Time Dictate the Fate of Wnt/β-Catenin-Responsive Stem Cells in the Mammary Gland. *Stem Cell* 11, 387-400.

Van Keymeulen, A., Rocha, A. S., Ousset, M., Beck, B., Bouvencourt, G., Rock, J., Sharma, N., Dekoninck, S. and Blanpain, C. (2012). Distinct stem cells contribute to mammary gland development and maintenance. *Nature* 479, 189-193.

Visvader, J. E. and Stingl, J. (2014). Mammary stem cells and the differentiation hierarchy: current status and perspectives. *Genes Dev.* 28, 1143-1158.

Wang, D., Cal, C., Dong, X., Yu, Q. C., Zhang, X.-O., Yang, L. and Zeng, Y. A. (2014). Identification of multipotent mammary stem cells by protein C receptor expression. *Nature*.

Watanabe, K., Villarreal-Ponce, A., Sun, P., Salmans, M. L., Fallahi, M., Andersen, B. and Dai, X. (2014). Mammary Morphogenesis and Regeneration Require the Inhibition of EMT at Terminal End Buds by Ovol2 Transcriptional Repressor. *Dev. Cell* 29, 59-74.

Wozniak, M. A. and Keely, P. J. (2005). Use of three-dimensional collagen gels to study mechanotransduction in T47D breast epithelial cells. *Biol Proced Online* 7, 144-161.

Wozniak, M. A., Desai, R., Solski, P. A., Der, C. J. and Keely, P. J. (2003). ROCK-generated contractility regulates breast epithelial cell differentiation in response to the physical properties of a three-dimensional collagen matrix. *J. Cell Biol.* 163, 583-595.

Zikherman, J., Doan, K., Parameswaran, R., Raschke, W. and Weiss, A. (2012). Quantitative differences in CD45 expression unmask functions for CD45 in B-cell development, tolerance, and survival. *Proc. Natl. Acad. Sci. U.S.A.* 109, E3-12.

---

The invention claimed is:

1. A method of generating a breast stem cell comprising:
   (i) culturing dissociated cells from mammary epithelial tissue in a culture medium comprising a floating collagen gel for at least 7 days, said culture medium comprising a compound which elevates cAMP levels, wherein said culturing forms a multicellular organoid unit;
   (ii) obtaining a single breast stem cell from said multicellular organoid unit, wherein the single breast stem cell differentiates to a multicellular organoid unit that morphologically and/or functionally resembles a terminal ductal-lobular unit.

2. The method of claim 1, wherein (a) the method further comprises determining whether said multicellular organoid unit of (i) and/or (ii) is formed by determining whether ductal structures and multiple branch-points and/or alveoli are comprised by said multicellular organoid unit of (i) and/or (ii) or (b) the method further comprises determining whether said multicellular organoid unit of (i) and/or (ii) is capable of contracting the floating collagen gel, optionally wherein contraction of the floating collagen gel is indicative of alveologenesis.

3. The method of claim 1, (a) wherein said culture medium comprises a Rho-kinase (ROCK) inhibitor, said ROCK inhibitor being either unspecific or specific for either ROCK1 and/or ROCK2, (b) further comprising sorting the cells from mammary epithelial tissue to enrich for breast stem cells comprising the cell surface marker combination $CD31^-$, $CD45^-$, $EpCAM^-$, $CD49f^+$ and $CD10^+$ prior to culturing said cells from mammary epithelial tissue in a collagen gel, or (c) or wherein the mammary epithelial tissue is healthy or diseased tissue, optionally wherein the diseased mammary epithelial tissue comprises germ-line or somatic mutations, or any combination of (a)-(c).

4. The method of claim 3, wherein (a) the mammary epithelial tissue is dissociated mechanically and enzymatically, (b) the ROCK inhibitor is Y-27632 or Thiazovivin and wherein the compound which elevates cAMP levels is an adenylylcyclase agonist that is optionally Forskolin, or (c) the ROCK inhibitor is removed from the culture medium after about 5 days, or any combination of (a)-(c).

5. The method of claim 1, wherein (a) the multicellular organoid unit of (i) and/or (ii) is responsive to hormones and/or growth factors, or (b) said dissociated cells are cultured in 2D-culture or other methods of culture prior to transferring to the culture medium comprising the floating collagen gel, or both (a) and (b).

6. The method of claim 1, wherein said floating collagen gel is a collagen-1 gel.

\* \* \* \* \*

SEQUENCE LISTING

```
<160> NUMBER OF SEQ ID NOS: 28

<210> SEQ ID NO 1
<211> LENGTH: 20
<212> TYPE: DNA
<213> ORGANISM: artificial
<220> FEATURE:
<223> OTHER INFORMATION: CDH1 primer

<400> SEQUENCE: 1
tgcccagaaa atgaaaaagg                                                   20

<210> SEQ ID NO 2
<211> LENGTH: 20
<212> TYPE: DNA
<213> ORGANISM: artificial
<220> FEATURE:
<223> OTHER INFORMATION: CDH1 primer

<400> SEQUENCE: 2
gtgtatgtgg caatgcgttc                                                   20

<210> SEQ ID NO 3
<211> LENGTH: 23
<212> TYPE: DNA
<213> ORGANISM: artificial
<220> FEATURE:
<223> OTHER INFORMATION: ELF5 primer

<400> SEQUENCE: 3
tagggaacaa ggaatttttc ggg                                               23
```

```
<210> SEQ ID NO 4
<211> LENGTH: 22
<212> TYPE: DNA
<213> ORGANISM: artificial
<220> FEATURE:
<223> OTHER INFORMATION: ELF5 primer

<400> SEQUENCE: 4
gtacactaac cttcggtcaa cc                                          22

<210> SEQ ID NO 5
<211> LENGTH: 20
<212> TYPE: DNA
<213> ORGANISM: artificial
<220> FEATURE:
<223> OTHER INFORMATION: FN1 primer

<400> SEQUENCE: 5
cagtgggaga cctcgagaag                                             20

<210> SEQ ID NO 6
<211> LENGTH: 20
<212> TYPE: DNA
<213> ORGANISM: artificial
<220> FEATURE:
<223> OTHER INFORMATION: FN1 primer

<400> SEQUENCE: 6
tccctcggaa catcagaaac                                             20

<210> SEQ ID NO 7
<211> LENGTH: 19
<212> TYPE: DNA
<213> ORGANISM: artificial
<220> FEATURE:
<223> OTHER INFORMATION: GATA3 primer

<400> SEQUENCE: 7 gccccctcatt aagcccaag                                             19

<210> SEQ ID NO 8
<211> LENGTH: 21
<212> TYPE: DNA
<213> ORGANISM: artificial
<220> FEATURE:
<223> OTHER INFORMATION: GATA3 primer

<400> SEQUENCE: 8
ttgtggtggt ctgacagttc g                                           21

<210> SEQ ID NO 9
<211> LENGTH: 23
<212> TYPE: DNA
<213> ORGANISM: artificial
<220> FEATURE:
<223> OTHER INFORMATION: KRT8 primer

<400> SEQUENCE: 9
tcctcaggca gctatatgaa gag                                         23

<210> SEQ ID NO 10
<211> LENGTH: 23
<212> TYPE: DNA
<213> ORGANISM: artificial
<220> FEATURE:
<223> OTHER INFORMATION: KRT8 primer
```

<400> SEQUENCE: 10
ggttggcaat atcctcgtac tgt                                   23

<210> SEQ ID NO 11
<211> LENGTH: 24
<212> TYPE: DNA
<213> ORGANISM: artificial
<220> FEATURE:
<223> OTHER INFORMATION: RPL32 primer

<400> SEQUENCE: 11
cagggttcgt agaagattca aggg                                  24

<210> SEQ ID NO 12
<211> LENGTH: 25
<212> TYPE: DNA
<213> ORGANISM: artificial
<220> FEATURE:
<223> OTHER INFORMATION: RPL32 primer

<400> SEQUENCE: 12
cttggaggaa acattgtgag cgatc                                 25

<210> SEQ ID NO 13
<211> LENGTH: 21
<212> TYPE: DNA
<213> ORGANISM: artificial
<220> FEATURE:
<223> OTHER INFORMATION: MME primer

<400> SEQUENCE: 13
tggatcttgt aagcagcctc a                                     21

<210> SEQ ID NO 14
<211> LENGTH: 20
<212> TYPE: DNA
<213> ORGANISM: artificial
<220> FEATURE:
<223> OTHER INFORMATION: MME primer

<400> SEQUENCE: 14
gcacaacgtc tccaagttgc                                       20

<210> SEQ ID NO 15
<211> LENGTH: 20
<212> TYPE: DNA
<213> ORGANISM: artificial
<220> FEATURE:
<223> OTHER INFORMATION: CDH2 primer

<400> SEQUENCE: 15
acagtggcca cctacaaagg                                       20

<210> SEQ ID NO 16
<211> LENGTH: 20
<212> TYPE: DNA
<213> ORGANISM: artificial
<220> FEATURE:
<223> OTHER INFORMATION: CDH2 primer

<400> SEQUENCE: 16
ccgagatggg gttgataatg                                       20

<210> SEQ ID NO 17
<211> LENGTH: 21

-continued

<210> SEQ ID NO 17
<211> LENGTH: 21
<212> TYPE: DNA
<213> ORGANISM: artificial
<220> FEATURE:
<223> OTHER INFORMATION: OVOL2 primer

<400> SEQUENCE: 17
acaggcattc gtccctacaa a                                               21

<210> SEQ ID NO 18
<211> LENGTH: 21
<212> TYPE: DNA
<213> ORGANISM: artificial
<220> FEATURE:
<223> OTHER INFORMATION: OVOL2 primer

<400> SEQUENCE: 18
cgctgcttat aggcatactg c                                               21

<210> SEQ ID NO 19
<211> LENGTH: 21
<212> TYPE: DNA
<213> ORGANISM: artificial
<220> FEATURE:
<223> OTHER INFORMATION: TP63 primer

<400> SEQUENCE: 19
agagagaggg acttgagttc t                                               21

<210> SEQ ID NO 20
<211> LENGTH: 21
<212> TYPE: DNA
<213> ORGANISM: artificial
<220> FEATURE:
<223> OTHER INFORMATION: TP63 primer

<400> SEQUENCE: 20
tggtcgatgc tgttcaggag c                                               21

<210> SEQ ID NO 21
<211> LENGTH: 20
<212> TYPE: DNA
<213> ORGANISM: artificial
<220> FEATURE:
<223> OTHER INFORMATION: SNAI2 primer

<400> SEQUENCE: 21
ggggagaagc cttttcttg                                                  20

<210> SEQ ID NO 22
<211> LENGTH: 20
<212> TYPE: DNA
<213> ORGANISM: artificial
<220> FEATURE:
<223> OTHER INFORMATION: SNAI2 primer

<400> SEQUENCE: 22
tcctcatgtt tgtgcaggag                                                 20

<210> SEQ ID NO 23
<211> LENGTH: 20
<212> TYPE: DNA
<213> ORGANISM: artificial
<220> FEATURE:
<223> OTHER INFORMATION: VIM primer

<400> SEQUENCE: 23

```
gagaactttg ccgttgaagc                                                    20

<210> SEQ ID NO 24
<211> LENGTH: 20
<212> TYPE: DNA
<213> ORGANISM: artificial
<220> FEATURE:
<223> OTHER INFORMATION: VIM primer

<400> SEQUENCE: 24
gcttcctgta ggtggcaatc                                                    20

<210> SEQ ID NO 25
<211> LENGTH: 22
<212> TYPE: DNA
<213> ORGANISM: artificial
<220> FEATURE:
<223> OTHER INFORMATION: ZEB1 primer

<400> SEQUENCE: 25
gcacaagaag agccacaagt ag                                                 22

<210> SEQ ID NO 26
<211> LENGTH: 21
<212> TYPE: DNA
<213> ORGANISM: artificial
<220> FEATURE:
<223> OTHER INFORMATION: ZEB1 primer

<400> SEQUENCE: 26
gcaagacaag ttcaagggtt c                                                  21

<210> SEQ ID NO 27
<211> LENGTH: 21
<212> TYPE: DNA
<213> ORGANISM: artificial
<220> FEATURE:
<223> OTHER INFORMATION: TJP1 primer

<400> SEQUENCE: 27
cttaccacac tgtgcgtcca t                                                  21

<210> SEQ ID NO 28
<211> LENGTH: 23
<212> TYPE: DNA
<213> ORGANISM: artificial
<220> FEATURE:
<223> OTHER INFORMATION: TJP1 primer

<400> SEQUENCE: 28
aggagtcgga tgattttaga gca                                                23
```